(12) United States Patent
Robbins et al.

(10) Patent No.: US 12,340,883 B2
(45) Date of Patent: *Jun. 24, 2025

(54) TAKING PREVENTATIVE ACTION IN A SECURE HIPAA-COMPLIANT ENVIRONMENT WITH INTEGRATED HARDWARE AND SOFTWARE AND AN INTELLIGENT NETWORK, AND SYSTEMS AND METHODS THEREFOR

(71) Applicant: Therap Services, LLC, Torrington, CT (US)

(72) Inventors: Richard Allen Robbins, Lenox, MA (US); Justin Mark Brockie, Wolcott, CT (US); James Michael Kelly, Morris, CT (US); Asif Ali, Rocky Hill, CT (US); Mojahedul Hoque Abul Hasanat, Dacca (BD); A. S. M. Omar Faruq, South Windsor, CT (US); Sazzad Rafique, Glastonbury, CT (US); Tahseen Mohammad, Dacca (BD); Ummy Habiba, Dacca (BD); Suraiya Parveen, Mardsen Park (AU); Jeremy Ian Schulman Robbins, New York, NY (US)

(73) Assignee: Therap Services, LLC, Torrington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/419,798

(22) Filed: Jan. 23, 2024

(65) Prior Publication Data

US 2024/0212803 A1 Jun. 27, 2024

Related U.S. Application Data

(60) Continuation of application No. 17/941,163, filed on Sep. 9, 2022, now Pat. No. 11,923,053, which is a
(Continued)

(51) Int. Cl.
*G16H 10/60* (2018.01)
*H04L 9/40* (2022.01)

(52) U.S. Cl.
CPC ............. *G16H 10/60* (2018.01); *H04L 63/10* (2013.01)

(58) Field of Classification Search
CPC .............................. G16H 10/60; H04L 63/10
(Continued)

(56) References Cited

U.S. PATENT DOCUMENTS 6,132,724 A * 10/2000 Blum ..................... A61K 33/24
514/561
6,338,039 B1 * 1/2002 Lonski ................... G16H 15/00
705/2

(Continued)

*Primary Examiner* — Michael Tomaszewski
(74) *Attorney, Agent, or Firm* — Kleiber IP Law LLC; James R. Klaiber

(57) ABSTRACT

Initiating preventative action by a HIPAA-compliant computer security method and system for recording, using a video camera, electronic visual personal health information of at least two individuals, including an individual under care, and preventing unauthorized access of the user to the video information. The video is compared to physical attribute information of the individuals stored in the computer system's memory, and the individuals are identified by facial matching. The user's stored caseload has authorization profile information including access to individuals under care. The identified individuals are compared to the user's caseload information, and the user is granted access to part of the video of the individual under care, the video of the other individuals is blurred, and the resulting video is transmitted to the user's caseload for viewing. The video information is interpreted, a negative outcome is indicated, and a signal for initiating preventative action is transmitted.

35 Claims, 55 Drawing Sheets

Related U.S. Application Data continuation of application No. 16/695,591, filed on Nov. 26, 2019, now Pat. No. 11,475,983, which is a division of application No. 13/675,440, filed on Nov. 13, 2012, now abandoned, which is a continuation-in-part of application No. 13/600,402, filed on Aug. 31, 2012, now Pat. No. 8,613,054, and a continuation-in-part of application No. 13/600,388, filed on Aug. 31, 2012, now Pat. No. 8,615,790, said application No. 13/600,402 is a division of application No. 11/604,577, filed on Nov. 27, 2006, now Pat. No. 8,281,370, said application No. 13/600,388 is a division of application No. 11/604,577, filed on Nov. 27, 2006, now Pat. No. 8,281,370.

(58) Field of Classification Search
USPC .................................................. 705/2–3
See application file for complete search history.

(56) References Cited

U.S. PATENT DOCUMENTS

| | | | | |
|---|---|---|---|---|
| 6,463,417 | B1* | 10/2002 | Schoenberg | G06Q 10/10 |
| | | | | 705/2 |
| 7,139,914 | B2* | 11/2006 | Arnouse | G06Q 20/40145 |
| | | | | 713/172 |
| 7,689,437 | B1* | 3/2010 | Teller | A61B 5/411 |
| | | | | 600/300 |
| 8,191,152 | B1* | 5/2012 | Barker | G06Q 40/00 |
| | | | | 704/244 |
| 8,521,564 | B1* | 8/2013 | Ciechanowski | G16H 15/00 |
| | | | | 345/650 |
| 8,732,845 | B1* | 5/2014 | Barker | G06Q 40/00 |
| | | | | 704/244 |
| 11,475,983 | B2* | 10/2022 | Robbins | G16H 20/00 |
| 2007/0061164 | A1* | 3/2007 | Broselow | G16H 10/60 |
| | | | | 705/2 |
| 2007/0286520 | A1* | 12/2007 | Zhang | H04N 7/147 |
| | | | | 382/173 |
| 2011/0218814 | A1* | 9/2011 | Coats | G16H 10/60 |
| | | | | 705/2 |
| 2011/0257994 | A1* | 10/2011 | Givens | G16H 40/67 |
| | | | | 705/2 |
| 2011/0289443 | A1* | 11/2011 | Heaven | G16H 20/70 |
| | | | | 705/7.42 |
| 2012/0011565 | A1* | 1/2012 | Garlie | G06F 21/6245 |
| | | | | 726/2 |
| 2014/0085400 | A1* | 3/2014 | Kaus | H04N 7/18 |
| | | | | 348/14.03 |
| 2020/0126645 | A1* | 4/2020 | Robbins | H04L 63/10 |
| 2022/0206298 | A1* | 6/2022 | Goodman | G06F 3/011 |
| 2022/0210266 | A1* | 6/2022 | Kats | H04M 3/42042 |
| 2024/0212803 | A1* | 6/2024 | Robbins | G16H 50/30 |

* cited by examiner

Figure 18c

Audio Clip for Individual B
1840

Audio clip for Individual B
THU 30 AUG 2012
*********
(15:45:22) *********
(15:45:29) Individual B: It was mine.
(15:45:35) *********
(15:45:42) Individual B: Get away from me.
(15:45:45) Staff C (off camera): Stop that.
Please move.
(15:45:49) *********
(15:45:52) *********
15:45:20  □ ▷ ❚❚ THU 30 AUG 2012

Audio Clip for Individual A
1830

Audio clip for Individual A
THU 30 AUG 2012
*********
(15:45:22) Individual A: Why did you do that.
(15:45:29) *********
(15:45:35) Individual A: No, it was mine.
(15:45:42) *********
(15:45:45) Staff C (off camera): Stop that.
Please move.
(15:45:49) Individual A: Don't hit me!
(15:45:52) Individual A: That hurts.
15:45:20  □ ▷ ❚❚ THU 30 AUG 2012

Audio Clip For Individual B
1840

Individual B: Get away from me.
15:45:42  □ ▷ ❚❚ THU 30 AUG 2012

Audio Clip For Individual A
1830

Individual A: It was mine.
15:45:35  □ ▷ ❚❚ THU 30 AUG 2012

Injury Information

- Injury Type: Fracture
- Injury Cause: Abuse
- This event was: Discovered
- Time of Injury: 03 : 35 pm
- Specific Location: Living Room
- Treatment by: Physician/other medical
- Time of Treatment: 05 : 00 pm
- Treatment date, if different than event date: 08/30/2012
- Injury Size:
- Length (cm): 3    Width (cm): 2
- Depth (mm): 2
- Injury Color: Purple
- Injury Severity: Moderate (Nurse/Physician treatment)
- Injury Summary:
- Body Part(s): Arm Left
- Injury Summary:
- Witness 1
- Witness 2
- Attach Injury Photo   NONE Related boxes:
- Video Recording Time on Camera B 1621
- Video Recording Location on Camera B 1513
- Data in Database 1915
- Live Recording on Camera B 1620
- Hitting 1650
- Analyzing data for undesirable outcome 1930

| Login Name | IP Address | Activity Type | Module Name | Action | Form ID |
|---|---|---|---|---|---|
| demo-user1 | 123.49.42.65 | Log Off | | | |
| demo-user1 | 123.49.42.65 | Logon | | | |
| demo-user1 | 123.49.42.65 | | Individual Data | View | IDF-TIDEMCT-9D52FRSHG |
| demo-user1 | 123.49.42.65 | | Provider Administration | User delete | |
| demo-user1 | 123.49.42.65 | | Provider Administration | Account Deactivate | |
| demo-user1 | 123.49.42.65 | Logon | | | |
| demo-user1 | 123.49.42.65 | Login Failure | | | |
| demo-user2 | 123.49.42.65 | Log Off | | | |
| demo-user2 | 123.49.42.65 | | Provider Administration | Account Activate | |
| demo-user2 | 123.49.42.65 | | Provider Administration | Account Deactivate | |
| demo-user2 | 123.49.42.65 | Logon | | | |
| demo-user2 | 123.49.42.65 | Log Off | | | |
| demo-user2 | 123.49.42.65 | | Individual Service Plan | Save | ISP-TICT-A9329U8URZ |
| demo-user2 | 123.49.42.65 | | Individual Service Plan | Discontinue | ISP-TICT-A9329R56AQ |
| demo-user2 | 123.49.42.65 | | Individual Service Plan | View | ISP-TICT-A9329R56AQ |
| demo-user2 | 123.49.42.65 | | Individual Service Plan | View | ISP-TICT-A9329R56AQ |

Activity Tracking — 17 items found, displaying displaying all.

IP Address 2820
Action 2860
Form ID 2850

Figure 28a

| Date and Time 2830 | Activity Tracking | |
|---|---|---|
| | 17 items found, displaying displaying all. | |
| Date ▲ | Program ⇅ | Comments ⇅ |
| Jul 04, 2012 11:15:54 AM | | User: demo-user1 |
| Jul 04, 2012 07:08:26 AM | | Logon: demo-user1 |
| Jul 04, 2012 03:46:35 AM | 2nd Street (Group Home) Therap Demonstration Provider | Mozilla/5.0 (Windows NT 5.2; WOW64; rv: 13.0) Gecko/20100101 Firefox/13.0.1 |
| Jul 03, 2012 02:38:46 AM | Software Specifics 2840 | Deleted user.Login Name:demo-user3, |
| Jul 03, 2012 02:34:59 AM | | Affected User(s):demo-user3, |
| Jul 03, 2012 02:34:49 AM | | Logon: demo-user1 |
| Jul 03, 2012 02:34:40 AM | | Password Mistmatch |
| Jul 03, 2012 02:33:49 AM | | User: demo-user1 |
| Jul 03, 2012 02:33:46 AM | | Affected User(s):demo-user3, |
| Jul 03, 2012 02:30:51 AM | | Affected User(s):demo-user3, |
| Jul 01, 2012 02:30:12 AM | | Logon: demo-user2 |
| Jul 01, 2012 02:28:32 AM | | User: demo-user2 |
| Jul 01, 2012 02:13:27 AM | 3rd Street (Group Home) Therap Demonstration Provider | Mozilla/5.0 (Windows NT 5.2; WOW64; rv: 13.0) Gecko/20100101 Firefox/13.0.1 |
| Jul 01, 2012 02:13:27 AM | 3rd Street (Group Home) Therap Demonstration Provider | Mozilla/5.0 (Windows NT 5.2; WOW64; rv: 13.0) Gecko/20100101 Firefox/13.0.1 |
| Jul 01, 2012 02:12:55 AM | 3rd Street (Group Home) Therap Demonstration Provider | Mozilla/5.0 (Windows NT 5.2; WOW64; rv: 13.0) Gecko/20100101 Firefox/13.0.1 |
| Jul 01, 2012 02:12:49 AM | 3rd Street (Group Home) Therap Demonstration Provider | Mozilla/5.0 (Windows NT 5.2; WOW64; rv: 13.0) Gecko/20100101 Firefox/13.0.1 |

Figure 28a (Cont.)

Prevocational Services Documentation Record – Individual Summary Sheet
Status: New

| Report Description:* | Summary of Individual B | | | | | | | | | | | | |
|---|---|---|---|---|---|---|---|---|---|---|---|---|---|
| AGENCY: | | | Therap Demonstration Provider | | | | | | | | | | |
| INDIVIDUAL: | | | Individual B | | | | | | | | | | |
| SITE ADDRESS: | | | 4802 10th Ave., Brooklyn, NY, 11219 | | | | | | | | | | |

| P = prgm day / N = not prgm day | DESCRIPTION OF THE INDIVIDUALIZED STAFF SERVICE/ ACTION PROVIDED (based on the individual's Prevocational Services Plan) | STAFF PROVIDING SERVICE/ACTION MUST INITIAL THE DATE THE SERVICE/ACTION WAS PROVIDED. (NOTE: by entering initials, staff are attesting that the service/action was provided on that day. Initialing must occur at the same time as service delivery.) | | | | | | | | | | |
|---|---|---|---|---|---|---|---|---|---|---|---|---|
| | | 1 | 2 | 3 | 4 | 5 | 6 | 7 | 8 | 9 | 10 | 11 |
| N | Staff will explain tasks to Individual B | DECL RHE | VRBL RHE | PART RHE | INDP RHE | | | | DEMO RHE | INDP RHE | VRBL RHE | VRBL RHE |
| P | Staff will help Individual B while she plans | INDP RHE | | DEMO RHE | DECL RHE | INDP RHE | INDP RHE | | DECL RHE | PART RHE | DECL RHE | DECL RHE |
| N | Explain importance of toothbrushing | INDP RHE | VRBL RHE | INDP RHE | INDP RHE | INDP RHE | DEMO RHE | | | INDP RHE | | PART RHE |
| P | Explain steps for brushing | FULL RHE | PART RHE | DEMO RHE | DECL RHE | FULL RHE | DECL RHE | | PART RHE | DECL RHE | DECL RHE | DECL RHE |
| P | Explain importance of work safety | INDP RHE | INDP RHE | VRBL RHE | FULL RHE | VRBL RHE | | DECL RHE | FULL RHE | DECL RHE | INDP RHE | PART RHE |
| P | Ensure Individual B's safety precautions | FULL RHE | DEMO RHE | FULL RHE | DECL RHE | | | PART RHE | DECL RHE | FULL RHE | DECL RHE | FULL RHE |
| TOTAL # of SERVICES | | 11 | 9 | 12 | 12 | 6 | 6 | 6 | 12 | 12 | 9 | 12 |
| If Individual Received Other MA Service | Time left Prevoc | 05:00 | 03:00 | 12:00 | 11:30 | | | | 11:30 | | | |
| | Time Rtrn Prevoc | 06:15 | 03:15 | 18:30 | 13:00 | | | | 12:00 | | | |
| TOTAL PRGM DAY DURATION (circle one) F=Full: 4 or more hours / H=Half: 2 hours up to 4 hours / L2=less than 2 hours | | H | H | H | H | H | L2 | L2 | H | L2 | L2 | H |

Staff Signature Log

| SIGNATURE | Ray Helper | PRINT NAME |
|---|---|---|

TAKING PREVENTATIVE ACTION IN A SECURE HIPAA-COMPLIANT ENVIRONMENT WITH INTEGRATED HARDWARE AND SOFTWARE AND AN INTELLIGENT NETWORK, AND SYSTEMS AND METHODS THEREFOR

RELATED APPLICATIONS

The present invention is a Continuation application of U.S. patent application Ser. No. 17/941,163, filed Sep. 9, 2022 which issued as U.S. Pat. No. 11,923,053 on Mar. 5, 2024, which is a Divisional application of U.S. patent application Ser. No. 16/695,591, filed Nov. 25, 2019, which issued as U.S. Pat. No. 11,475,983 on Oct. 18, 2022, which is a Divisional application of U.S. patent application Ser. No. 13/675,440 filed Nov. 13, 2012, which is a Continuation-In-Part application of U.S. patent application Ser. Nos. 13/600,388 and 13/600,402, both filed on Aug. 31, 2012, and both of which are Divisional Applications of U.S. application Ser. No. 11/604,577, filed Nov. 27, 2006, which issued as U.S. Pat. No. 8,281,370 on Oct. 2, 2012. All description, drawings and teachings set forth therein are expressly incorporated by reference herein and claim priority upon the teachings expressly made herein.

FIELD OF THE INVENTION

The present invention relates to methods and system for acquiring and processing information collected from individuals having intellectual or cognitive disabilities, and for providing treatment, proof-of-service, and prevention of abuse and neglect based on that information.

BACKGROUND OF THE INVENTION AND DISCLOSURE

A goal of human service agencies may be to have more person centered documentation. Having the responses of a person is a key component for person centered documentation. For individuals with intellectual or cognitive disabilities who are receiving supports from others, there is a challenge to make sure that their goals and opinions are properly represented. In many cases these individuals are receiving support from multiple agencies with multiple oversights and monitoring organizations. Even within one organization there are multiple shifts of people with different access to information.

In applications requiring proof of positive or negative individual satisfaction, proof of service delivery, time, location and meeting individual goals for people with intellectual and/or cognitive disabilities who have guardians and or funded caregivers, or monitored by funding agencies, the state of the art is including an individual other than the person being documented for in the process of gathering information and treating information as if it is correct and reflects the individual with intellectual and/or cognitive disabilities. Unfortunately, this method does not include a system for receiving and reporting directly from individuals with certain cognitive and intellectual disabilities when it is shared among different caseloads, security domains and with defined access roles, called super roles.

Typically proof of service delivery, individual satisfaction of service provided and achievement of individual goals is documented using either paper or electronic formats. The desired information is entered on paper forms or some form of electronic database. These methods are prone to information which does not accurately reflect the wishes of the person who information is being documented on. Different staff, consultants, family members and others may either inaccurately interpret or falsely document information about an individual's satisfaction, achievement or additional responses. These are challenges with the current system of (static) (dropdown choices) answers, rating systems or defined check boxes to questions.

In addition, organizations providing these services work with significant budgetary issues. While most agencies work hard to provide excellent services, there are some agencies which do not have the same reputation, service quality or training and it is important to be able to have accurate documentation of service delivery and achievement of goals. It is a challenge for people with intellectual and/or cognitive disabilities to be able to self-report on the achievement of goals, satisfaction of service received, or potential problems such as abuse and neglect.

There are many current, significant issues with the prevention of abuse and neglect of individuals in this country receiving healthcare services. Having documentation by the same staff, consultants, or family of who might be causing the abuse and neglect may not be as optimal as having the individuals themselves giving their opinions on care, services and relationships. Not only does the abuse and neglect and negative outcomes need to be accurately documented, but so too does individuals' daily activities and positive. Staff might enter data in a daily service log for an individual where it might be the case that the individual did not receive that service on that day. Therefore, the need for accurately recording these activities is a challenge with paper based documentation or with the current standard in the industry, when it cannot be independently filled out and submitted by a person who is the subject of the documentation. It can also be a challenge when a staff can video an individual and then submit that video after the fact depending on the answer given. Broader real time documentation and data capture of all activities including treatment and other support activities, both positive and negative, may be preferable to selective documentation which could have either only positive results that might prevent negative issues from coming to light.

The proposed solution, aspects of the present invention, provides a method for direct connection of a phone, pc, smartphone, mobile device or other device connected securely to a central physical location over the internet or equivalent. Data measurements regarding the target individual could preferably be taken (or asked in real time in the form of questions) with a secure connection and then recorded and saved. The responses could be correlated and the information could be compared with predetermined person centered responses for specific individuals based on who was asking the questions and how the questions were asked.

This is particularly challenging for individuals with intellectual, cognitive, and developmental disabilities, which are lifelong conditions with varying degrees of impairments. They can have significant medical and other health conditions, and may often have emergencies. Individuals can receive support services beyond a traditional patient relationship. As they can receive funding from the government or other funding agencies, their daily activities, tasks, goals, objectives as well as medical or health conditions need to be documented by the entities providing supports to the individuals. Entities may only get paid upon proof of service delivery and proof of satisfaction by the individuals.

Access to Personal Health Information ("PHI") about health and related conditions is strictly regulated by the Health Insurance Portability and Accountability Act of 1996 ("HIPAA"), the American Recovery and Reinvestment Act of 2009 ("ARRA"), and Health Information Technology for Economic and Clinical Health Act ("HITECH") and other state and federal regulations which complicates providing support and services including analyzing and reviewing documentation.

Care and support for Individuals with Developmental Disabilities is often distributed among many people and organizations, including parents, service providers, doctors and other health professionals, volunteers and case managers and others appointed by various funding and regulatory jurisdictions. The responsibilities and privileges of different users (ranging from Parents to Guardians to health care professionals and staff members) may differ by funding sources and organizational structures, and thus a flexible system for understanding an individual with cognitive disabilities communication is essential.

For example, often an entity providing support to an individual may have different groups with separate staff providing various related functions, and thus processes may be used to control who has access to what information. Each of these services may need to be documented with proof of service delivery and service satisfaction. However, the possibility exists for various entities to be unaware of the services provided simultaneously by other entities.

Currently documentation may be done by asking an individual questions and then a staff member (or other person) documenting that information observing an individual and then entering documentation on a paper or electronic form. The information entered is thus interpreted by the staff member entering the documentation.

This method allows for the situation where different staff members observe an individual doing the same action or responding in a certain way and each staff member might interpret that information and document it differently. Given that an individual might have a lifelong condition and staff members can be transitory and thus have limited information, there exists a problem with the information flow available to a staff member. Some staff members might have worked longer with an individual and interpret non-verbal responses differently. This means the same response by an individual may cause different reporting interpretations. The responses would be stored so there is an ability to review responses as part of an audit or other look back.

In addition, an individual might respond differently to the same staff member asking the same question based on their psychological or behavioral condition at that time.

In the face of such challenges it becomes difficult for care providers to both ensure satisfaction of service provided to the individual and proof of service delivery provided to an individual. The misinterpretation of the responses received from an individual regarding satisfaction of services received might lead to incorrect documentation. These records might not reflect the individual's actual progress towards goals and consequently might not be analyzed properly as proof of satisfaction. Also, if the responses of service delivery are not recorded properly then the records may not be very useful to verify that the services were actually provided to the individual.

The system can have applications for an individual to report proof of service satisfaction or proof of service delivery. It may not be possible with the existing paper based or electronic documentation as other people document and interpret proof of satisfaction or proof of service delivery. For example, an individual might respond that he/she was not happy with the service or the appropriate service was not provided to him/her. But there exists the possibility that the staff entering documentation may record that the individual was happy or the appropriate service was provided to the individual. In such cases, the existing process of documentation of activities can fail to provide accurate proof of satisfaction and proof of service delivery.

Similar situations exist in other industries and populations. Situations with other cognitive conditions which might affect driving or other actions might need to be interpreted based on the individuals' intent and capabilities. This could include students, prisoners and minors with limited reporting capabilities.

Information may also be obtained from multiple actions, including verbal answers, facial movements, eye movements, variations in sound, hand gestures, body movements, body chemistry, temperature, photo or electrochemical modifications, facial or other tics, and other actions from an individual. These gestures can be recorded in the database. The system can store the information received in a database based on a variety of factors including the person asking the question, other people in the room, a recent history of actions regarding the individual, the individual's plans and goals, time and date, location and more. The system can have automated validations to generate notifications for potential negative outcomes such as abuse and neglect as well as positive outcomes. This data can be stored as multimedia documentation. Only individuals with appropriate access based on caseload and super role may be able to access the data.

Information can be generated from a video, tactile, thermal, electrochemical sensor, body worn sensors or audio capture system (including phones, computers, and other commercially available devices). The information is preferably captured and generated in real time. This eliminates the ability of a staff member to edit or only upload data which generates desired responses.

If potential for abuse and neglect is determined a specified subset of people based on caseloads and defined access roles, called super roles may view information as appropriate to review the situation. One benefit of the system is that the system can look for abuse and neglect across multiple caseloads and super roles based on predetermined rules.

SUMMARY

A system and method of generating information regarding one or more goals of an individual under care, comprising recording first information pertaining to one or more individuals, wherein at least a portion of the information pertains to an initial inquiry relating to one or more goals of the individual, transmitting at least a portion of the first recorded information to a computer system with a memory and a processor, storing, by the computer system, at least a portion of the first recorded information, storing, by the computer system, historical information, wherein the historical information pertains to an initial inquiry relating to an individual's care, and determining, by the computer system, a portion of first transmitted information corresponding to the historical information. The computer system further comprises any one or more of the steps of a) editing information pertaining to one or more individuals for viewing by a user authorized to view the information; b) populating data fields of an information request using formatted data; c) determining, based on an indicated negative outcome, a first preventative action relating to the first indicated negative outcome, and transmitting a signal for initiating a first preventative action; d) determining based on a first interpretation and a first caregiver action, whether at least a portion of the first caregiver action was appropriate; and e) determining based on an indicated need, an action to satisfy that need, and transmitting a signal for initiating the action to satisfy the need.

BRIEF DESCRIPTION OF THE FIGURES

FIG. 18c represents the modified audio clips for the user with limited caseload privileges;

FIG. 19a represents the sample screenshot of the section of the General Event Report form where the system can automatically enter real time incident details using live video recording;

FIG. 22 illustrates the process of entering an automated ISP Data form using the live video recording of the activity program;

FIG. 27a represents the sample screenshot of the access control feature by assigning combination of super roles, caseloads and agency-wide roles to users;

FIG. 28a represents sample screenshot of the users' activity tracking feature.

FIG. 36 illustrates the process of generating an automated Hab Checklist based on the data available in the system.

DETAILED DESCRIPTION AND PREFERRED EMBODIMENTS

Description will now be given of the currently preferred embodiment of the invention with reference to the attached FIGS. 1-36. It should be understood that these figures are exemplary in nature and in no way serve to limit the scope of the invention as the invention will be defined by claims, and the scope of the invention will be the scope of the claims, as interpreted by the Courts.

Introduction

Aspects of the present invention provide a system for managing documentation and other information from individuals under care among multiple security domains and caseloads. These individuals can include those with cognitive disabilities, prisoners, children in school, and infants ages birth to three. Embodiments of this invention may have applications for reporting proof of service delivery, proof of service satisfaction and other person centered documentation by people with cognitive disabilities in compliance with PHI across and within organizations in the cognitive disability field in compliance with HIPAA and other regulations and security procedures.

Embodiments of this system ensure that individual information is securely stored, thus eliminating the risk of loss of information as well as tampering or deleting information. It allows users to directly record information from an individual with cognitive disabilities or any other condition which renders the obtaining of accurate healthcare information difficult or impossible, directly into a database either unprompted or in response to prompts. This information may then be stored for audit integrity. It may also be compared with previous information from the individual to determine the accuracy of the answer received.

It can later be reviewed against future documentation to see if a response should be considered differently based on additional information. Because the initial response is stored securely in the system, what is changing is not the actual response but the interpretation of the response, so the documentation is still being recorded in real time as close to the point of delivery and occurrence as possible.

Overview

Figure 1:
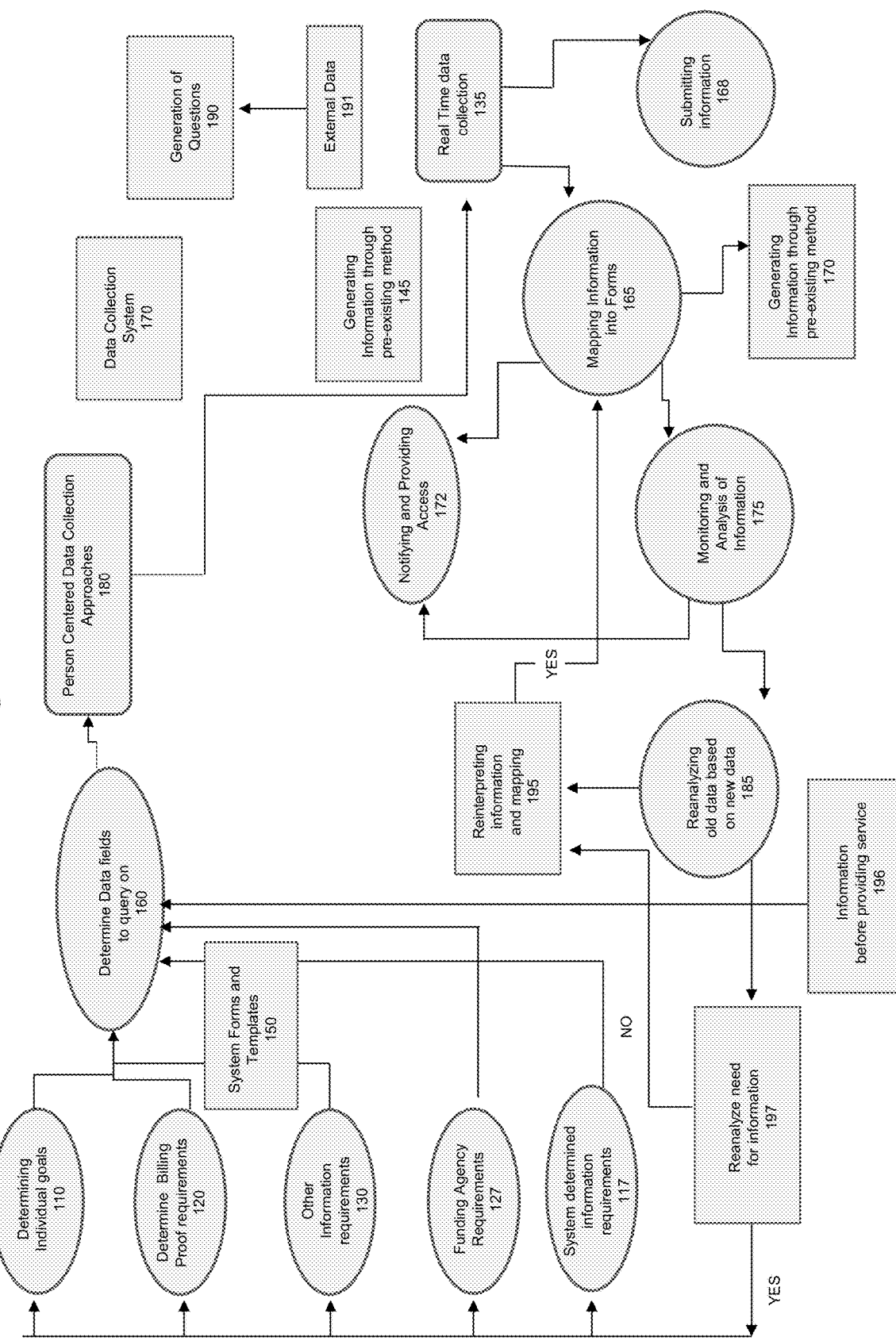
FIG. 1 illustrates an overview of a preferred embodiment of the disclosed system.

FIG. 1 illustrates an overview of the embodiments of the present invention system. Embodiments of the present invention require a number of steps in order to fully grasp, obtain, and understand the information sought. As shown in Determining Individual Goals 110, an individual has goals and objectives which are based on the individual's directive. Individuals' family, caregivers or the circle of support might help individuals in defining their goals and objectives.

In FIG. 1, Person Centered Data Collection Approaches 180 shows that the system has to determine how to collect data in a person-centered (See FIG. 29) and cognitively appropriate manner. In cases of cognitive disability or impairment different individuals may have different person-centered methods collecting data as shown by Determine Data fields to query on 160. The query includes asking questions, prompting for information, gathering data and collecting information. Individuals may express their responses in different manners and the system therefore needs to determine the appropriate method to collect data. The system might require the use of one or more methods to collect data.

Comparing the level of cognitive impairments of an individual, the system can determine if a single method would be enough to generate data from the individual's responses. If the system realizes that the response is not clear from the single method of data collection then it may suggest generating data in multiple manners. The system may also recognize that the same response from two different individuals might actually have separate meanings depending on the cognitive capabilities and perception of each person. A goal of the aspects of the present invention is the ability of the system to do just that—analyze, in a way a human overseer may not be able to, responses from different individuals to determine the meaning behind each, since identical responses from two different individuals may have different meanings. The system might recognize the characteristics of the surroundings of when the individuals may say the same thing with different meanings.

The system might also determine that there are different circumstances that even with the same answer from the same individual could have different meanings. The system may also recognize that there is not enough information no matter what answer might be generated from a single response and would therefore require data to be collected from multiple sources or multiple modes. The system can look at the process and the information about the situation and the surroundings and will not only focus on the apparent answer which may have different meanings depending on the situation and other factors.

This system of determining how to collect data in a person-centered or cognitively appropriate manner is based on a set of parameters and analysis which include both the individual as well as other individuals. The system may need to generate questions which do not reflect information about other individuals in other caseloads but might disseminate information about other individuals' answers or conditions or information. The system may also have the capability to ask questions which are relevant to improving the case or support related to the individual whom the questions are being asked about. The system may also have the capability to generate additional information for comparison purposes to validate and improve the reliability of the questions and information. The system may use hypothetical situations to ask questions in different manners. The different sets of questions may direct the individuals to construct messages in response to those situations. The system may then be able to compare the responses and determine the appropriate method to ask questions for each person.

Based on these individual directed goals and objectives, the system can adjust the types of information to be collected, queries to be generated and the types of analysis to be performed.

This information may be expressed in various modes or methods. Based on these individual goals, different information may need to be collected.

There may or may not be clearly understood information from an individual regarding their goals and objectives and information required to be collected. Part of the system is a process for collecting information based on the various potential goals, needs and objectives of an individual and then later adjusting reporting and analytic requirements based on the future reinterpretation of the prescribed goals and objectives.

It is possible that the system cannot identify the goals of an individual with certainty. The system could decide that there is a reasonable probability that the individual could have one or more of two or more goals. For example if the system thought there was a reasonable likelihood that the individual could have identified either goal or objective A or goal or objective B the system could provide documentation or tasks towards both objectives until it was clear which was the desired goal.

Requirements for Data Collection 120 shows that part of the requirements for data collection can be based on the Proof of Service Delivery 225 and Proof for Billing 120. Data may be needed on service delivery such as data for the person who asked questions to the individuals or the detailed information about the approaches taken at the time of providing supports to the individual. This information may be needed to prove that the appropriate services have been provided. The proof of service delivery may also be needed for the services that need to be billed. Using this information billing data is generated which is needed to prove that services have been appropriately administered and can be submitted as claims to be billed for. These are government, insurance reimbursement, corporate reimbursement or other reimbursements that are issued based on proof of proper service delivery. Objectives for the proof of service delivery may include reduction in fraud, government funding requirements and care and support requirements.

These data points can include audio, video, and other forms of data as shown on Data Obtained through Multiple Modes 911. Requirements can include having video or audio on certain activities. The activities recorded for video may include walking, turning around, facial movements, eye movements, running, raising of an arm, and eating. The audio recorded activities might include counting numbers, pronouncing names, vocalizations, breath sounds and answering to questions. This can also help create comparative points for data analysis.

Other Information Requirements 130 shows that part of the requirements for data collection may be based on requirements or objectives of the agency which provides services to an individual. The agency may have goals which include staff oversight, proof of service delivery, or efficient use of resources. There may be certain forms with specific data points for which information needs to be collected to maintain compliance with the agency policies. In one embodiment, the forms and data requirements can be established by various entities or people other than the individual but the data collected against these data requirements may be directly from an individual.

Funding Agency Requirements 127 shows that a funding agency may have information requirements. These can include proof of service delivery, outcomes, time, location, progress towards achieving a goal and individual satisfaction. The funding agency might require proof that is similar to or separate from billing requirements. In many cases there are separate state, federal, governments, private, non-profit or other organizational agencies which can provide funding. There may be data and information required by these funding agencies. In one embodiment, the forms and data requirements can be established by funding agencies, but the data collected against these requirements may be obtained directly from an individual.

Forms

System Forms and Templates 150 show that the system can have pre-existing forms and templates to assist in the development of data requirements. These forms can include templates which would only be shared within an Entity Providing Support 250. Forms could also include global templates available in the system which can be shared with other individuals or agencies outside the agency. They may include dropdown menus with choices, radio buttons, and general checkboxes to ensure that required or desired information is generated and received.

The system may also have preset forms or templates for other forms of data. For example, there could be preset picture formats which could include limits on size of file, length of video clip, quality of video clip, amount of movement of the camera or lens, color range, use of flash, distance from camera, number of people in a sequence, use of dimensions (3D), aperture, camera lens, among other type of formats.

For each of the types of data collection identified in Determine Data fields to query on 160 there could be forms or templates.

System determined information requirements 117 shows that the system can be designed to integrate with outside devices which could include health data capture devices, video devices 921, cameras 927, medical devices, audio devices 922, sensors 936, and other medical data capture equipment. These devices may have their own templates in the device. The system could note these templates as it captures data and information.

Information before Providing Service 196 shows the information collected which helps to make the initial assessments and determinations for what data to collect and how to collect. The system intakes an Individual, collects initial data and records any other observation. It is the initial information about an individual provided by the family, guardians, state, placement office and other forms provided by outside entities regarding that Individual 2940. There are diagnoses about the individual that were made previously along with any initial observations of the individual made by the people who are to be providing services. This is entered into the system to help make initial determinations. There may also be information provided directly by the individual. This information collectively helps create a starting point for the system to make decisions on how to collect information, etc.

Determine Data fields to query on 160 shows that Determining Individual Goals 110, Requirements for Data Collection 120, Other Information Requirements 130, Funding Agency Requirements 127 and System determined information requirements 117 together provides a set of data fields to collect.

Data Collection System 170 determines the method of asking questions or prompting information to collect or generate the information. Traditionally information has been generated by asking staff, guardians or other individuals' questions about the individual. The system is designed to determine which mix of a set of modes is to be used to gather information directly from an individual, including, but not limited to Video 921, Audio 922, Picture 923, Text 924, Real Time Video (925), Uploaded Video 926, Monitoring Cameras 927, Person Asking Questions 928, Multiple People asking questions 929, over cell-phone or other wireless device 930, changing sounds in environment 931, changing visuals in devices 932, previously generated data 933, Braille 934 to assist the visually impaired, tactile systems 935, electromechanical sensors 936, body fluids, saliva testing devices, body temperature and chemical sensors 937, audio capture system 938 or other modes which may capture information directly from an individual. The system may also use any combination of multiple items from this list. For example, audio and video can be used together to collect information from an individual.

The system can also combine multiple approaches to generate information for asking a question (Generation of Questions 190). There are a wide variety of approaches that the system can use for the people with intellectual and/or cognitive disabilities. For example, for the visually impaired individuals the system may use a 'Questions Reader' that would read out the questions generated by a device. In another case for the individuals with cognitive disabilities who are unable to read text, graphics can be combined to convey the message. Information can be generated by systems, phone, audio, staff, case working, family, the individual, volunteers, other manual or electronic devices or other appropriate parties. The system can recognize that each of these entities has a caseload and background. The same question posed by different devices or people might generate different information or responses. The system can both adjust the questions based on who is asking the questions and would also store information about how the question is being generated along with the responses to the question. Aspects of the present invention aim to maximize the ability of care providers to understand the issues facing these individuals, as well as the responses given as a result. By creating a question set tailored to that individual's needs, the embodiment of the present invention can best obtain and analyze given responses.

The system also allows for the interaction of external data into the process of question generation (191). This data could include weather, local traffic, ratings for movies or restaurants an individual might attend, internet searches, ratings or information on activities an individual might participate in, and any other relevant external information 440. The system can use that information to tailor questions in a person-centered manner. For example, the system can look into weather.com website for the information about the weather and use this information while generating queries for the individuals. This query might be generated to understand the individual's likings or dislikings about the weather. Some individual might get annoyed due to raining. In such cases, the system could get the information from the weather.com whether it will be raining today or not. If there is possibility of rain, the system can notify the staff to take special care of the individuals who do not like rain.

As shown by reference 911 in U.S. Pat. No. 8,281,370, data may be stored in the system's storage array. Access to information is based on caseload(s) and defined access roles (See FIG. 27). The documentation can include the information on caseloads, tracking, storage, and tagging as discussed in U.S. Pat. No. 8,281,370, including but not limited to the discussion Col. 5, line 21—col. 7, line 32.

Real Time data collection 135 shows that the goal or objective of this system is to collect person-centered data in as close to real time as possible. With the collection of a broad based set of real time data, the access by caseload and super role can be significant. The conventional approach has been for human beings to review data, videos and other information. This required giving access to staff or others to broad caseloads of individuals. In this system by providing a system with a caseload and the ability to review information as if it had caseloads for different individuals and of different staff then information viewed can be treated as if viewed by a system with an appropriate caseload and marked as viewed as such in each individuals file.

Generating Information through pre-existing method 145 which may be system generated forms and templates shows that the system processes the data. Initially the system stores the data. After the data is stored in the storage array, the data can be processed, mapped and analyzed. The system can create a query or series of queries to attempt to ask questions which will generate information. Based on the information available in the system, the system attempts to appropriately provide the optimal combination of generating accurate person-centered information while minimizing the cost and time required to answer the question. The system can generate the queries in any of the methods discussed in Data Collection System 170 and Person Centered Data Collection Approaches 180.

Initial Inquiries

When an individual is first in either the system or in an Entity Providing Service there is often a relatively limited amount of Person-Centered Data about an individual. In that case the system could create initial queries or approaches to gathering information based on more generic approaches to information based on typical information for other people with the same condition or set of displaying conditions or diagnoses. As additional information is gathered through the process, the queries could be tailored more to Individual based on their specific information and data. There could be a continual process of reviewing the analysis and queries which lead to more information and more analysis.

System Generated Inquiries 155 shows that the system then processes the answers and attempts to generate the next query, intervention or next request for information. In some cases there might be preset templates which generally walk through a set of inquiries or queries.

Mapping Information into Forms 165 shows that the system analyzes the information which has been collected using various methods and makes the best match it can to fill out required forms. The system can still store and maintain all of the pieces of data which went into trying to match the data requirements.

Notifying and Providing Access 172 shows that the system can notify staff, guardian, government officials and other people with appropriate access privileges about the information on individuals generated on forms and data fields 1940. The system can also provide proper access on individuals to staff authorized to view their information through appropriate caseloads and super roles.

Monitoring and Analysis of Information 175 shows that the data stored into the system is monitored and analyzed. The analysis of data received using different methods (170) can be performed by the system or by human beings. In each case access is defined by caseload and role. Activity is monitored and logged in an activity tracking log 2810.

The system can use algorithms and formulas to interpret the intent of the individual's information. This information can be checked against previous information provided by the individual and mapping can be performed for consistency, errors, possible fraud, possible abuse and neglect, and other issues which might arise.

Once data has been viewed by the system as part of this analysis, it may be recorded as 'viewed' or 'read' or with some other appropriate annotation in the database to indicate that the data or information has been viewed.

The system may have multiple accounts based on different caseloads and super roles to indicate when it has viewed or acted on information at the time of the viewing.

For example the set of caseloads and roles of the system might replicate the roles that an individual staff, guardian or other human might have. Then the system can perform certain analysis to detect fraud, abuse and health assessments, or other issues. Since the system can view these pieces of data or information, there is real time documentation that an analysis had been performed according to a certain set of rules or protocols. Only people with proper access to those caseloads and roles would be able to see that the system accessed that information and performed that analysis.

People with appropriate caseloads may be able to provide necessary information which may differ from information provided by other staff under different circumstances. The system can store this information for reference and analysis in order to generate answers and filling out forms. Stored data can be available for review with appropriate caseloads and access. If information from multiple users for an individual show a disagreement on a set of facts, the system can analyze the data combined with other information it has from sources including external sources and data collected in the system 185. The system can make a determination on the most likely correct set of facts. The system can also reanalyze previous facts in the system in light of having to interpret or remap data in this instance as multiple people may have had disagreement on information. This could be an indication that other data and information needs to be reanalyzed. If data is re-interpreted, that could mean that forms need to be changed or other processes and procedures need to be revisited 195. The system can determine if decisions were based on a given set of information.

Many agencies are required under HIPAA, HITECH, funding requirements, state or federal laws or policies of the Entity Providing Support 250 to perform certain analyses within certain periods. Having these analyses performed by system acting and documenting like a human being could allow proof that these analyses were documented. The system can function as an electronic staff member, robot, drone or other form of automated method to carry out tasks and supplement or replace an individual staff member or other person. It may not be sufficient to show that the information was in the system. It may be required to document that the analysis was performed by an entity (in this case a system rather than a person) with sufficient rights under roles and caseloads to do the analysis.

Depending on caseload and role, the system also has the ability to reanalyze and reinterpret previous mapping and interpretations of past data and information as shown in Reanalyzing old data based on new data 185. The system might have the option to take other individuals experiences into account or if the system notices any inconsistencies or changes required, the system can add a follow-up or changed comment based on the new analysis. The system can also flag or provide notification to people who had a proper caseload and role for the change.

Reinterpreting information and mapping 195 shows that after comparing and reanalyzing the responses of the individuals received under different circumstances, the system might change the interpretation of data while the original raw data and past information still available in the system. Since all the information is stored, the system can reanalyze the data collected using different methods and generate forms with the data having the best possible match.

The system can reanalyze the need for information 197 if there is a mismatch after comparing old data based on new information. The system can also reanalyze the goals and objectives of the Individual and data collected from the Individual or the surroundings of the Individual.

Figure 10:
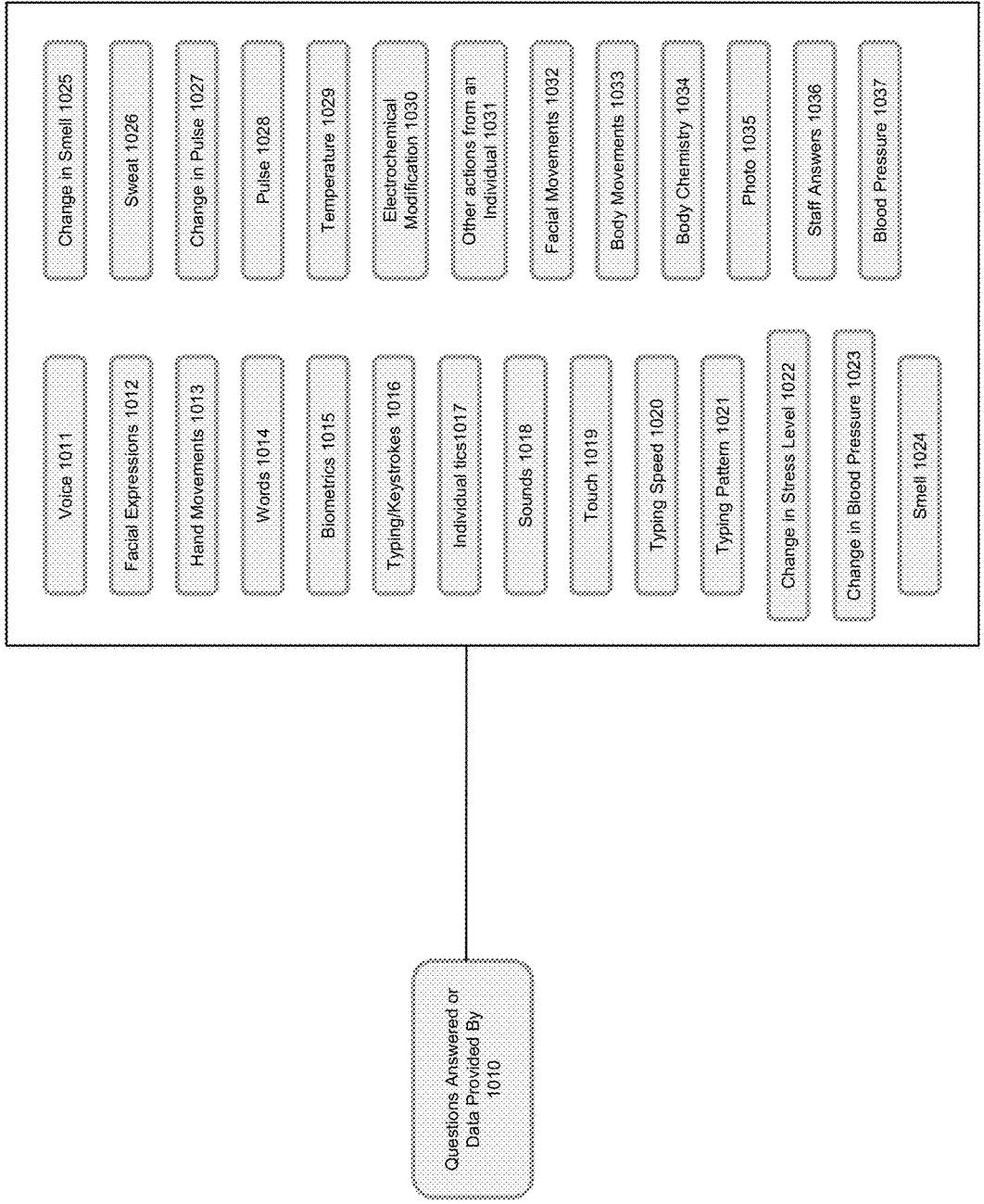
FIG. 10 the variety of modes of the responses obtained from the individual.

Currently and historically analysis may occur by individuals or committees (such as agency human rights committees, risk management committees or incident review committees) which meet periodically to review information. Under this system, the analysis could occur in real time by the system directly from information provided by an individual as shown in FIG. 10 and the environment. This accomplishes several objectives. The information is gathered directly from the individual with a cognitive disability; multiple types of information and data may be used in the calculation; and information can be saved so the data is stored in a real time manner, so even if an interpretation is changed later, the data was still created in real time. There is also the ability to create caseloads which are theoretically possible but could be quite difficult to create in real time.

As indicated in Submitting information to government and other entities 168, government and other entities might want the ability to view data across multiple agencies. A state director or state head of nursing or other senior positions which have access to data across organizations could want the ability to have analysis done. This is historically time consuming and resource intensive. With this system, the analysis could be possible in a manner consistent with maintaining the privacy of data and respect for the individuals. By the system performing the analysis with caseloads and roles ranging from access to one individual to having access to up to all individuals in the system, it is possible to determine information including fraud, abuse and neglect, and other types of objectives. The system can generate forms based on the analysis of all the information stored in the database. It may then be able to submit these forms to governments and other entities.

In addition, because the system is aware of staff and others caseloads, the system has the ability to notify proper people who should be made aware of the situation as shown in Notifying and Providing Access 172. When the analysis is done by staff, such notification of issues may only occur when the care provider takes the time to do so. Even when staff has time and effort to provide notification, there can also be other issues such as confusion on who should be notified for a given situation.

The system can also determine who should have known about a situation. Because of the access to caseload and role information in the system, the system may allow agencies to determine who might have had access to information to make a determination and also help prove who might not have had the information. This allows for a higher level of accountability on the part of service providers than exists currently.

There are many cases where staff, guardians, administrators or governments is accused of knowing certain information and not acting on information that they were aware of. This system can enable an Entity Providing Support 250 to establish the system under proxy caseloads and roles to see what information they might have known based on the information they could have had access to.

Oversight

Figure 2:
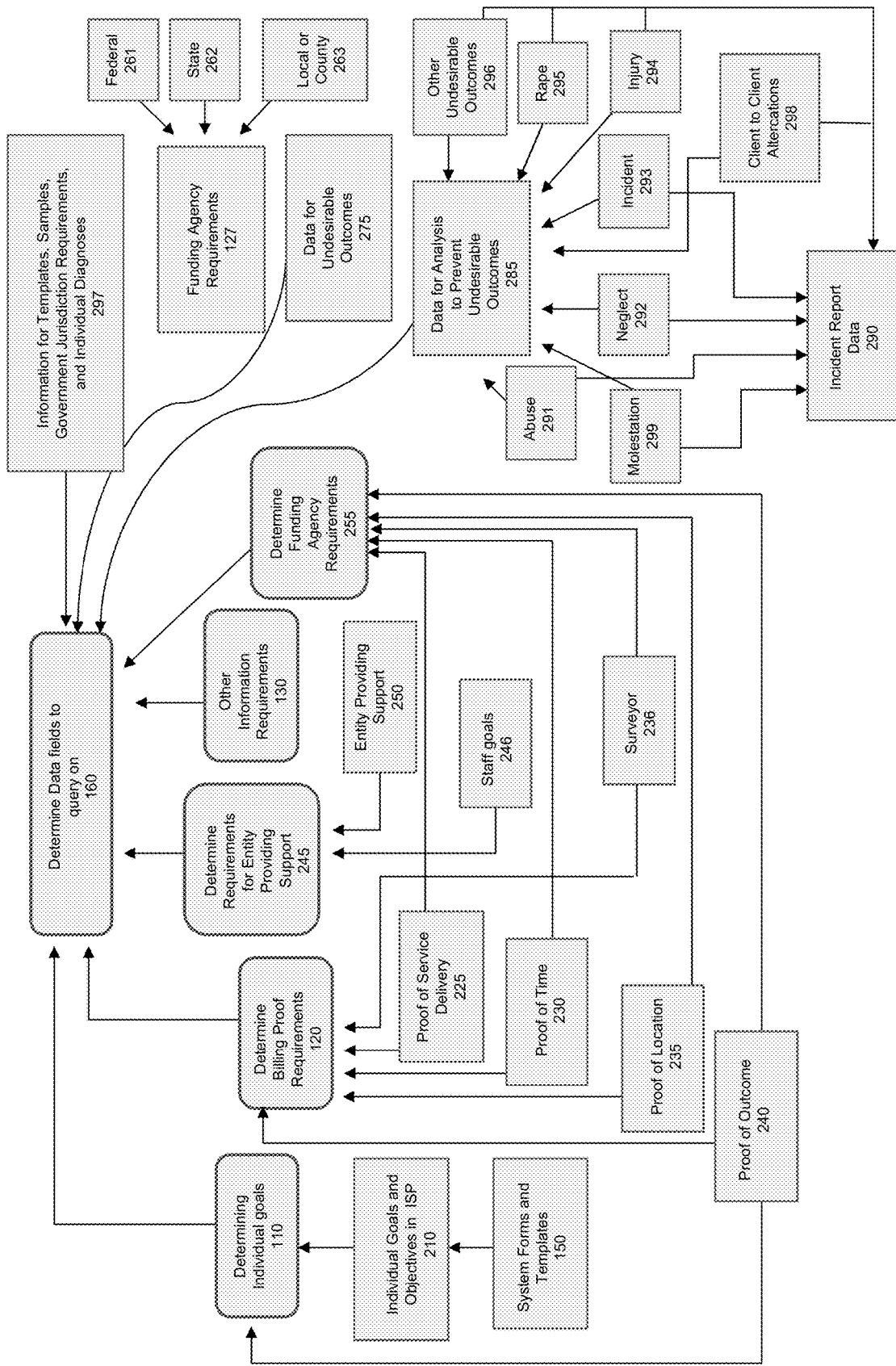
FIG. 2 illustrates an overview of determining data fields the information can be collected on as required for a number of objectives.

FIG. 2 illustrates the data fields information can be collected on. Information is required for a number of objectives. Information can be used for a number of purposes and analyses. These include the need to comply with Funding Agency Requirements 127 including Federal 261, State 262, Local or County 263, and other government jurisdictions or agencies. The government or funding agencies may require this information for a variety of purposes including funding reimbursement, awards of new contracts, maintenance of contracts, auditing or monitoring of supports provided to the individuals. These requirements may be derived from regulations, laws, websites, policy announcements, accumulated domain knowledge or knowhow, published forms, speeches, meetings or other means of generating requirements.

Federal agencies can include the Department of Health and Human Services under which the Centers for Medicare and Medicaid Services ("CMS") operates. The Office for Civil Rights which is responsible for HIPAA regulations operates under the Department of Health and Human Services. It can also include the Department of Education which is responsible for policies and procedures regarding Special Education.

In many cases data fields can be determined based on mapping or requirements to specific forms required to be filled out. There are a number forms or applications are available in the system for which the system can determine the data fields. These forms available for the entities that provide individual supports include T-Log or shifting notes, Individual Data, Emergency Data, Individual Home Page, General Event Report (GER), Witness Reports, Behavior Plan, Behavior Event Record, Individual Service Plan (ISP), Global ISP Template Library, Individual Plan of Protective Oversight and Safeguards (IPOP), Time Tracking, Advance Directives, Secure Communications (SComm), Management/Event Summaries, Demographic Report, T-Note, Calendar, Activity Tracking, Notification 3010. The system has detailed electronic health records of the individuals that include Appointments, Lab Tests, Vital Signs, Blood Glucose, Immunization Records, Infection Tracking, Height/Weight, Intake/Elimination, Menses Respiratory Treatment, Seizures, Skin/Wound, Medication History, Consultation Forms, Health Care Reports, Monthly & Detailed Reports, Medication Administration Records (MAR), Allergy Profiles, Advanced Directives, Diagnoses List, Health Passports, Care Plan (3040). The system has a number of forms that have been designed to collect billing information, including Service Authorization, Billing Record Entry, Attendance and the claim submission through Electronic Billing 3060. The system also has the individual's financial transaction form that records all the detailed information about the expenses and deposits 3050. Along with the individual specific forms the system has the Staff Scheduling 3020 and Training Management System 3030 applications that record detailed information about staff members on their work hours, training certifications, due/overdue trainings and training requirements.

Figure 24:
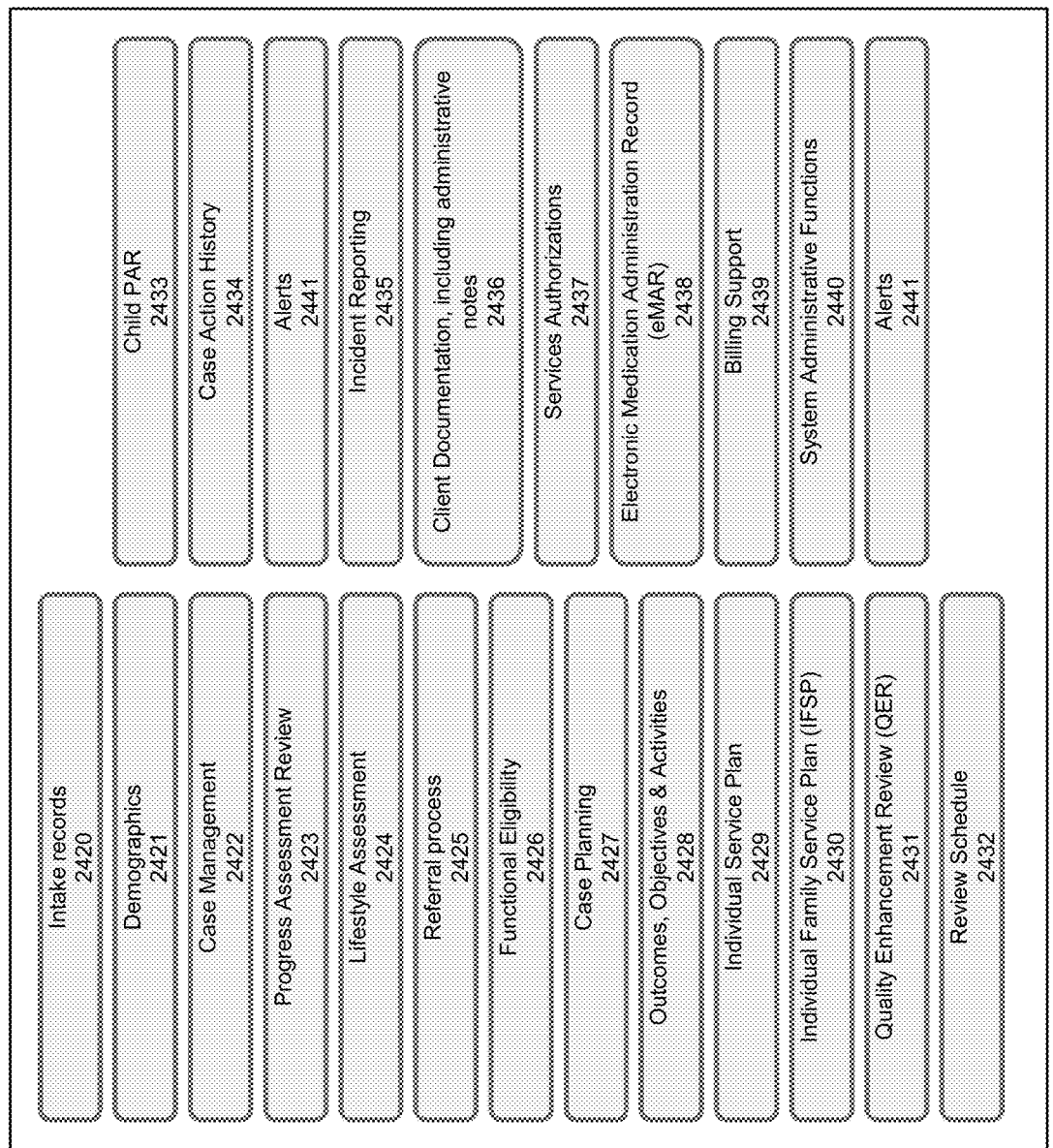
FIG. 24 shows the data the system can provide the funding agencies with for analysis.

There are many required forms in order for agencies, government entities, or jurisdictions to establish and document the goals. These forms record data about the Intake and Referral 3110, Oversight Documentation 3120, Multi Provider Reports 3130, Case Managements 3150 and Individual Budgeting 3160. This data is available for analysis by the funding agencies as shown in FIG. 24, Data Available for Analysis for Funding Agencies 2410.

Data may also be required based on the information found while determining individual goals 110. The goals and objectives can be determined based on the person-centered information about the individual discovered during the planning process. For example, abilities, skills, preferences, relationships, health, cultural traditions, community service and valued roles, spirituality, career, challenges, needs, pertinent clinical information, or other information that affects how supports and services can be provided. The Individual Goals and Objectives in ISP 210 include the individual's expected outcomes that are derived from the person-centered information. The goals in Individual Service Plan can also be based on the information found in other documents or plans including the Service Authorizations, Individual Plan of Protective Oversight, Risk Management Assessment and Plan.

Individuals may not be able to express themselves verbally to match the forms and questions in the goals. The system may allow an individual to provide a variety of responses and information in helping an entity providing support, staff, government entity or the system to create a person-centered set of individual goals leading to targeted outcomes and a plan. Using the person-centered Approaches 180 and the Data Collection System 170 the system can capture a set of information that allows an individual more input into the creations of their person-centered or cognitively appropriate plan and person-centered documentation. The system can directly store the individual input information and allows reinterpretation and remapping of the data in the future while still having the original data in the system at the same time.

Individuals can each help create and determine their own individual goals so that the individual service plans reflects the person's needs and preferences. If the person is not satisfied with the services, the individual may choose to modify the services according to his/her needs and preferences. Therefore, data may be required to help determine the Proof of Positive or Negative Individual Satisfaction 215. The information about the individual's satisfaction can be determined based on the information about individual goals identified by the individuals and the records of service delivery. The system has the information collected by generating questions that are related to the services required to achieve the desired goals of the individuals. The system may use the person-centered Data Collection Approaches 180 to determine how to collect data that may help create person-centered documentation. The system may compare these records to analyze the progress of the individual towards the desired goals and interpret the information reflecting the individual's level of satisfaction.

Accessing Data

Data may be needed as the Proof of Service Delivery 225. The system may use the information about the service delivery available within the system including audio, video, pictures and responses collected using system generated queries. While generating the information about the service delivery the system may require collecting information about the individuals' identification information to ensure that data has been collected for the correct individual. It also requires the identification information about the staff involved in service delivery and data collection. The system may use the information about each of the queries to determine if the appropriate service has been delivered to the individual.

Figure 30:
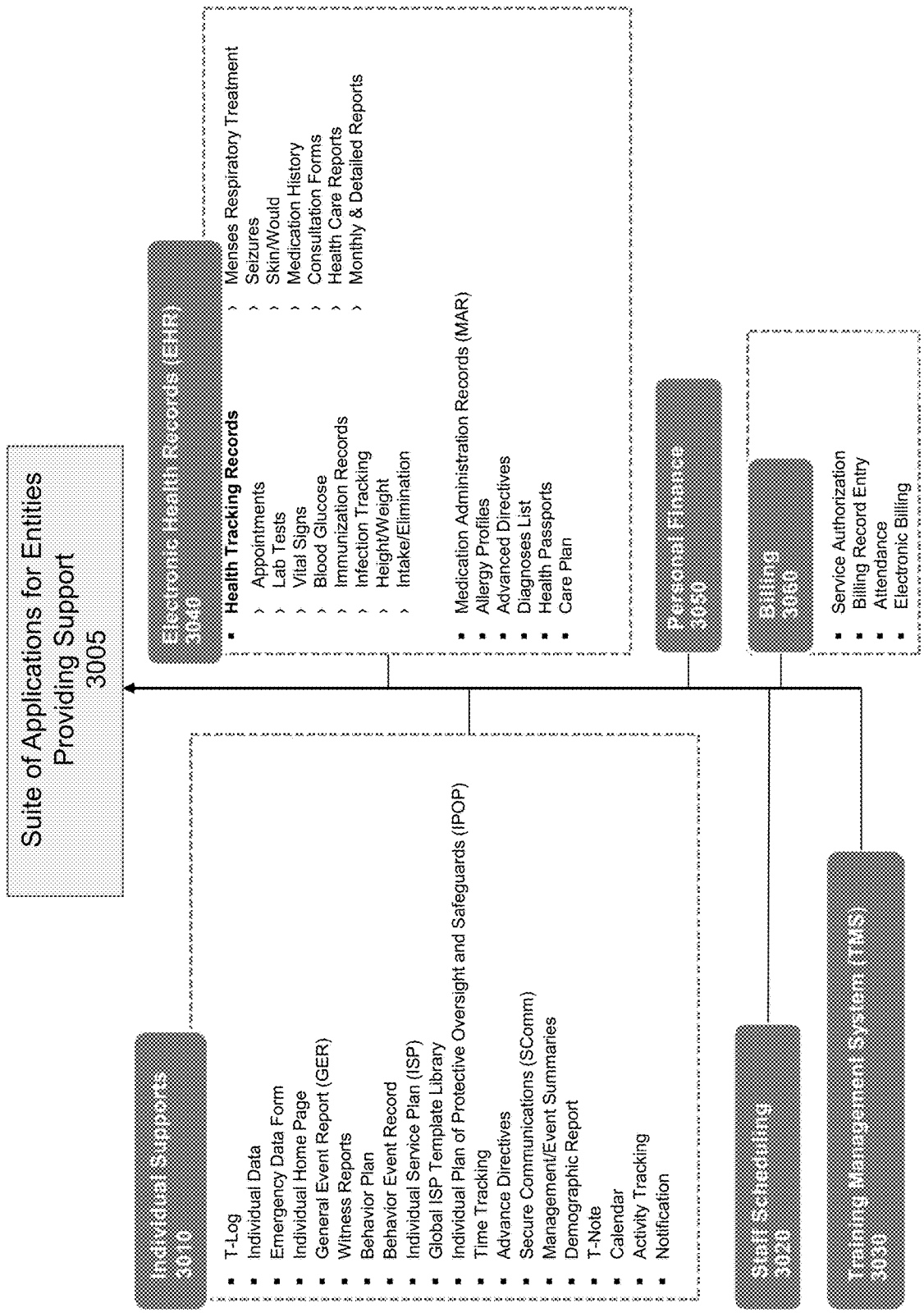
FIG. 30 illustrates the overview of the suite of applications that have been designed for the entities providing support to the individuals.

The proof of service delivery is needed to determine billing proof requirements 120 and to comply with the determination of Funding Agency Requirements 255. This information is also as the proof of performance validation for an Entity Providing Support 250, staff, or other entity requirements 130 to proof an Entity Providing Support 250 has complied with their contract or oversight. Examples of data fields for which queries and information may be needed are shown in FIG. 30. The fields include demographic data, electronic health records and other types of information.

Data may be needed to prove the time of when something occurred as shown in the Proof of Time 230. The system may use the time of when the query has been generated, when service has been delivered and when the data has been collected. If any service documentation requires a staff to sign off or review or if any staff makes any changes to the record, the system may also need the time of when the record has been reviewed or updated. The proof of time is needed to determine requirements for Billing 120 or Funding Agency 255.

The Entity Providing Support 250 represents the agency or group or person is providing support to an individual. This support may be provided by the government. In many cases governments directly provide social services. In other instance either non-profit agencies or for-profit agencies can be established to provide various services and supports. The for-profit or non-profit agencies can receive funding through a mix of sources including government contracts, insurance reimbursement, family funding, individual funding, and other places that could pay for the services and supports provided. The Entity Providing Support 250 can also be a family or family member. In many cases family members provide supports and help to other family members. In some cases they are reimbursed by government agencies, insurance companies, other family members, or other places outside the family, and in some cases the family provides support or services at no cost or with no reimbursement. There are other volunteer groups, good Samaritans, church or other religious organizations, or other types of organizations which may utilize the system as part of providing supports and achieving the goals outlined. There could be instances where the Entity Providing Support 250 is the individual himself or herself who may access the system. The Entity Providing Support 250 can be any grouping or organization or one or more people who or which utilize the system. The system may require data fields based on the requirements of one or more Entities Providing Support which are determined by the system as shown in 245.

The location that something occurred at may be required as the Proof of Location 235. The information about the location where the service has been delivered or the data has been collected can be determined using Global Positioning System (GPS) or by generating queries. The proof of location is very useful to analyze any undesirable event that occurs within the Entity Providing Support. In such cases, the specific location of where the event has occurred is useful to analyze the event and report on these events. This information can be used to determine requirements for Billing 120 or Funding Agency 255.

Data may be needed as the Proof of Outcomes 240. The outcomes are used as part of the Individual Goals and Objectives in ISP 210. They can also be required as Proof for Billing 220 or performance of Entity Providing Support 250 functions for Funding Agency Requirements 127. The proof of outcomes can also be used to measure and prove state Medicaid Assurances to Federal Authorities such as the Centers for Medicare & Medicaid Services (CMS). The funding agency may require data to determine the individual budget for a specific service. To do so, the system may have data fields for creating service authorizations, defining services and then determining individual budget amount for a specified budget period.

Data may also be needed to help determine the Staff Goals 246. The system may record the details of the staff members' goals and objectives as well as their training certifications, training requirements. This information can be useful for determining requirements for Entity Providing Support 250. The system may require the data fields as required by the Surveyor 236 who may review or monitor the supports provided to an individual need to be captured by the system. This information is needed to determine the requirements for billing 220 or Funding Agency Requirements 255.

The system has a number of templates, sample and information about the government jurisdiction requirements and also for individual diagnoses 297. For example, to report an incident the template state form needs to be filled in as per the state requirements. To obtain data for the emergency fact sheet containing demographic, medical, contact behavior and other information about an individual the system may have template form that has been designed according to the government jurisdiction requirements. As a result the system may need to determine appropriate data fields to query on.

In some cases, there might be some undesirable outcomes for the individuals. In such cases, the system may need to determine the Data for Undesirable Outcomes 275. The system may determine this information by analyzing the responses captured directly from the individual. The information about the surroundings and the people involved with the event may be needed along with the detailed information about the incident occurred. If any injury occurs, the system may need to report the event with the details of the injury including injury type, injury severity, a picture of the injured body part, the cause of the injury and the treatment provided to the individual. In order to determine the cause of the event, the system may require to collect information in multiple manners to report and also to analyze so that preventive measures can be determined for the future.

Data may also be needed for analysis to prevent undesirable outcomes 285. The system could collect information about the individual that might cause negative impacts on the individual's health or welfare. For example, the individual might have allergies to nut flavor and this information needs to be collected by the system as this may harm the individual's health conditions. This information can be used for analysis on determining steps to be taken to prevent harm to the individual. Data to prevent undesirable outcomes could useful to prevent a number of undesirable events. These include Abuse 291, Neglect 292, Incident 293, Injury 294, Rape 295, Client-Client Altercation 298, Molestation 299 and other Undesirable Outcomes 296 which may include Suicide. This information about the undesirable incident may also be needed to report the incident. It has been represented in the Incident Report Data 290. The system may require the details of person who were involved in each event including the person who reported the event, who were notified about the event, who reviewed or sign off the report, who witnesses the event. The system may record the video or audio clip of the event as a backup information which can be used for analysis.

Transfer of Information

Figure 3:
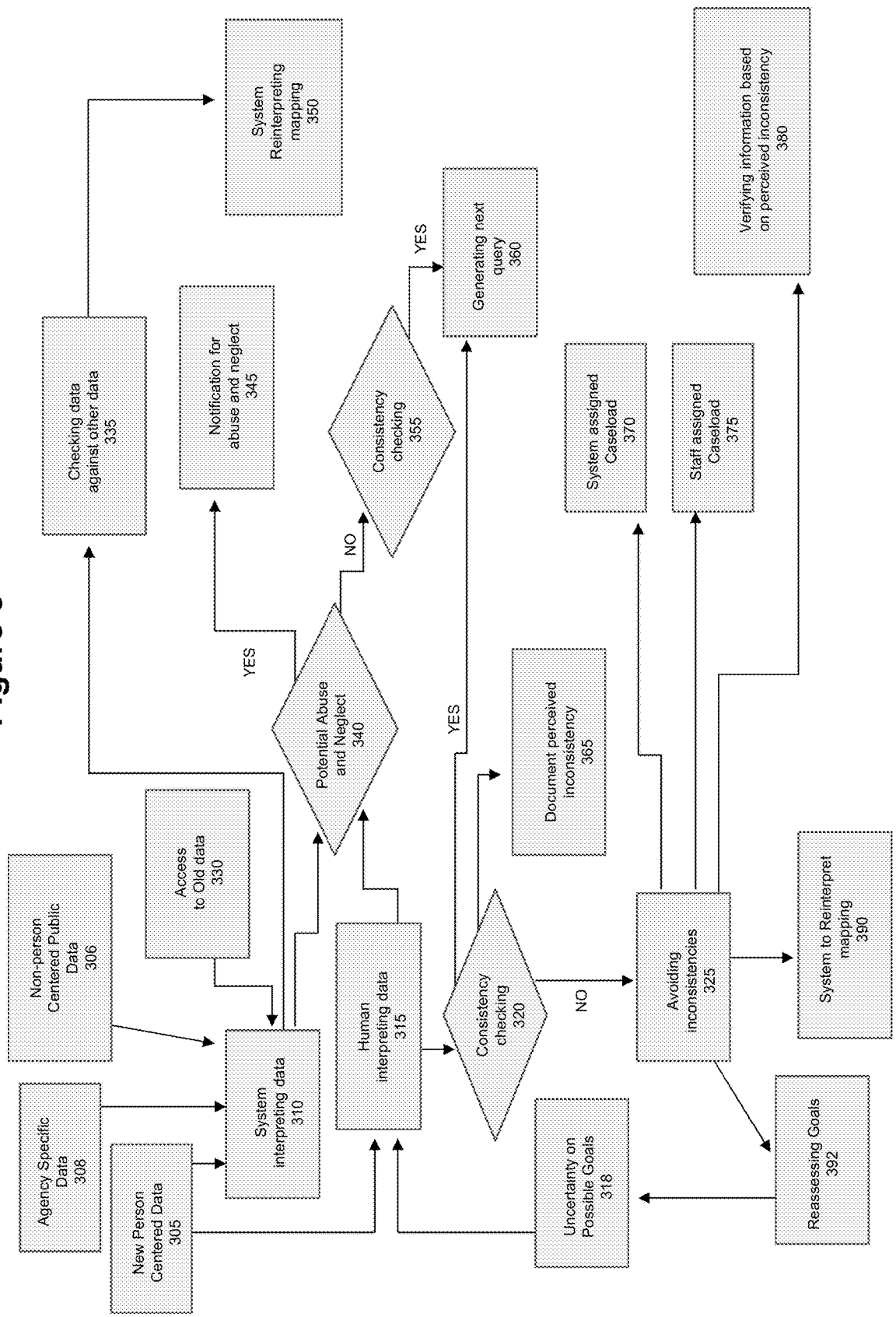
FIG. 3 illustrates an overview of the information flow process.

FIG. 3 illustrates embodiments of the Information Flow Process. Referring to FIG. 3, Information can be received from multiple places, people, modes and formats as shown by FIG. 9. Once the data is in the system it can be viewed, analyzed, read, interpreted or used based on caseloads, roles and objectives. Once data is stored, the system can analyze the information using point scoring method, regression analysis, outcome or input based triggers or other forms of analysis (See FIG. 8). After analyzing the information the system may interpret the results to determine the possible outcomes. This information can be analyzed further and mapped with other information if reinterpretation is needed in the future.

The new data as in New Person-Centered Data 305 which is collected by gathering information from an individual under a particular set of conditions. The system can also gather non person-centered data to analyze individuals' responses. The Non Person-Centered Data 306 could be information on weather or a plot of a movie which an individual attended. For example, if an individual watched a movie where a character performed a certain action and then after the movie the individual had a behavioral event record which included that similar action or set of actions, the fact that they had just seen a movie might lead to a different interpretation of the reaction by the staff or agency. If the individual had not exhibited this action previously, knowing that it was in the movie might cause the reaction to be to avoid future similar movies or take precautionary measures if similar movies were attended, rather than treating this as an action which needs an escalated response. In addition, action could be taken to train staff on types of movies to take individuals to or how to prepare in advance for possible reactions to movies. In this case the plot and actions of the movie could be considered as Non Person-Centered Data 306 and the information might be received from an online movie database. The system can combine the Non Person Centered Data with New Person Centered Data and/or other person centered data that could provide a different interpretation and analysis. Non person-centered data 306, Agency Specific Data 308 together with the old data shown in Access to Old data 330 which was previously stored in the database can be combined to be interpreted either by the system (System Interpreting Data 310) or by human beings (Human Interpreting Data 315). The system performs necessary analysis of data, compares new data with previous data, and makes reinterpretations if required. Reinterpretations might be needed for several reasons. These could include a request for reinterpretation by a human being who performed an analysis, was in an oversight situation, had new information or had other reasons to request a reinterpretation. For certain events, there could be flags set to do reinterpretations after a predefined period of time after an event such as death, abuse and neglect, after an individual goes missing, or other triggers. For such cases, reinterpretation is done by the system after that period of time.

A reinterpretation could also occur as the system becomes aware that there is new information or new data related to this person or situation. This could include new facts for the situation. A reinterpretation might be needed to analyze how to view these certain facts. For example, the individual might be using an assisted technology device which broke and the assumption was the individual broke the device, which led to other conclusions. But then information is found from other source that another person broke that device. That could prompt a reinterpretation. There could be automated analysis going on by the system looking for broader correlations and changes in assumptions, patterns, regressions and correlations. A reinterpretation could occur automatically or randomly as the computer is processing large amounts of data. The reinterpretation could also be inaccurate or changed again later. For example, there could be instances where all interpretations would say there is a 52% chance that something meant X and 48% chance it meant Y. After further analysis with new information, the system could reinterpret the original raw data based on new information and come to new conclusions. Additional reinterpretations might be needed in the future depending on the situations. As the original raw data remains, the documentation can be considered to have been done in real time or contemporaneous with an event or activity even when an interpretation or reinterpretation occurs at a later point. The system then maps this information into the predefined forms and templates and submits these forms to government or other agencies for jurisdiction. Human beings may access the system based on appropriate caseload and roles and all activity can be tracked and logged. They can review and compare between the new and old data and reinterpret information if there is any inconsistency in data.

Abuse and Neglect

One significant issue with people having cognitive disabilities is abuse and neglect as well as exploitation and mistreatment. There have been many reported incidents and issues of staff members, guardians or others causing harm to an individual through abuse and/or neglect. This system can provide a means of automating the detection of abuse and neglect as well as reducing the potential for future abuse by analyzing information. By using information directly from individuals (See FIG. 10) with cognitive disabilities in real time combined with access to reviewing data across multiple caseloads, the system could alert someone with proper caseloads when an increased possibility of abuse and neglect arises. The system could also take certain actions to attempt to prevent or minimize abuse and neglect based on the information in the system.

If the system determines a potential for abuse and neglect 340 that reaches a determined threshold, a notification could be sent only to those-staff that have the proper set of caseloads and roles as indicated in the notification for abuse and neglect 345. The notification could be based on who would have had access to the information to make this determination. For example, if a staff member providing support at one entity had been involved in an abuse and neglect allegation, and a situation was occurring at a separate entity providing support where similar antecedents were occurring, the system might not be able to just notify the staff at the second entity. Because in doing so, it could compromise privacy or information regarding the abuse and neglect which is a possibility or allegation at the first entity providing support. However, a staff member of a third party entity or organization or Protection and Advocacy with proper caseloads such as a state government, oversight agency, legal system, or other identified group or organization, might be notified with this information and take actions.

There are certain items which could be set up to generate certain broader reviews for abuse and neglect, positive or negative outcomes. This could include death, starvation, physical abuse, restraints, financial mismanagement, theft, fiduciary abuse, molestation and other items which could require protection and advocacy. Some of this list could be generated from governmental regulations, policies of the entity providing support or other external rules. This list can be generated by people (including individuals with disabilities, staff, family, caregivers, volunteers, guardians or others) or by the system. Items generated by people or the system would be those items which people, agencies, government regulators or others could determine require a broader review. In addition, the system would learn over time which events or situations might require either a broader review or a later review for possible reinterpretation. The review could involve factors such as the system doing a larger data review for reinterpretation or analysis including a broader set of information to process as well as processing over a longer period of time. The review could also involve a prompt for human interaction on reassessing the facts and interpretations in certain situations.

Checking data against other data 335 indicates that system may check data received using various modes and methods from individuals, staff, location and others. The system may not necessarily be limited to words to determine abuse and neglect. For example, if video was being maintained for an individual and the system determined an unexplained change in behavior or condition, such as, a person flinching or a noticeable change in the pace of walking from one day or within a period to another, then that might trigger a review of information. Certain changes in responses to questions regarding goals and objectives could also trigger a review. The system could also compare if there has been a change to the regular temperature of the individual, change of pulse rate, change in stress level, hand movements or any other change in regular mannerisms. Depending on the analysis the system could proceed with further investigation.

Because the system is maintaining a history of information and data directly from and about an individual with cognitive disabilities, there are many instances where potential abuse and neglect might be considered. Because the system is caseload based and reviews and analysis are logged and tracked, there is the ability to have either the system or appropriate people notified and flagged regarding a potential problem.

If the system determines that there are other issues regarding fraud, abuse, neglect and mistreatments, depression, health risk or suicide risk, appropriate people can be notified based on caseload and roles. By having the system document its analysis in real time, entities providing support can show that they are proactively looking at and reviewing their data to avoid fraud and other issues. Because the raw data and the information coming directly from an individual with cognitive disabilities is in the system in real time, if the need to change an interpretation of the data arises, based on future changes in interpretation the original data might still be available with original time and date stamp and data can be reinterpreted within a significantly reduced amount of time as indicated in System Reinterpreting Mapping 350.

With new pieces of data the system can check for consistency with previous mapping and interpretations as shown in Consistency Checking 320. The system can be set to check for validations and consistency in real time as questions are being asked. In this case, if there are no changes in interpretation or mapping the system can continue generating new information or the next query as shown in Generating Next Query 360.

The system may have the ability to determine inconsistencies in answers generated by individuals, staff and external devices as indicated in Document Perceived Inconsistency 365. The system is able to factor in staff answers. The system can look for inconsistencies of answers in several areas which includes between an individual staff or other person entering data, comparing data from a staff member and from an individual on whom the data is being entered, comparing the data being entered by a staff member in multiple organizations, comparing information entered by a staff member and that available through external data such as weather, traffic and general data available through the internet or other common societal data. Biometric approaches could also be used on staff.

The system can also factor in entities providing support information. Multiple agencies may provide support and have documentation on the same individual or individuals. The data could be collected the same way any other data is collected—and then data can be viewed or analyzed when combined based on access roles and caseloads. The data can either be generated automatically by the system directly from individuals or could be entered by people (staff, volunteers, family, government employees, etc). The data could be held in a system which allows analysis across multiple entities either because it is in the same storage location or because the multiple storage locations have a way to communicate and exchange information and data. The system could have the information about all the service providers or locations where the individual would be attending activity programs. The system could also collect and map all the data concerning the individual who receives services from multiple entities and analyze individual's progress under each entity. By utilizing caseloads across data from multiple entities there might be patterns which provide a change in interpretation for certain fields and information.

To avoid inconsistencies 325 in mapping information, information is cross checked with that of the previous information stored in the database. Determining the necessity of reinterpreting information 390, the goals and objectives of Individuals are reanalyzed 392, uncertainty on possible goals 318 are re-determined and information is verified based on perceived inconsistency 380.

System Assigned Caseload 370 shows that one flexible mechanism of the system is the ability to assign any possible combination of caseload and super roles. This can have many benefits. One use would be to see the information and data situation through the caseload and role of specific staff. This allows the ability to know what they could have and should have known at what point in time. There could be an instance where a staff member took action regarding an individual which resulted in a negative outcome. The system could simulate what alternate action the staff member could have taken at that point based on information available at the time. The system could also simulate to see if that staff member would have had different information to make that decision had they been given different caseloads and super roles. For example, Individual A, Individual B, and Individual C are in a location (which for example could be a home, a park, or a shopping center) and Staff S has previously had access to information regarding Individual A and Individual B because Staff S has access to their caseloads. Staff S might have taken an action or engaged in an activity which triggered a predictable reaction from Individual C which caused a problem for Individual A and/or Individual B. If Staff had previously had access to the caseload of Individual C at the point that decision was made, the outcome might have been prevented.

In another use of the system, an entity providing support could simulate caseloads to know what the optimal caseloads are to be assigned based on the information in the system. Because the system has information directly from the individuals receiving support and also has information about how the staff has reacted and functioned; the system can provide such caseloads. The system can have the history, training and skillsets of staff as well as information regarding individuals. Using this information the system can predict in advance which mixes of staff members and individual caseloads could have positive outcomes.

Staff Assigned Caseload 375 shows that the system can assign caseloads to staff members who are supporting and providing services to individuals by providing them broader access. This can enable them to document information received directly from individuals under different situations. Using the electronic documentation tools, the staff members may document the data received from an individual. The system can verify the user's password and other credentials for proof that the person is who he or she claims to be. The raw data or documentation coming from the individuals can also be generated using a variety of methods as identified in FIG. 10. Some of the data may not require password if the data is from video or biometrics or internal devices for example. Even knowing the source of data does not make the data factually correct. Data can be factually incorrect either intentionally or for unintentional reasons.

There could be issues with staff documenting individuals' responses. The staff might miss something while entering data or might not be good at writing. Sometimes, staff members might try to cover something up and therefore there exists the possibility of inaccurate data collection. The data recorded by the staff needs to be verified, and the system can do so by comparing other available information which the system gathered directly from the individual. If the system analyzes that one of the staff member is not appropriately using the assigned caseload privileges or is trying to violate the assigned caseloads, then the system could decide what information the user should access and may block access to certain caseloads if needed. The system might need to reinterpret the data to verify the accuracy of each documentation. For example, Individuals with varying cognitive conditions may enter data which could be considered inaccurate or wrong by other people or even by themselves at a later time. As the raw data can be stored with date and time stamps, the system can help correlate that data against other facts and help determine what interpretation and weight should be given to each piece of data.

By using these tools, an Entity Providing Support 250 or government entity could see the effectiveness of specific staff or an entire entity providing support. There is an increased movement to outcomes based funding and outcomes based approaches. Without significant data it could be difficult to determine effectiveness towards outcomes. The system can provide the government or funding agencies with analytics including detailed service logs and reports for the entity where the individual is receiving services. Using these service logs, the system can also analyze whether a particular entity is providing appropriate services that the individual requires to achieve goals or objective. If the analysis results in an increase in positive outcomes, the government or funding agency may decide to continue services for the individual under the existing entity and may provide funding for the next budget period. Otherwise, the government or funding agency may decide that the existing entity is not providing appropriate services and either suggest that the individual should be referred to another entity or suggest improvements in supports.

Data Storage

Figure 4:
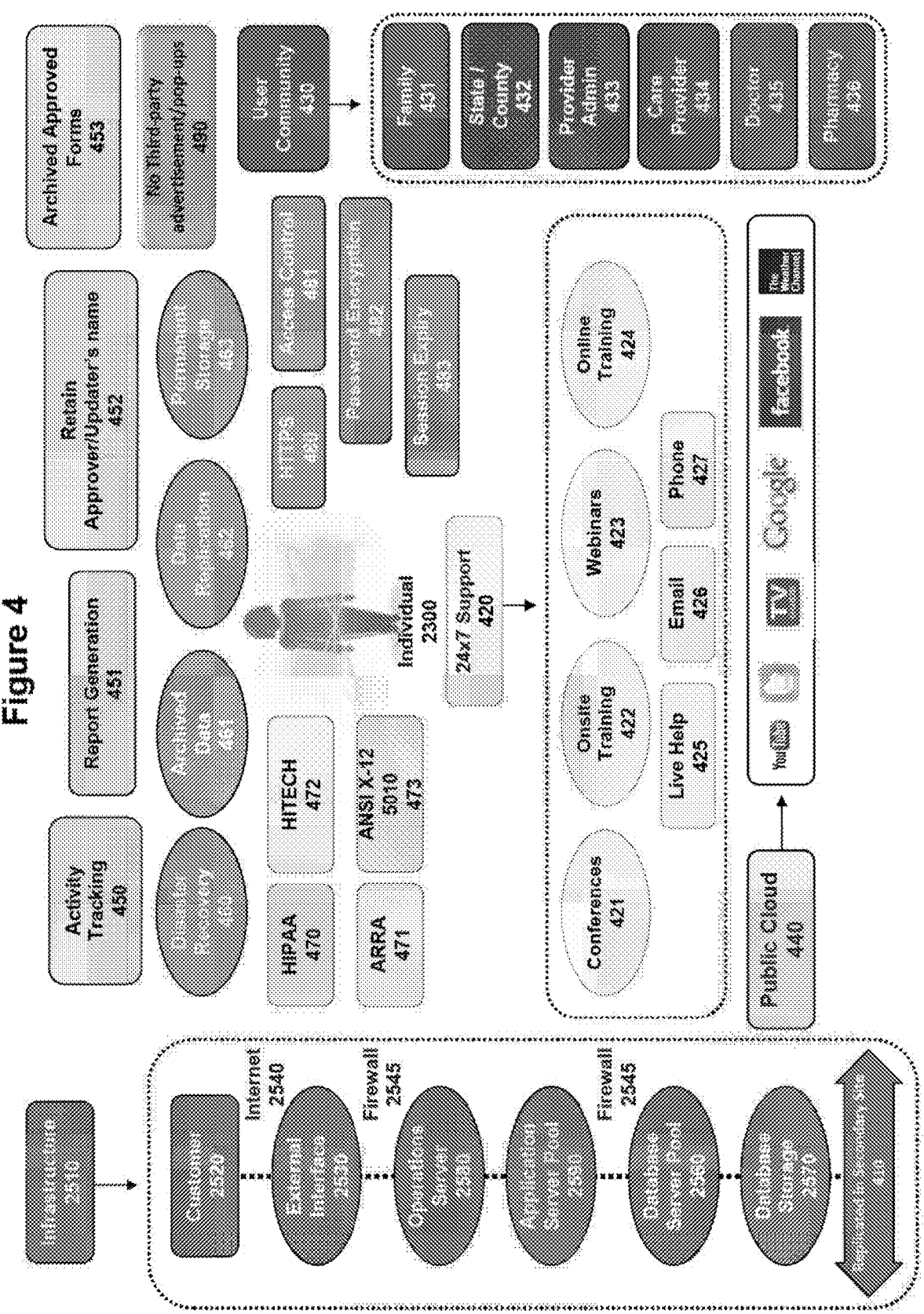
FIG. 4 shows the overview of the system architecture and infrastructure.

FIG. 4 illustrates the overview of the system including the infrastructure and its user community. The Infrastructure 2510 consists of the Customer 2520, External Interface 2530, Internet 2540, Operations Server 2580, Application Server Pool 2590, Database Server Pool 2560, and Database Storage 2570. The system has another secondary site along with the primary site. All data is replicated in secondary site as backup 410. The replicated information in the secondary site can be used to recover data at time of any disaster.

The Public Cloud 440 represents that the system can interact with other public cloud to get the public data. As shown in the figure, the system may use the public data from the YouTube, Twitter, TV Guide, Google, Facebook, Weather Channel, etc. This information can be useful in understanding the individuals better and knowing their preferences. For example, the system may use Twitter, YouTube, Facebook information while generating different queries for the individuals. These queries might be generated to learn about the individuals' preferences which may include favorite celebrities, restaurants, food, movie ratings, TV Programs, etc. The information found from these queries can be useful in determining the supports or teaching methods while preparing the service plans.

The User Community 430 represents the entities that can use the system for individual supports. These entities may include Family 431, State/County 432, Provider Admin 433, Care Provider 434, Doctor 435, and Pharmacy 436. User community 430 may also include staff members, volunteers and anyone else, paid or unpaid, possibly providing private, non-governmental assistance. Data entered by the User Community 430 typically can have time and date stamps and IP addresses for information entered. There can be activity tracking and many other methods of knowing specifically who and where the information is from.

As shown in the FIG. 4, the system has compliance with the HIPAA 470, ARRA 471, HITECH 472, and ANSI X-12 5010473. The system allows users to access the system as long as they have a browser installed which supports HTTPS 480. As security features, the system has Access Control 481, Password Encryption 482 and Session Expiry 483. The users have unique login credentials where the passwords are encrypted. Using these unique login credentials users can access the system. The access control mechanism allows entities to setup the user accounts following the entity preferences. For example, an entity providing support may create a user account for a family member with the view access on the documentation. Family member may be assigned with the view only roles which will not allow them to edit or enter new information. The entity administrator may limit their access to create new documentation. People without appropriate access privileges may now be able to view the Protected Health Information (PHI) of the individuals that is stored in the database, but they cannot edit or enter new data on the individual as they do not have necessary roles to create or edit information. The entities may define a Specific Set of Individual, Program and/or Caseloads 2730 and then assign user accounts with appropriate privileges. The specific abilities to access a certain application for an individual are defined with roles to access such applications 2720.

The architecture of the system has been designed in such a way that it stores all the data permanently in the database 463 so that data is not lost. The Data Replication 462 shows that the system replicates all data to the secondary site as a measurement for Disaster Recovery 460. The system can track each update made to the original data and archive all these changes in the database 461. The system also has the Activity Tracking 450 feature that allows users to track each of the activity made by the users in different applications. The wide varieties of reports can be generated from the system that includes management summaries, multi provider reports, health care reports, and training management reports 451. The system can archive the approved documentation so that it reflects the exact information as it was while approving the document 453. It also retains approver and updaters' names as it was at the time of approving or updating the document 452. The system may also ensure that there are no Third-party advertisements or pop-ups 490.

For the 24 hour/day, 7 day/week (24/7) Support 420 the system can allow support through Conferences 421, Onsite Training 422, Webinars 423, Online Training 424, Email 426, Phone 427 and Live Help 425. This is to provide the User Community 430 with better experience of using the system. For example in the conferences or onsite training, the users may have hands-on experience of learning more about the system. They may get a demo user account for testing purposes so that they can know the details of the system before they pay for it. To provide better customer support webinars or online trainings can be designed for the system as demonstration tools. Users may get in touch with their questions and feedback regarding the applications. The system can also have an automated issue tracker tool that can be used to track users' feedback, complaints or other issues regarding the system.

Cognitive Conditions

Figure 5:
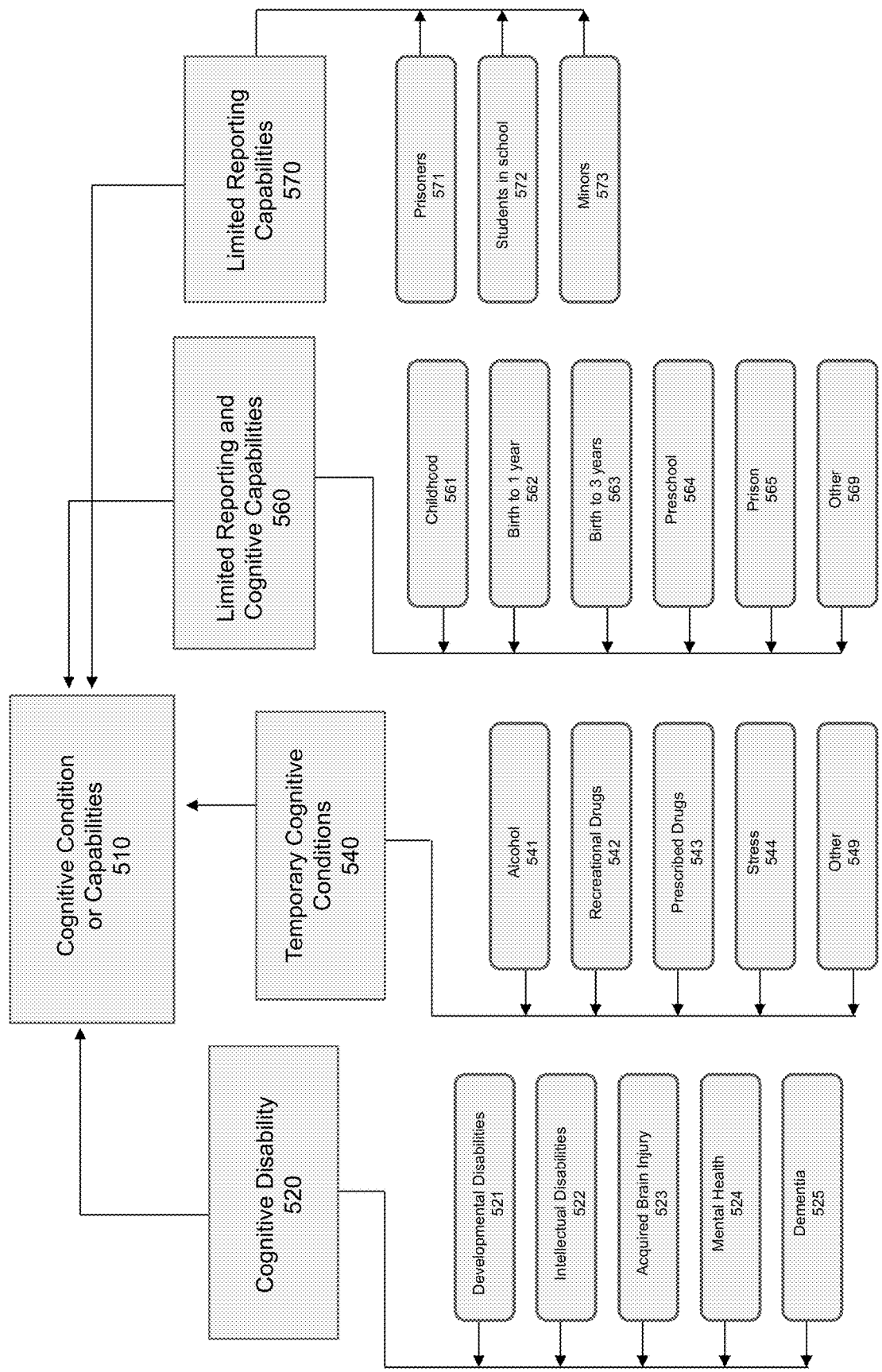
FIG. 5 illustrates an overview of the cognitive conditions.

FIG. 5 illustrates an overview of the cognitive conditions of individuals 510 that could be recognized by the system and analyzed further for interpreting the information conveyed directly by them or by other sources. The system could work for people with temporary and permanent cognitive and intellectual disabilities and impairments, just as it can work for individuals in school, children ages birth to three, and for prisoners. Cognitive Disability 520 could include Intellectual disabilities (including what was formerly called mental retardation) 522, developmental disabilities 521, acquired brain injury/traumatic brain injury 533, neurodegenerative diseases such as dementia 535, mental health 534, Alzheimer's disease, corticobasal degeneration, prion disorders, Parkinson's disease, and multiple system atrophy.

The system could also analyze based on recognition of temporary cognitive disabilities 540 such as from high level of alcohol 541, medical or recreational drugs 542, prescribed drugs 543, stress 544, depression, distraction, tiredness or other more transitory situations 549. In these situations, the type of documentation that either a staff member or an individual can create could be different than usual. The system can determine the difference from the usual pattern since the data on the Individual and staff is already present in the system. The system could recognize this and interpret this information accordingly.

As shown by Limited Reporting and Cognitive Capabilities 560 the system could also be used during parts of Childhood 561 such as Birth to 1 year 562, Birth to 3 years 563 and Preschool 564. The system could also be used for collecting data on individuals who are imprisoned 565 and others 569 living in circumstances when the ability to respond to questions could be limited and may benefit from the enhanced analyses and processes of this system.

As shown by Limited Reporting Capabilities 570, the system can also be used to document cases or allegations of abuse against students in the school system 572 or against animals. It can recognize the limited reporting capabilities of minors 573 and prisoners 571 and meets the documentation and reporting needs of such Individuals.

As shown by Verifying information based on perceived inconsistency 380 the system may use a similar process to save the information and data in multiple input formats and then match that information against previous information and interpretations generated. For example, if an individual had certain indications of having impairment from too much alcohol and also was involved in reporting that an accident or other event had occurred, the system can recognize that there were differences in the condition and intellectual or mental state of the person providing information and may treat that information differently than if there was no indication of heightened level of alcohol. One input to the system could be a breathalyzer or other device to provide data. Other inputs could be a camera providing a picture of how someone was walking and the system can compare with normal regular walking. Another input could be a sound device which can capture differences in the speech patterns of an individual. In these cases, the system (as indicated in System to Reinterpret mapping 390) could compare the pattern with the previous data collected from a single individual, a group or class of individuals or with the general data from the system. Then the system can perform mapping of information as both the old and new information may be available in the system.

Data Reporting

Figure 6:
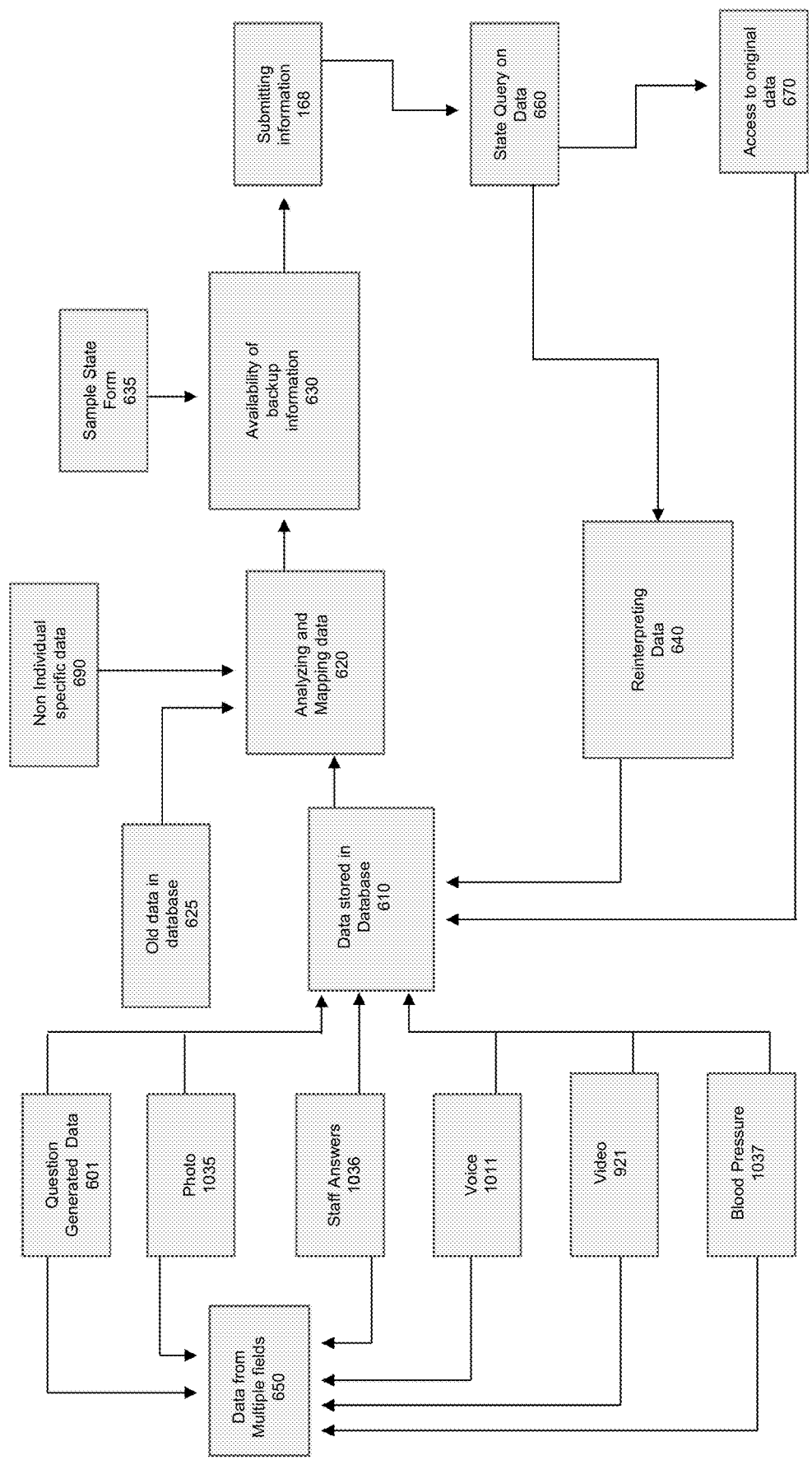
FIG. 6 illustrates an overview of the sample data flow for reporting.

FIG. 6 shows an example of a sample data flow for reporting the information that can be generated from multiple data sources. The Data from Multiple fields 650 shows that data collected can have information from different fields as backup for a single data point. For example, if the individuals were asked if they were happy with the service they were provided, the response and stored data might include an audio recording of their answers, a video of their facial muscles and facial expression and also a simultaneous video of someone else in the room if there was a perception that their response could be influenced by others in the room. The system might interpret that collection of data as a "yes" or "no" or other response, but the raw data would be available to later on change the response from, for example, a "yes I was happy" to a "no I was not happy" while still having and utilizing the original real time documentation. These queries might be asked by a trusted person or staff member on the video or audio.

Each piece of data is also identified in the database by how it was created or collected 610 and stored in the database which can be accessed by the system and staff with necessary caseloads and access privileges on individuals. The system compares individual responses generated from different data fields and analyzes data for mapping 620. While analyzing and mapping the information the system may use the Old Data in Database 625. Old data that is stored in the database can be accessed and compared with the newly gathered information to determine the best possible match to interpret the individual responses. This may help track the changes in responses from the same individual. If there are any changes in the response the system may need to generate queries to find out the reason behind these changes. The system may also use Non-Individual specific data 690 to analyze the information. Using the Public Cloud 440 the system may get information from external sources which can be used mapped to the individual responses. For example, if the system collects the individual response that the individual was not happy then the system can look into the public data to search for the information that might be causing this negative response. The system might find from the internet that a plane has been crashed on the day when data has been collected. In such a case, the system can analyze this information further to find out if this is the reason that has caused this response. The system may generate more queries that might be needed to analyze this information.

After the mapping and analysis is done, the system stores the all the backup information and the interpreted information in the database 630. While analyzing the responses received from the individuals the system always stores the original responses as backup information. This backup information might be used if need arises for remapping and reanalyzing of the responses. The system has the Sample State Form 635 where the data points have been designed according to the state requirements. The system interpreted responses are also mapped to the appropriate data points on the sample state forms. These forms that are filled by the system can be submitted as per the requirements of funding agencies or government jurisdictions 168. The system may reinterpret the mapping of data based on the information available while keeping access to the original data 640.

A state director or state head of nursing or other senior positions which have access to data across organizations may want the ability to analyze the data. With this system the analysis would be possible in a reduced amount of time, utilizing resources in an efficient way and in a manner consistent with maintaining the privacy of data and respect for the individuals. In the system, the caseloads and super roles can be defined for each different type of users as identified in the User Community 430. An example is that a caseload could have access to individual A, or to individual A and Individual B, or everyone living at a home. A super role might be defined for a nurse to enter and edit nursing information or an executive director to see all information or a family member to view information about their family member. Therefore a nurse with a caseload of individual A might only see and be able to edit and enter medical information regarding Individual A, while an executive director might have a caseload for Individual A and Individual B and could have a range of permissions, including everything the Nurse for Individual A had.

By the system performing the analysis with caseloads and super roles, it is possible to determine information including fraud, abuse and neglect, and other types of objectives. As discussed in U.S. Pat. No. 8,281,370, Caseloads are the specific set of information that defines what individual or program a user can have access to. Super roles are referred as the privilege that a user needs in order to access a particular application within the system. The documentation can include the information on caseloads and super roles, discussed in U.S. Pat. No. 8,281,370, including but not limited to the discussion Col. 4, line 64—col. 5, line 60, and Col. 12, line 62—Col. 15, line 3.

Analyzing the Caseloads, the system can identify the users who should have access to which set of individuals and programs. Further analysis on the roles for each set of Caseloads can be done by the system to determine whether the users were documenting their services using appropriate applications or not. This analysis can be useful for auditing to look for any fraud or missing date when data was not entered by the staff. Since the system can gather information directly from the individuals or by using non person-centered data specific to the individual or the situation, the system can always run such analysis and provide the state or funding agencies with appropriate interpretation. The state may require collecting data from individuals for verification of proper service delivery, identification and prevention of fraud, abuse and neglect determination and to meet billing and funding requirements 660. This information can also be generated by the system and provided to the state.

As shown in Reinterpreting Data 640, the system can reinterpret data if needed depending on the responses received from an individual. The system gathers data specific to an individual from multiple data sources. If the system identifies that there is not enough person-centered data for analysis, then the system may analyze data received from the family, guardian or other staff providing services to the individual or make some assumptions based on the Non Person-Centered Data 306. For example, while an individual is on a visit to his/her family, the system might not have the video recording or other type of person-centered data on whether the individual is taking his or her medications at scheduled times. The system may look into other data sources for data on the individual's taking medications. The system may have the data collected from family saying that they gave medicine to the individual and thus the system may analyze data from multiple sources and reinterpret if needed. As the initial interpretation can be inappropriate, the system may reinterpret when it becomes aware that there is a new information or new data related to the individual or the particular situation. There could be automated analysis going on, where the system looks for broader correlations and changes in assumptions, patterns, regressions and correlations. A reinterpretation could occur automatically or randomly as the computer is processing large amounts of data. The system then starts narrowing down information based on other information and make necessary reinterpretations. The responses may vary depending on the responses directly from an individual or the responses received from staff or provider agencies or from monitoring individuals through external devices. Previous responses are stored into the system and matched with the new information collected and interpretation may be changed on the basis of the mapping of information. The original raw data stored in the database may be accessible to the system having proper caseloads and to the staff with necessary privileges 670.

Information Collection

To determine the response for a single data point the system can use a number of modes to get the information. Information can be collected in the form of a question based approach and related response as shown in the Question Generated Data 601. Examples of methods to ask questions could be a person asking a question, a system or other device asking a question, multiple people asking a question or having a discussion to illicit information, asking a question using braille, tactile, video, system, telephone, voice, audio, pictures, and other approaches where a direct question-can be asked. Even though the system may determine that the answer may or may not match what it appears to be, the method of collecting data is considered to be a direct question and answer method. The system may document how the question is asked and answered in addition to the answer and method of answering as shown in FIG. 9. Another way that information can be obtained is through general monitoring of a situation or location. These modes may include video 921, audio 922, pictures 923, text 924, real time video 925, uploaded video 926, monitoring cameras such as implanted, mobile and fixed monitoring and sensitive devices 927, over cellphone or other wireless device 930, braille 934 to assist the visually impaired, tactile systems 935, electromechanical sensors 936, body temperature and chemical sensors 937, audio capture system 938 or other modes which may capture information directly from an individual to be used as general surveillance. The system may also use any combination of multiple items from this list.

The system interfaces with external devices such as monitoring cameras to take photos of individuals on interval basis 1035. This may help in monitoring the activities of an individual, behavior exhibited on regular intervals, expressions and attitude. System may also record answers of staff responsible for taking care of individuals using different approaches as shown in 1036. Answers from staff can be generated using a question based approach or monitoring their activities through external devices. Staffs may be prompted to answer under different situations and the same question may be asked to multiple staff members. The responses can then be recorded by the system and compared with the previous responses. Audio of an Individual can be captured 1011 and analyzed by the system by comparing the responses with the other audio from the same individual or other individuals in the system. This may record the voice of an individual, loudness of their speech, variation in tone or the tremble in their voice on interval basis. The system can interpret these voice recordings and provide reinterpretation in mapping information.

Information from an individual can be received by capturing video. This video 921 may provide information to the system regarding the movement of the individuals and any other hidden information which the individual is unable to convey through direct communication. For example, there could be a distinction between Real Time Video 925 and Uploaded Video 926. Video which was uploaded after it was taken could have a higher probability of being altered or manipulated. In addition uploaded video might be one of a series of videos which were taken or only a subset that has been added to the database. This presents a different requirement for interpretation than video which was taken in real time when reviewing how to interpret a response from an individual with cognitive disabilities.

The information can also be generated from the Blood Pressure 1037 of an individual. It can be collected by monitoring the individual on interval basis. The data can also be compared with the regular blood pressure of the individual to determine if there is any deviation.

Another method of generating information is creating changes in the environment and observing the response of an individual. For example, understanding how a particular individual is reacting to changes in sounds 931, visuals 932, crowds, light, temperature and weather. Additional methods of capturing data or gathering information include electrochemical sensors 936, body worn sensors 937. These can monitor the changes in body temperature and the presence of any toxic gases in the environment. As the system can generate analysis in real time 135 and adjust questions in real time 155 without human beings seeing data and reviewing data. Thus, additional questions and information can be created in a faster manner which can allow more useful real time information generation.

Figure 20:
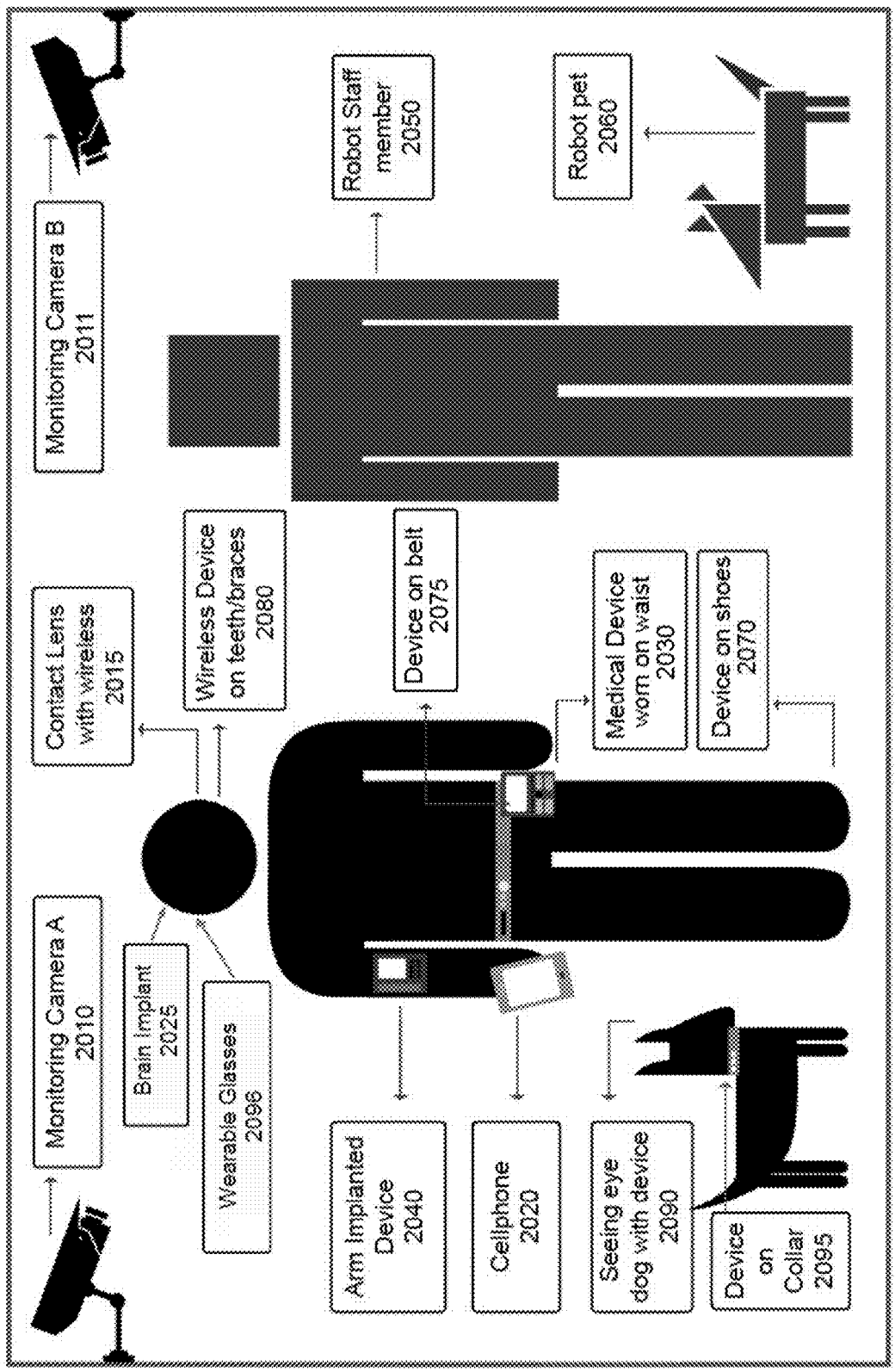
FIG. 20 shows the variety of options that can be used to obtain data from the individuals.

FIG. 20 illustrates ways of collecting data from an Individual with disabilities. Information can be collected from Individuals directly by implanting various devices within an Individual or from the devices in the surrounding of the Individual, all of which transmit information wirelessly to the system. This helps in collecting information directly from the Individual and where the information is free from any kind of manipulation. Information can be collected from devices such as small chips implanted in the brain 2025 which collect information from the neurological responses. These are messages receiving "information" from various body tissues via the sensory nerves, or those initiating the function of other tissues such as organs, muscles, etc. Information can also be received by the system from the devices in the contact lens 2015 and wearable glasses 2096 which enable the system to know what the individual is viewing and can analyze the data in the surrounding of the individual. There may also be multiple monitoring cameras in the room 2010, 2011 to capture information from different angles. There may be devices in the braces of the Individual 2080 to identify the food which is being taken, measure the body temperature of the individual as well as the temperature of the food being eaten, analyze the stress taken by the individual while chewing the food and the breathe of the individual. There can be an Arm Implanted Device 2040 which provides information regarding the movement of the arm of an individual. The system stores data in the database, analyzes information regarding the intent or reaction of the individual during the occurrence of an event, and determines the health condition of the Individual.

Data can also be collected from wireless devices carried or worn by an individual. There can be cellphones 2020 carried by the individual which record information regarding who contacted the individual, voice tone of the individual while communicating with different people over the phone, information on what was being said to the individual and the reaction of the individual to statements, all of which can be collected and transmitted to the system. Medical devices can be worn on waist 2030, devices on shoes 2070 and belt 2075, all of which detail information regarding the movement of the individual.

There can be other devices in the surroundings of the Individual such as Robot Staff member 2050, Robot Pet 2060, and Seeing eye dog 2090 with device on the collar 2095 that may continuously capture data on the movement, facial expression and activities performed by the individual and feed the information into the system. Robot staff or robot pet are external devices that collect data on Individuals and feeds the information into the system for further analysis.

Figure 21:
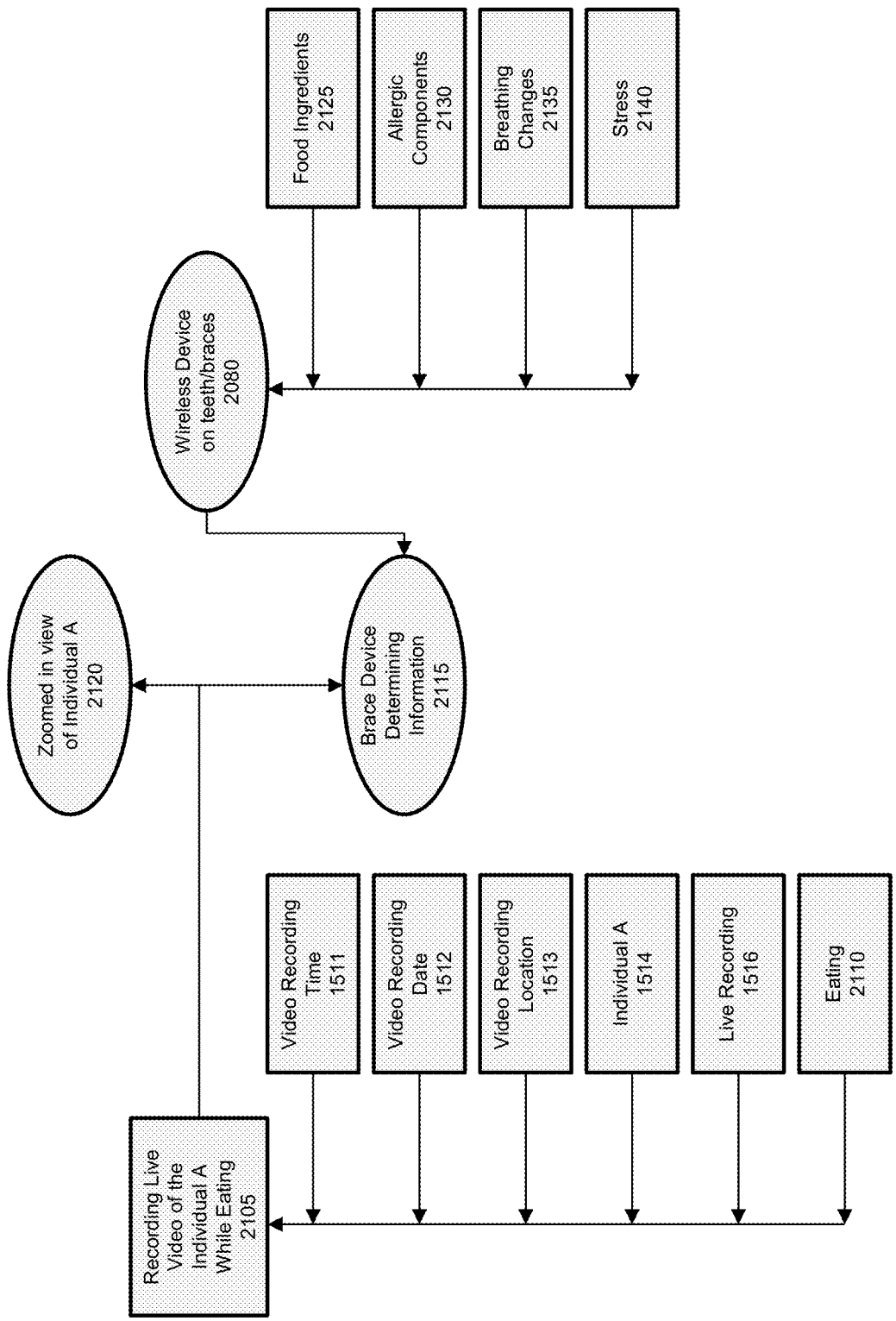
FIG. 21 illustrates an example of a device implanted in braces to generate information.

FIG. 21 illustrates an example of a device implanted in braces to generate information. The system may record the live video of when the Individual A with a devices implanted on braces is eating 2105. The system may use the monitoring camera to capture the video including the Video Recording Time 1511, Video Recording Date 1512, Video Recording Location 1513 as dining room. The system may capture the information about the food items and also facial expression of the Individual at the time of eating or chewing the food. To obtain the information about the facial expression the system may automatically capture the Zoomed in view of Individual A 2120. This information can be useful to determine whether the individual likes the food or not. The system can also compare the expressions of the Individual to determine the likes and dislikes of the Individual. While eating the food, the wireless device on braces 2080 can determine the Food Ingredients 2125, Allergic Components 2130. System may analyze this information and compare the diet and allergy information of the individual already stored in the system with the food being eaten by the Individual. The device can also provide the information about the changes in breathing 2135, body temperature and stress 2140. The system may provide notifications to staff once it detects the allergy interaction of a certain food being taken by the Individual or take preventive measures immediately. It might also check the dietary requirements of the Individual and compare it with the ingredients of the food and notify staff or take possible measures. It may also record the dietary information of the food being taken and store it in the Individual's file in the database.

Figure 21A:
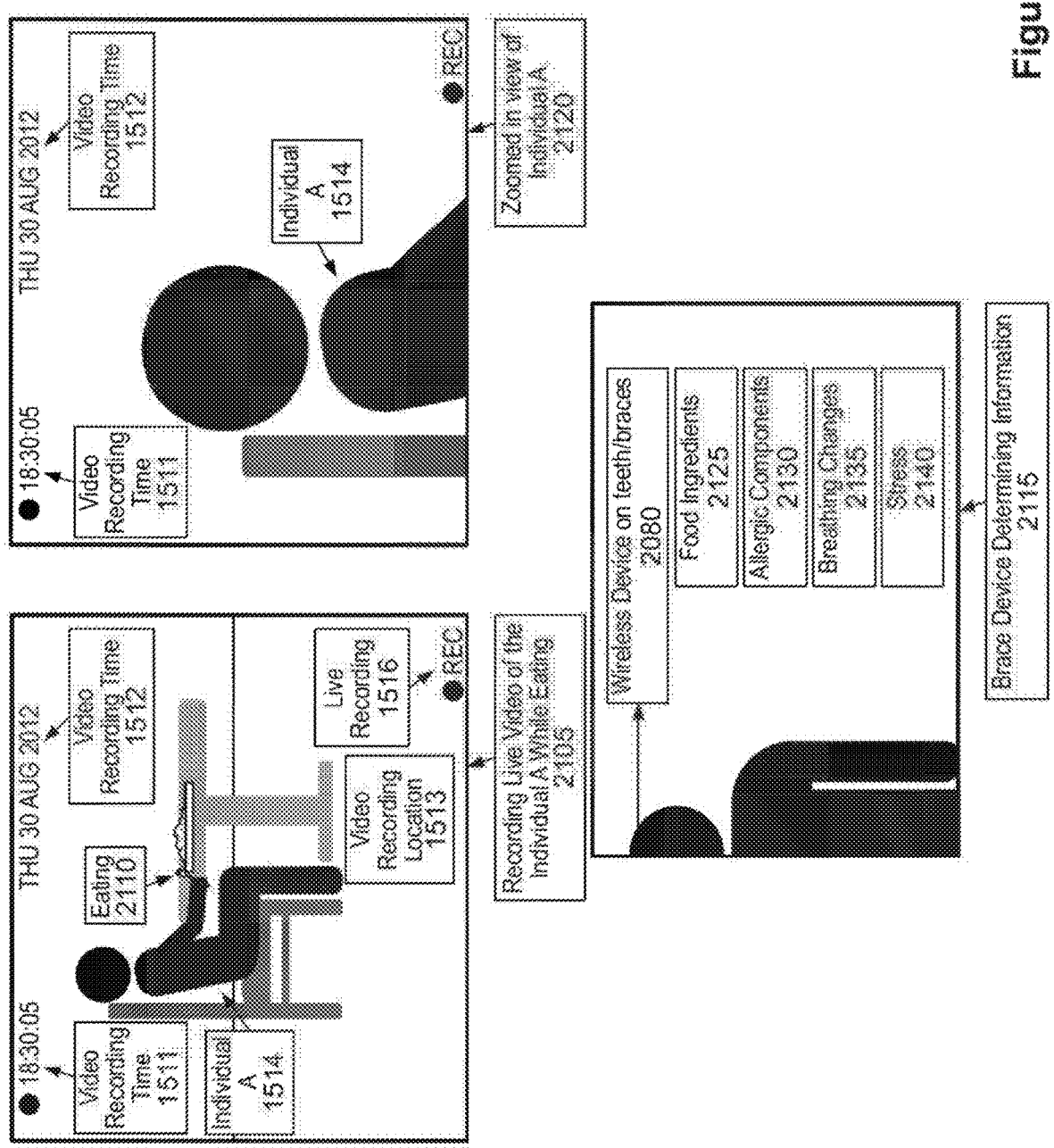
FIG. 21a represents the sample video recording of an individual wearing wireless brace devices at the time eating and the sample screenshot where the system can analyze the information generated by the implanted brace device.

In FIG. 21*a* the Recording Live Video of the Individual A While Eating 2105 shows that the system is recording the live video when the individual was eating in the dining room. The system captures the raw view of the Individual A 1514, Video Recording Time 1511, Video Recording Date 1512, Video Recording Location 1513, and the activity of Individual A as Eating 2110. The Zoomed in view of Individual A 2120 can be used to determine the facial expressions. The sample screenshot of the Brace Device Determining Information 2115 represents that while eating food the brace device can determine the Food Ingredients 2125, Allergic Components 2130, Breathing Changes 2135, Stress 2140.

Detected Undesirable Outcomes

Figure 7:
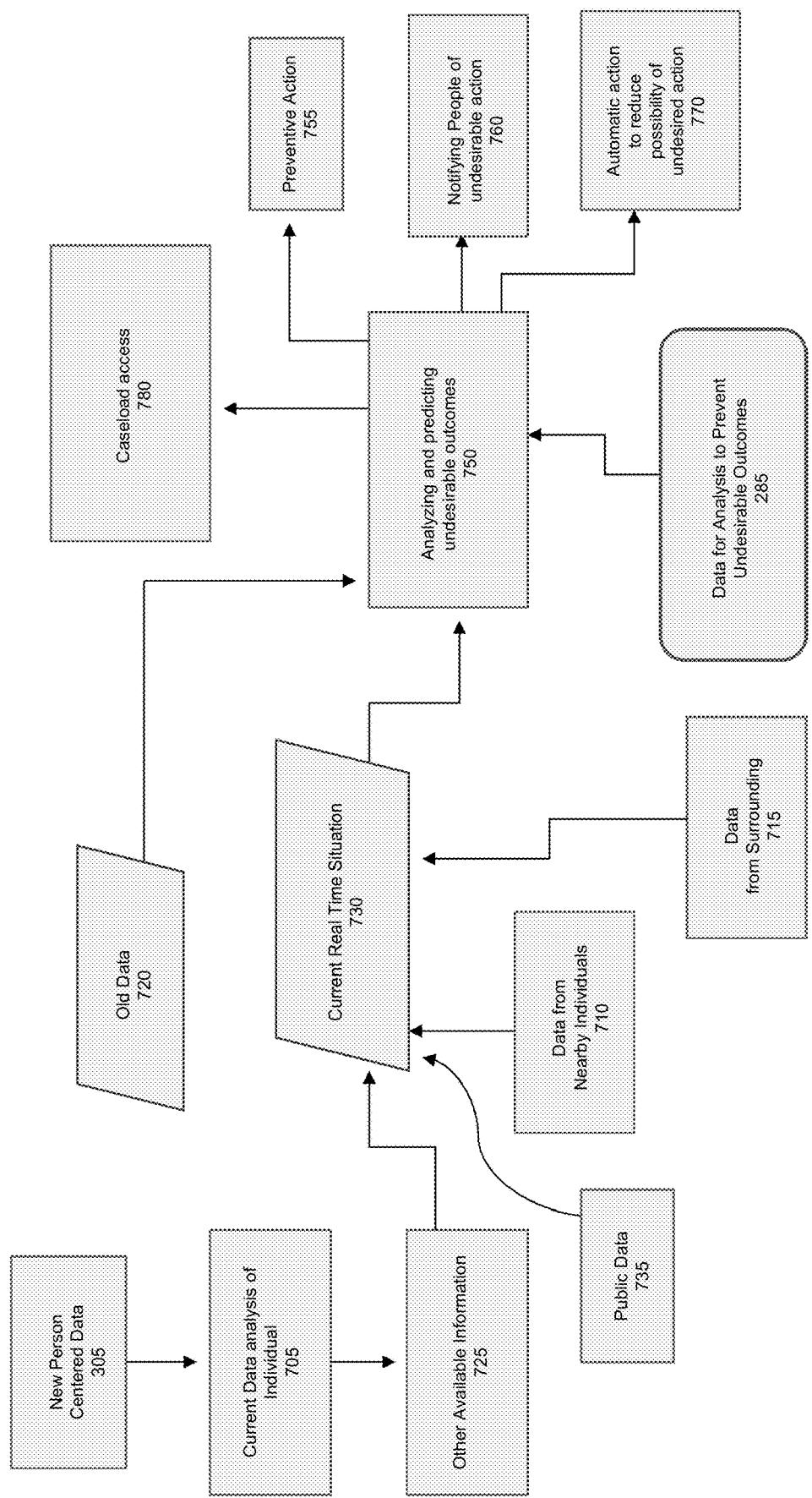
FIG. 7 illustrates an overview on the detection and prevention of undesirable outcomes.

FIG. 7 illustrate an overview on the detection and prevention of undesirable outcomes. The system collects and analyzes information that it receives from the current real time situation 730 as well as analyzes information already stored in the database 720. The Current real-time data can be retrieved from individuals within a close reach (data from nearby Individuals 710) of the individual who is being monitored, from the surroundings and location the individual was in (Data from Surrounding 715), other information retrieved from external or internal devices (Other Available Information 725) as well as from staff looking after the individual and staff surrounding the individual (Public data 735) for further analysis and interpretation of data (Current Data analysis of Individual 705). In fact, if a system determines, as shown in analyzing and predicting undesirable outcomes 750 that a possible abuse and neglect situation or a risk could be occurring or might occur based on the data and analysis available to the system caseload, the system can take immediate actions. These actions might include both alert appropriate persons through a notification system that a problem might be occurring (Notifying people of undesirable action 760), as well as cause them to take preventive actions 755 by changing the immediate environment of the individual who is at risk of being abused or neglected or in the environment of a person who might be creating a situation of abuse and neglect (Automatically Generated Measures 770).

The system could have a predetermined list of undesirable outcomes that has to be prevented due to the occurrence of an undesirable event as shown in Data for Undesirable Outcomes 275. One list could be for General or Societal Undesirable Outcomes 1110 which include Abuse 291, Neglect 292, Incident 293, Injury 294, Rape 295, Molestation 299, Client to Client Altercation 298 or Other Undesirable Outcomes 296. Another type of undesirable outcome could be a Person-Centered Undesirable Outcome 1130 which can be determined by using the System Interpreting Data 310 and Proof of Positive or Negative Individual Satisfaction 215. One example of a person-centered undesirable outcome would be if there a staff member who has a history of abusing people, there could be a societal goal of stopping staff who are causing injury or neglect from dealing with individuals in the future. A rape would also constitute a person-centered undesirable outcome. A person-centered undesirable outcome could also be going to a loud party with lots of noise. Many people might enjoy going to a loud party at a nightclub. But for someone with Autism or other diagnosed conditions it could create other predictable problems—beyond just not enjoying the noise.

While collecting data directly from the individuals, the system may determine that the individual is not happy with a particular service or something around the individual was causing disturbance to the individual at that time. In such cases, the individual might react negatively (could be self injurious also) or may cause negative impact on the individual. Such undesirable person-centered outcomes can be determined by the system. The list of Undesirable outcomes may also include Entity Providing Support Based Undesirable Outcome 1150, Other Individual 1190 or Property related 1170 undesirable outcomes. For example, an agency might be concerned that staff member was using more expensive materials for an arts and crafts project. There is no negative effect to the individual, but there are funds wasted which is undesirable for the Entity Providing Support 250. Other examples of non-person centered undesirable outcomes could involve misuse of resources or wasting time of staff when there was no benefit to an individual or person receiving services or funding.

If any change is observed in the regular activities of an individual by monitoring external devices such as video 921, audio 922, pictures 923 and monitoring cameras 927 then those changes can be analyzed and interpreted by the system. These responses can be compared with the existing data in the system to identify the changes which may lead to the detection of undesirable actions.

Once an undesirable outcome is detected, the system can take necessary measures. The system could have access 770 to devices which could alert people of possible problems. This could include the ability to create noise, sounds, smoke, alarms, fire alarm, smells, vibrations, and different kinds of lights whose intensity is determined by the type of abuse and neglect identified by the system. This could be visible or noticeable to either just the people potentially involved or to the additional people in the area. The system could also cause certain controls to change. For example, doors could automatically lock, access to rooms or situations could change, water barriers could be created, and others. Many of these changes are part of smart homes, automated homes, robots and other security and remote accessing. An innovation here is that the smart home or automation can be triggered by automated observances of an individual with cognitive disabilities even if the person is giving a response which might indicate everything is alright or which previously might have indicated that everything was alright.

Smart homes or automated assistive electrical home appliances and services can be designed for the individuals. The smart home can have intelligent communication network that can connect the key electrical appliances and allow the system to remotely control or manage appliances or the ambiances based on different situations. For example, if there is any loud noise outside which may cause disturbance to the individuals, then the system can communicate with the sound system of the house to play music to change the ambiance and to prevent any undesirable event. If the controller can be integrated with the caseloads based on the individuals attending an event, Caseload Access 780, the controller might be able to ascertain what environments or situations were least likely to trigger behavioral or other types of incidents or events from individuals in the room. In case of multiple individuals being in the place and having the same stimuli, having a system with a caseload of multiple individuals who might be in the same situation could be useful.

Another method of transmitting data to and from individuals is either a wearable device 2070, 2075 or an implanted device or chip 2025, 2040 inside an individual's body. The appropriate regulations might need to be followed for approval and ability to implant a device. The device could be designed to connect directly to a wireless device which could then access the system. This device could send information about how an individual perceives a situation as well as changes to body chemistry and internal systems. The device could also have access to certain psychological information. It is possible that the device could have information which is either not able to be communicated by the individual or which the individual could not be aware of.

In cases where the system can monitor data either internal to an individual or external to an individual, the system could be aware of the heightened possibility of an individual to individual altercation or event. The system might be able to attempt to stop such an event in several ways including sending impulses or other information to the wearable or implanted devices within an individual, notifying individuals working or in the vicinity of the individuals, sending information and changing aspects of the environment such as locking doors, changing music, changing lighting, and other external stimuli as indicated in Automatically Generated Measures 770.

When requirements or data includes audio 922 or video 921 or monitoring cameras 927 or other modes other than words or numbers, there is a possibility that the audio or video may include information from more than one individual. For example, if a picture is taken then there could be other individuals in the background or other parts of the picture. If a video is taken then there could be other individuals in the background or other parts of all or part of the video. These pictures or video could be of other individuals who could be subject to HIPAA, privacy, or other future regulatory or societal privacy restrictions.

The system could have the capability to redact, delete, change, morph, or otherwise adjust the information included in individual A's file while maintaining the original raw information in the system. As the system can know who has what caseloads as indicated in Caseload Access 780, the system could permit staff and other appropriate people to see information based on their caseloads.

The system may have the capability to limit access to the video with an appropriate note that information related to a particular individual was being withheld to provide protection to another individual in the video. Appropriate staff or oversight agencies could be made aware of this action and determination. Information in audio or video files can also be shown after removing or blurring individual beyond recognition to staff who do not have caseload access on them.

System may provide data access to auditors or surveyors as original information is stored in the system. An example could be that a video or audio is used for proof of service delivery or needed to show that reimbursement should be made or a service was delivered for individual A. If that video had information regarding an individual other than Individual A, then the system could note that additional information is available to an auditor or surveyor.

Analyzing Information Collected from Individuals

Figure 8:
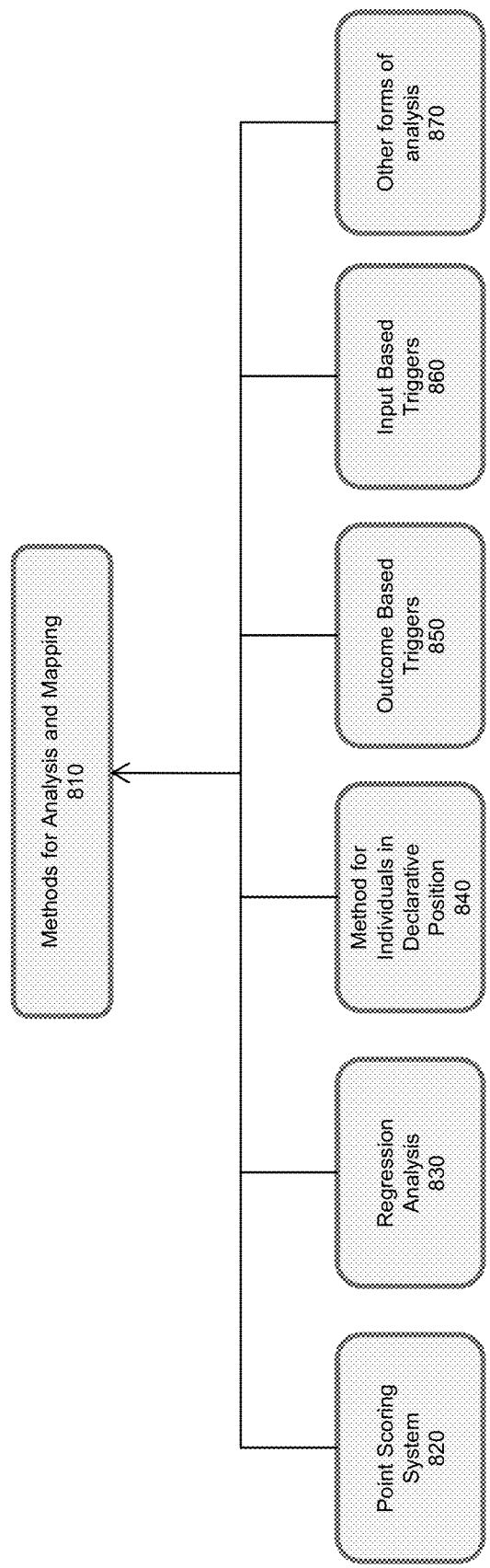
FIG. 8 illustrates the process of determining the methods to analyze, map or use predictions for the input information.
Figure 9:
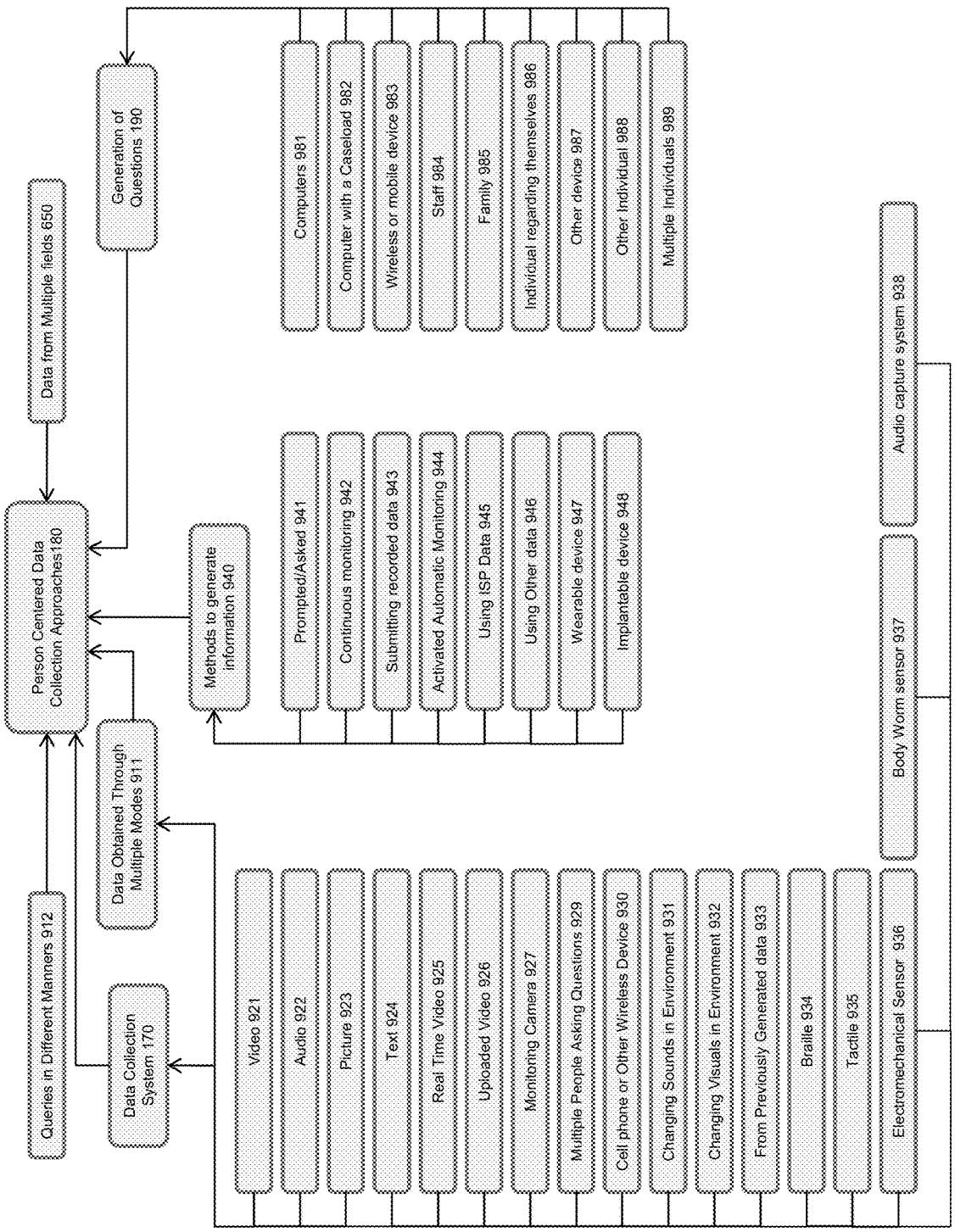
FIG. 9 illustrates how the system can generate queries and collect information.

FIG. 8 illustrates embodiments of the system that determines the methods to analyze, map or use predictions for the information collected from the individuals. The Point Scoring System 820 is one of the methods that can be used for analysis, mapping or making predictions. While generating information for individuals' responses, the system determines a score for each response following a scoring method. The system may generate the score for each responses or data received in various format including Voice 1011, Facial Expressions 1012, Hand Movements 1013, Words 1014, Biometrics 1015, Typing/Keystrokes 1016, Individual Tics 1017, Sounds 1018, Touch 1019, Typing Speed 1020, Typing Pattern 1021, Change in Stress Level 1022, Change in Blood Pressure 1023, Smell 1024, Change in Smell 1025, Sweat 1026, Change in Pulse 1027, Pulse 1028, Temperature 1029, Electrochemical Modification 1030, Other actions from an Individual 1031, Facial Movements 1032, Body Movements 1033, Body Chemistry 1034, Photo 1035, Staff Answers 1036, or Blood Pressure 1037. For example, interpreting the facial expressions, hand and body movements the system may determine that the individual is participating in a task with full physical prompt. The system then may put the appropriate score for this response. If the individual is not participating in a task and is instead denying, then the system might put a lower score than before. Analyzing these two different points for a same task the system could map to other data to find out what might be the reason for lower points. The system may also automatically trigger responses that the staff may follow while explaining the task next time for better outcomes.

The Regression Analysis 830 may be used for analysis or mapping individuals' responses. An individual's responses to the same questions may vary depending on the surroundings or the presence of the people. In such cases, regression analysis can be used to help the system predict or assume the outcomes from individuals' responses. Many controllers are designed to generate queries to learn about individuals' preferences. For example, individuals can be asked what music they prefer, what colors they prefer and so forth. However in cases of people with cognitive disabilities they might not be able to express their preferences. And they could be more likely to have some sort of event. By tracking different situations where an individual reacted to different stimuli including sound, noise, crowds, light, temperature and visuals, the system may have data to predict how an individual might react. Combining that information with other information on separate individuals might lead to better outcomes by basing activities, sounds, music, visuals and graphics used to generate the person-centered information.

The same questions determined for a particular situation could be asked to a number of individuals. For example, the individuals can be asked questions in the presence of loud noise and the system could monitor their reactions. Some individuals might react in a similar way, some individuals might not react at all and others might have various negative reactions due the loud noise. The system may store all the responses collected from the individuals with a score assigned to each. Using predetermined algorithm the system could predict that there might have been a certain number of possible outcomes such as hearing impairment, increase in stress, heart beat or the level of depression in the presence of loud noise. Then the system may remap all individuals' responses to these possible outcomes and also compare with their person-centered information. This analysis could help the system recognize the possible incidents that may occur due to loud noise and decide the preventive measures to be taken for individuals with various kinds of intellectual and cognitive disabilities. This information can also be helpful in times of future analysis.

The system may analyze information in a different manner when the individuals are in declarative positions at the time of collecting information 840. The system collects the information from the individuals' declarative statements and may use this information to map with previous records to analyze. Comparing the previous records the system may predict the individuals' preferences. The system can determine if the declarative is coerced, distorted or otherwise not what it seems to be. The individual might state that he/she would like to learn cooking and the system can remap this statement with individual's goals and objective data present within the system. If the previous history does not match with the current declarative statement then the system may analyze the current situation and remap to determine the cause that if the declarative is forced or distorted. Sometimes, it might be the case the statement means something different, not what it seems to be. In that case the system might reanalyze the information to get the actual information.

By having access to significant amounts of person-centered and person created data, the system can analyze and determine the outcomes based approaches that can be used to provide real time guidance and assistance. This system may use the method based on Outcome Based Triggers 850. The possible example of outcome based triggers could be for the individuals with the objective to learn cooking. As soon as the system identifies the objective the system could analyze on the individual's person-centered information to determine the data fields to get detailed information about the individual that might help the individual learn cooking. For example, the individual might love to eat sandwiches and to have extra spices in the food. Using this information the system may send this message to the staff members who will be supporting the individual for learning cooking. This might assist the staff to determine the teaching strategy that can be used to achieve this goal by increasing the individual's interest to learn cooking. In this way the system may analyze the information to trigger outcome based responses.

Another method that the system may use is the Input Based Triggers 860. While capturing information directly from the individual the system might analyze the information to recognize the possible outcomes that this input may lead to. If there is any potential negative or undesirable outcome detected, the system may trigger real time responses that could help the staff to prevent such undesirable outcomes. Likewise, if the system detects that a certain action or environmental change would be necessary to help an individual achieve their goals, a signal could be triggered for a response to help that individual. For example, an individual may express that he/she would like to have chocolate that would make him/her happy. Analyzing this input information the system could identify that it could lead to a positive outcome that might increase the individual's level of satisfaction. However, the system might remap and reinterpret to determine if there is any other possible outcome that may affect the individual negatively based on this input information. For example, eating chocolates may cause tooth decay and the system has previous information about the individual's dental diagnosis. In such a case, the system could trigger responses to notify the staff about the possible negative outcomes that has been derived based on the input information. The staff might then decide to not allow eating chocolates or take necessary steps like brushing after eating chocolates as suggested by the dentist who diagnosed the individual's dental conditions. Such input based analysis could help staff to get real time guidance about handling undesirable outcomes.

There might be some other forms of analysis as shown in 870. The ability to combine information gathered by caseloads on different people in the same situation combined with outside information might help reduce problems in many situations. For example, two or more individuals were in a van and an external data source such as a traffic monitor, a wireless device, a website, a person calling in data, or other source can gather information on the individuals. The external data source might recognize that there was unexpected traffic, the system could determine who was in the van and notify the staff or the vehicle directly based on an analysis of who was in the car. For example, if the system knew that a certain individual did not react well to over a certain amount of period in the car, it might notify someone to get the person to a park or location off the road, while another person might benefit from a certain type of music being played.

The Point Scoring System 820, Regression Analysis 830, Method for Individuals in Declarative Position 840, Outcome Based Triggers 850, Input Based Triggers 860 and other forms of analysis 870 form the set of techniques for the system to analyze, map or use prediction as shown in Methods for Analysis and Mapping 810.

FIG. 9 illustrates how the system collects information by asking questions or gathering information using a wide variety of modes. The Data Collection System 170 determines the methods to be used to generate queries using multiple modes. The Data Obtained through Multiple Modes 911 determines the methods to be used to obtain information from multiple modes of the queries. The queries can be generated in different manners depending on who the individual was with, where the individual was and what the current cognitive state was at the time of data collection (912). The system may obtain data from multiple fields for a single data point 650.

The system may use one or more modes as determined in the Person-Centered Data Collection Approaches 180. The various modes that can be used for individuals with intellectual or cognitive disabilities include Video 921, Audio 922, Picture 923, Text 924, Real Time Video 925, Uploaded Video 926, Monitoring Cameras 927, Person Asking Questions 928, Multiple People Asking Questions 929, Over Cellphone or other Wireless Device 930, Changing Sounds in Environment 931, Changing Visuals in Devices 932, Previously Generated Data 933, Braille 934, Tactile 935, Electromechanical Sensors 936, Body Worn sensors 937, Audio Capture system 938.

The Methods to Generate Information 940 represents that the system receives information either by prompting or asking questions 941, monitoring the individual continuously using any of the modes described in 942. The information could also be found from previous records 943. For example, the system may record an event as video or audio clip and then submit a report on this later. The system could map the report with the original record and analyze as necessary to generate the information.

The system may also activate automatic monitoring based on triggering parameters present in the surroundings 944. The possible example could be analyzing an individual's reaction in the presence of a crowd; the system may configure the triggers to capture video when there are more than 5 people within the surroundings of the individual. The system could then analyze, based on the facial expression or body movements in the presence of other people and could predict the steps the system may take to support the individual in such cases.

Figure 22:
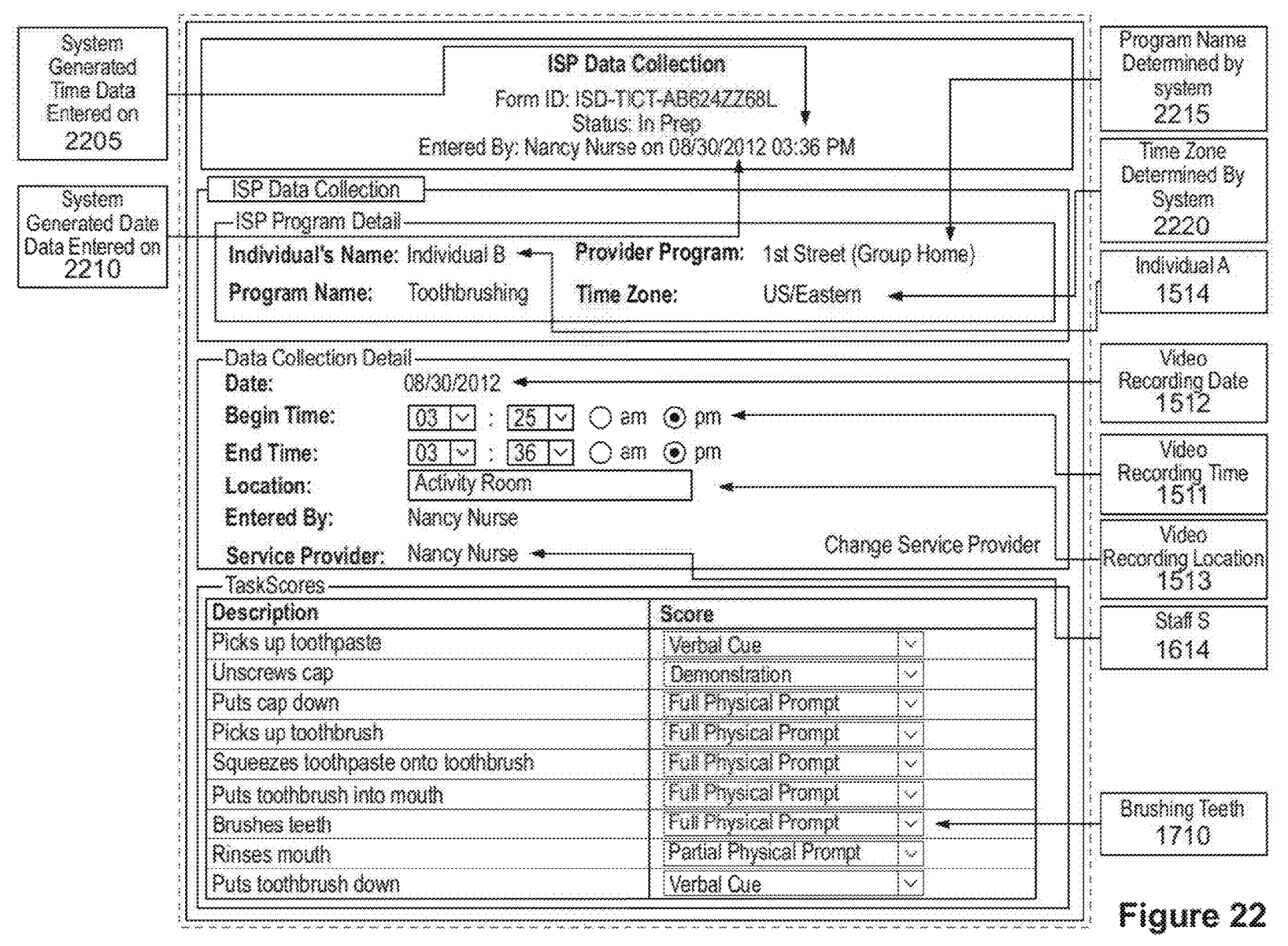

Individual Service Plan (ISP) application can be used to define goals and objectives for programs designed to help individuals and provide guidelines to be followed to achieve those objectives. The ISP application also provides the means to collect and record data to track progress of goals set in the Service/Program Plan as shown in FIG. 22. Once necessary data has been collected, the application calculates their corresponding scores according to the scoring method specified in the ISP and compares them with the baseline scores. The system can get information directly from individuals and provide that information to fill in the ISP Data form. This direct method of collecting information to track the progress of Individuals to achieve their goals removes the possibilities of any fraud or false information being recorded into the system. Besides, the system allows staff to collect ISP data and compares the information collected from Individuals directly and accurately fill out the ISP data form. This method of data collection gets the information to analyze, map, or predict the individual's goals and also determine the support required to meet the goals 945. Using the scores or responses collected in the ISP data the system may analyze an individual's preferences for each goal and could determine possible outcome for the future. This information might be used for modifying the supports according to individuals' or funding agency preferences.

Wearable Devices 947 is another method to collect data which may be used to get real time information remotely, as well as collect data from individuals directly and do further analysis. For example, an individual may go outside the program for a family visit or a vacation or for some event for an extended period of time. During this stay outside of the program, medication needs to be administered to individuals as per the schedule. Wearing an electronic device that can provide medication to the Individual and feed in the feedback from the Individual into the system can ensure proper monitoring of administration of medication of the Individual even outside the program.

Another approach to collect information is to use Implantable Devices 948. The appropriate regulation would have to be followed for approval and ability to implant a device. The device could be designed to connect directly to a wireless device which could then access the system. This device could transmit information about how an individual reacts to a particular situation as well as changes to body temperature, pressure and other symptoms. The device could also have access to certain psychological information. It is possible that the device could have information which is either not able to be communicated by the individual or which the individual could not be aware of. The system can have other data collected from the individual's family, guardian or involved staff members 946. This information might help the system for analysis or mapping.

The questions asked to an individual could be generated using Computer 981 which is a processing unit that can determine the queries to be asked to the individuals. The Computer with a Caseload 982 represents the processing unit with a certain set of abilities on a specific set of individuals and/or programs that can generate queries. The Wireless or Mobile Devices 983 that are the mobile or wireless devices with the processing unit can be used to generate a question. Other modes for generating questions can be Staff 984, Family 985, Individual regarding themselves 986, Other Device 987, Other Individuals 988, and Multiple Individuals 989. Systems with caseloads or wireless or mobile devices could generate questions based on predetermined methods or person-centered approaches. Staff, family members or other individuals might ask questions from their knowledge about the current state of the individual. The system could collect all these information so that it could be used for future analysis. The individual may generate questions by themselves depending on the surroundings or the questions asked to them. When multiple individuals are asked questions at the same time, the individuals might participate in generating questions. These questions generated from individuals directly could be useful while analyzing their preferences and needs. Single or multiple modes of asking questions can be used by the system of Generation of Questions 190.

FIG. 10 shows how the system can determine individual responses using the information obtained from the individuals or the questions asked to them. The system may generate queries in multiple modes or may obtain information directly from the individuals in multiple ways as described in FIG. 9. The individuals may respond to the questions or provide data in various modes 1010, all of which are capable of being recorded by an electronic sensor. These include Voice 1011, Facial Expressions 1012, Hand Movements 1013, Words 1014, Biometrics 1015, Typing/Keystrokes 1016, Individual Tics 1017, Sounds 1018, Touch 1019, Typing Speed 1020, Typing Pattern 1021, Change in Stress Level 1022, Change in Blood Pressure 1023, Smell 1024, Change in Smell 1025, Sweat 1026, Change in Pulse 1027, Pulse 1028, Temperature 1029, Electrochemical Modification 1030, Other Actions from an Individual 1031, Facial Movements 1032, Body Movements 1033, Body Chemistry 1034, Photo 1035, Staff Answers 1036, and Blood Pressure 1037, and any other mode that is utilized.

The system may use one or more format of the response obtained for the same questions for further analysis. For example, the system may use both the words said by the individual and information from the facial expressions on a particular query. The individual may say "I am happy" but the information received from the facial expression might not show the similar result. The facial expressions can be mapped with other data available in the system to determine if this statement is coerced or not.

Figure 11:
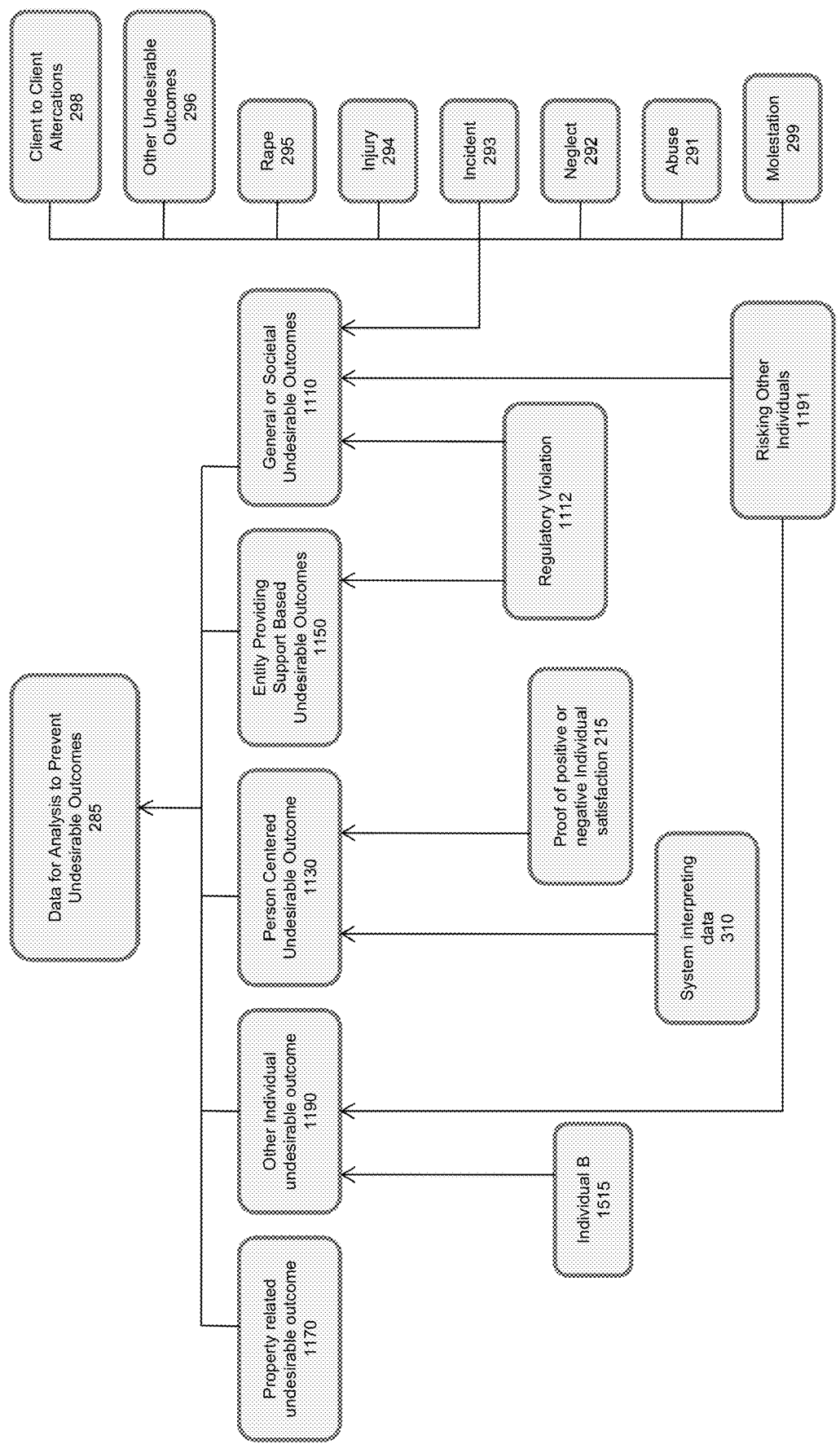
FIG. 11 illustrates an overview on data collection to prevent undesirable outcome.

FIG. 11 illustrates an overview on data collection to prevent undesirable outcome. Data for Analysis to Prevent Undesirable Outcomes 285 indicates that system requires data from individuals directly or from individuals in their vicinity or from staff taking care of individuals or from the surrounding of the individual to detect the possibility of undesirable events. System then analyzes this data to prevent the outcomes of undesirable events. System generates various responses, compares new data with previous data stored in the database and then reinterprets the mapping of information if required.

There may be Entity Providing Support based Undesirable Outcomes 1150 resulting due to staff problems or staff reactions or unpleasant staff behavior and activities or violation of Entity Providing Support policies and regulations 1112.

There may be Person-Centered Undesirable Outcomes 1130 generated on the basis of the proof of negative satisfaction 215 of an individual for services delivered to them or actions taken by the entity providing support or staff or family. The information about the individual's satisfaction can also be determined on the basis of information provided by individuals regarding their goals and analyzing the progress towards achieving the desired goals of the individuals. The system may use the Person-Centered Data Collection Approaches 180 to determine how to collect data that may help create person-centered documentation. The system may compare these records to analyze the progress of the individual towards the desired goals and interpret the information to reflect the individual's level of satisfaction. System 310 interprets individual data by comparing new information with previous information stored in the database and may generate an interpretation which may lead to Person-Centered Undesirable Outcome.

There may be undesirable outcomes regarding Property or costs 1170 which may occur due to damage in property or equipment or any other asset with monetary value.

There may also be other individual undesirable outcomes 1190 resulting due to other individuals attempting to cause harm or put others at risk 1191. For example, there may be a situation where Individual B might attempt to harm Individual A and perform certain actions such as getting hold of a sharp object which may lead to an undesirable outcome for Individual A. The system could be able to capture this information through video or monitoring camera and map this information and automatically take necessary measures to prevent the outcome.

The system could take feasible measures to reduce the possibility of undesired action 770 by notifying appropriate people or staff having caseloads on the particular individual prone to the undesirable incident or through alerting individuals or people surrounding the individual or changing the aspects of the environment. The system might generate smoke or ring alarms or announce the possibility of the occurrence of such incident through speakers or change the lighting of the room where the individual is in or the entire program where there might be other staff and other individuals in order to aware them about the possibility of an undesirable incident.

Figure 12:
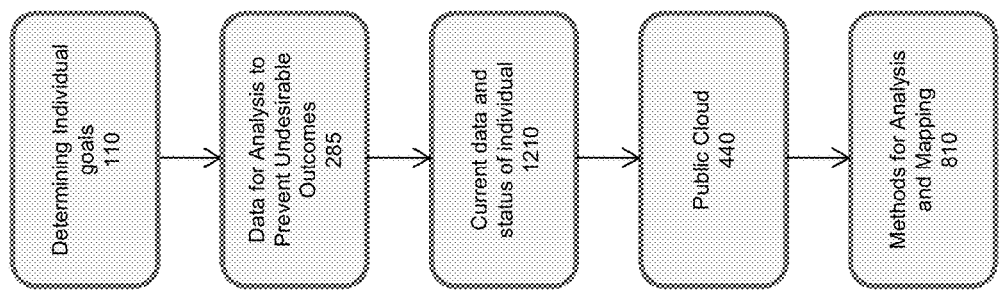
FIG. 12 illustrates the process of making prediction on undesirable outcomes for an individual and determining the information to prevent undesirable outcomes.

FIG. 12 shows how the system could determine the information to prevent undesirable incidents that may cause problems to an individual. As shown by the Determining Individual goals 110, the goals and objectives are determined based on individual's directive and from other entities involved with the individuals. The system gathers a wide range of information about an individual using methods determined by Person-Centered Approaches 180. As the system stores all data including the original backup of each record, it is possible to access an individual's previous history through appropriate caseloads. The Current data and status of individual 1210 represents the individual information obtained for the current state. Analysis or mapping on the current data and status of the individuals with the previous history could be done within the system using Monitoring and Analysis of Information 175 and Reanalyzing old data based on new data 185. Using the new information from the reanalysis of the individual data the system could predict on likelihood of problem for the individuals. For example, if an individual has history of not reacting well to loud noises, the system could be able to predict how the individual may react in the presence of loud noise. The system could then generate data for preventing undesirable outcomes 285 which can be used to do future analysis. The system could look into the Public Cloud 440 to get information from the external sources such as outside sensor devices, radio, internet, video, audio or people and use this public data to recognize that a neighbor or town has construction permit for a specific date. As the system has previous history that noise could annoy the individual that might cause undesirable event, it could notify a staff. The system might send message to the staff with the information to prevent such undesirable event. The system might take measures such as playing music or locking doors or doing something so that the individual could not go near the noise that could be annoying for the individual.

Varying Responses

Figure 13:
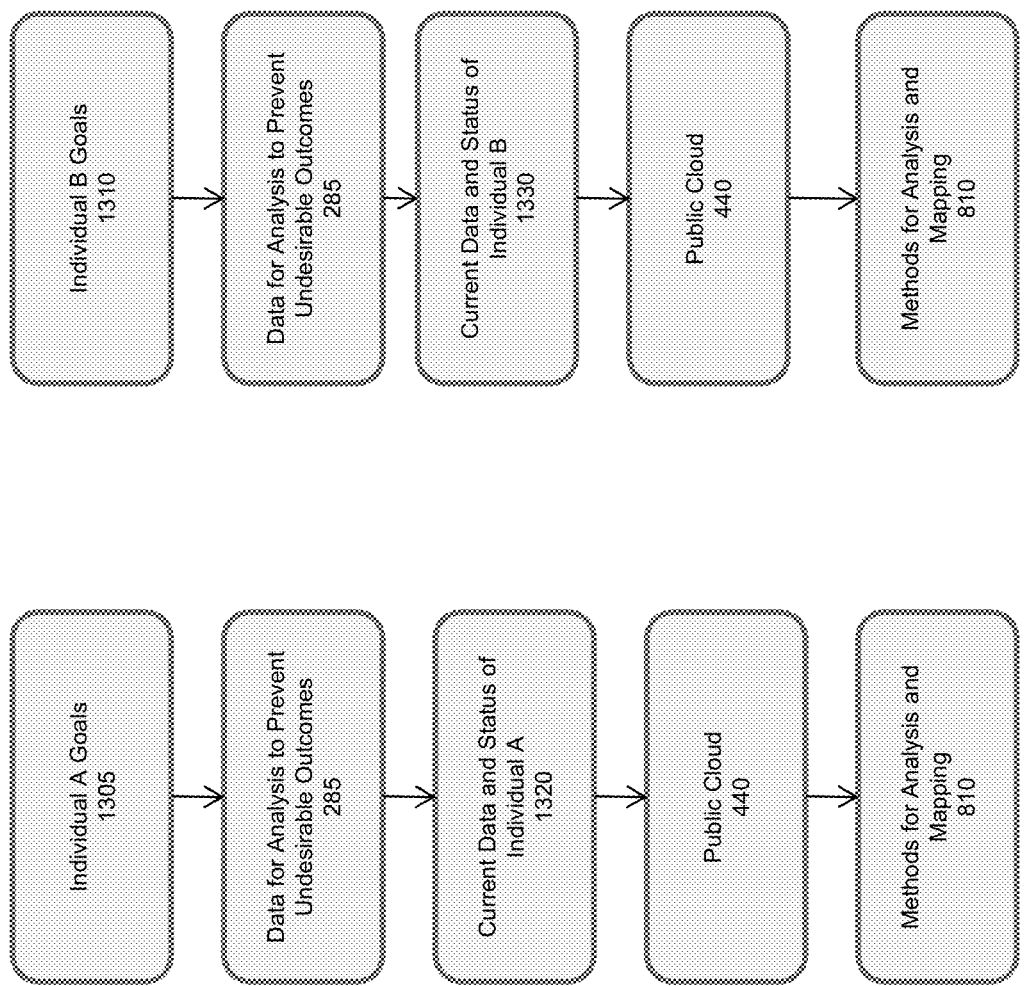
FIG. 13 illustrates how the system with caseloads makes predictions on undesirable outcomes for multiple individuals and determines the information to prevent undesirable outcomes.
Figure 14:
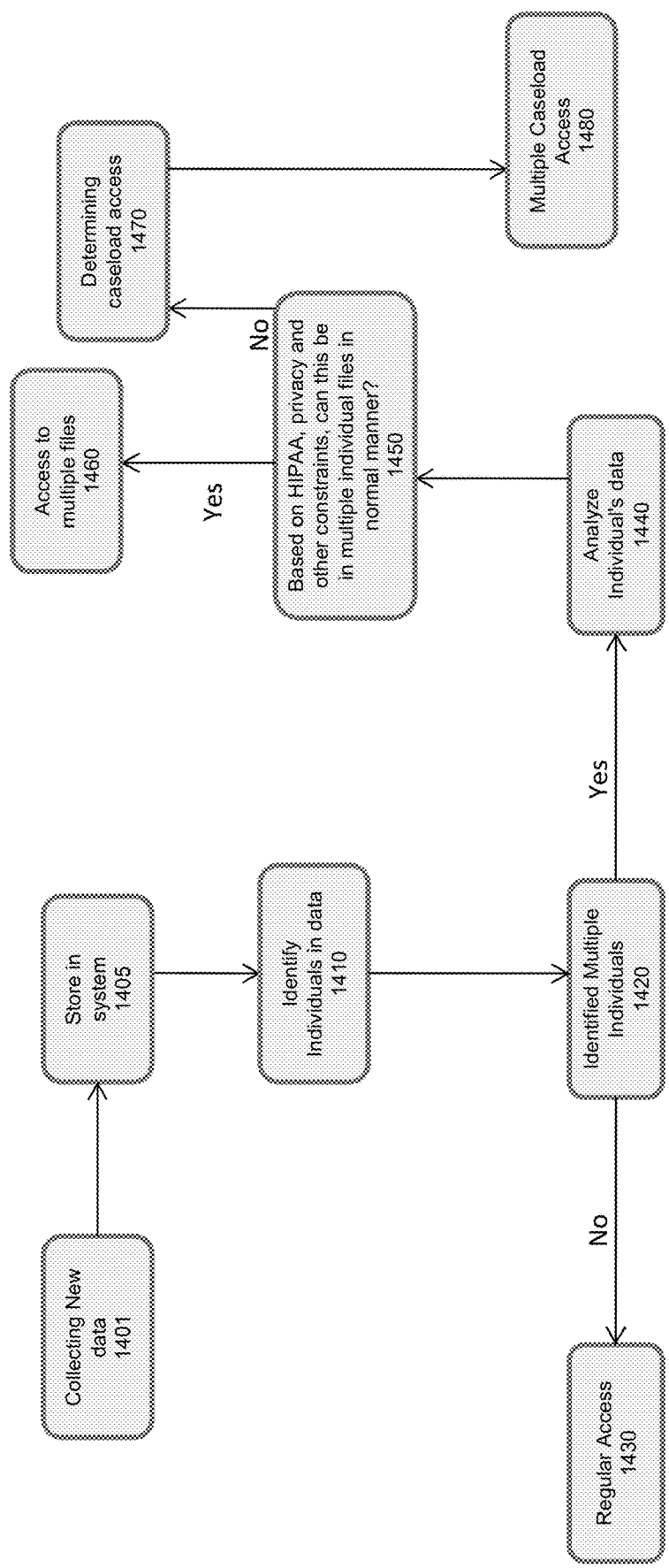
FIG. 14 illustrates an overview on determining caseload access.

FIG. 13 shows how the system could determine the information to prevent undesirable incidents that may cause problems to more than one individual who is present at the current state.

As shown by FIG. 12, the system has detailed history of an individual and is aware of such situations that may cause the individual to react to the particular state. This reaction could have negative or comparatively neutral impact on the individual's health and welfare. In the current environment, there might be two or more individuals who might react to the same incident. However, the reactions from each individual are not necessarily to be same. Individuals' reaction might be different based on the situations where they are, how they are feeling in the current environment or their cognitive state. The system could compare each individual's current data and reanalyze with their previous history to make prediction on likelihood of problems. If the system recognizes that the current situation might cause all individuals to react negatively the system take actions to mitigate the possible annoyance using data to prevent undesirable outcomes 285. If the system predicts that one individual could react negatively but other individual might be neutral, then the system could use its caseload on the individual to determine the actions to be taken to handle possible problems.

If there are two individuals in the current environment with Individual Goal A Goals 1305 and another with Individual Goal B Goals 1310, the system could gather information for each individual for the current state as Current Data and Status of Individual A 1320 and Current Data and Status of Individual B 1330. The system may analyze to determine what situation might cause disturbance to them using the Methods for Analysis and Mapping 810. The system may use the public data for this analysis 440. For example, both individuals might be affected with the presence of loud noise and the system determines that one individual gets annoyed by the loud noise which increases the level of stress. This noise stress might result in migraines or increase risk of depression. The other individual might be disturbed with the noise but it might not cause any harm to health conditions. In such case, the system with caseload on the individual having negative impacts could notify staff to mitigate noise or cause actions which could help the individual.

System can collect data directly from individuals with disabilities or from the responses of staff, family members, friends or other Individuals. System may observe an individual under different circumstances and may capture information as indicated in Collecting New Data 1401 through video 921, audio 922, pictures 923, cell-phones and wireless devices 930. Data generated from individuals under different circumstances are mapped with previous interpretations and are reinterpreted by the system if necessary. These data are stored in the system 1405 and the system analyzes these data for mapping and generating individual responses in pre-defined forms and templates.

A challenge is generating the data in a manner which is private, secure, HIPAA compliant and does not treat individuals as human experiments. Because the system can be designed both to focus on the goals and objectives of individuals with cognitive disabilities as well as having the system process information based on unique caseloads, the goal is to have a reduction in data points needed to create awareness of how to categorize responses.

When requirements or data includes audio 922 or video 921 or monitoring cameras 927 or other modes other than words or numbers, there is a possibility that the audio or video may include information from more than one individual. For example, if a picture is taken then there could be other individuals in the background or other parts of the picture. If a video is taken then there could be other individuals in the background or other parts of all or part of the video. These pictures or video could be of other individuals who could be subject to HIPAA, privacy, or other future regulatory or societal privacy restrictions. Identify Individuals in data 1410 indicates that the system determines which individuals are present in that piece of information based on the information already available in the system such as physical traits, height, complexion, hair color, eye color of the individual that helps to identify the individuals.

If the pictures, audio or the video taken does not include information regarding other individuals then the system can allow regular access to staff members with necessary caseloads on the individuals' data 1430.

If the data collected has information on multiple individuals as indicated in Identified Multiple Individuals 1420, then the system could have the capability to redact, delete, change, morph, or otherwise adjust the information based on analysis 1440 included in individual's file while maintaining the original raw information in the system. As the system could know who has what caseloads as indicated in 780, the system could permit staff and other appropriate people to see information based on their caseloads. The system could be capable of communicating instructions to onsite or remote personnel to act intervene with or monitor an individual. This communication could be determined by data analysis and immediately occur via, wireless systems, fixed mechanical systems or via mobile, robotic, micro robotic and living-micro robotic devices and systems. These devices can monitor, communicate data and be available to receive communications from the system. The information stored in the system could be made accessible to other staffs depending on the HIPAA, privacy and other constraints as indicated in 1450.

The system can also determine that even with attempts at depersonalization, the viewer could figure out who the other individuals in a video or audio were. The system could have the capability to limit access to the video with an appropriate note that information related to a particular individual was being withheld to provide protection to another individual in the video. Appropriate staff or oversight agencies could be made aware of this action.

The system could determine that only staff with caseload access on both individuals could view the information 1480. The system could do this after an analysis of the relative importance of the information on both individuals.

For example, there might be a scenario where individual A is playing in the park with an additional individual B. There is nothing particularly significant about how individual A is playing in the park other than to show they are having a nice day in the park. In the background and foreground, individual C is also initially playing in the park with additional individual D. After a short period individual D is seen throwing a ball at individual C in an abusive manner. The video device is capturing the entire scene, and it could not be possible to separate the video of individual A without including the potential abuse of individual C by individual D. The system can detect individuals from the video clip based on the information stored in the system, analyze the information received from the clip and decide on allowing/restricting access to particular staff. The system could have the capability to restrict access to the video in the file for staff having caseload access only on individual A or individual B. Since the individual C was being hit by individual D, staff having access on individual C can access the file and the video clip will be added to individual C's file. The system keeps track of all the incidents happening with and around the individual in each individual's file. In this manner the system can store necessary information regarding an individual which the individual might be unable to communicate with others.

The information can be used to analyze the behavior of an individual or his/her reaction to a particular incident. There might be an incident that has occurred to an individual while he/she was playing in a park which can make the individual upset. The reason for being upset may not be communicated by the individual with other people but since the individual was continuously monitored by external or internal devices and the system was tracking all the information, the reason can be traced by the people monitoring the individual.

There might be an incident that occurred with an individual when the individual was young which has resulted in his/her behavioral changes. There might not be staff present in the agency who witnessed such an incident occurring to an individual to communicate it with other staff. However, since the system can capture and store the information, it can always be available for future reference. If there is a re-occurrence of the same event that once occurred to the individual with some other individual or to himself/herself, the reason behind the behavioral changes of the individual might be traced even by newly recruited staff, as the information about the initial occurrence of the incident was already stored in the system. For example, Individual A might have had some incident of abuse or violence or any other terrible incident occurring to him in the past. One day while individual A is playing with individual C and individual D, individual D might hit or abuse individual C which can cause individual A to recollect a past incident. This data can go into the files of both individual A and individual C. System can redact the information on individual C and provide access to staff having caseload on individual A to investigate the behavioral changes of individual A by giving access to his/her file. Besides, the system stores raw data files, which can be accessed by staff with appropriate privileges if deemed necessary. Similarly, individual C's file can have redacted information on individual A so that staff can access data on individual C only. The system not only stores data on individuals for further analysis but also determines the accessibility to that information.

For example there might be another scenario where video captured on the Individual A has in the background Individual B playing in the park or walking. Since the captured information for Individual A cannot be possibly separated from that of Individual B, so the system could analyze this scenario and determine whether to restrict or allow staff having caseload on Individual A only to access this information. The system could analyze depending on HIPAA and other privacy constraints as indicated in 1450 and if there is no privacy violation in allowing access to the data on Individual B to the staff with caseload on Individual A, then the information can go into the file of Individual A. Again, if the system analyzes that there is no privacy violation in reflecting the information on Individual A to staff having caseload access on Individual B only, then the information can go into the files of each of these Individuals and staff with caseload access on either Individual A or Individual B can access this information. Staff having caseloads on both the individuals can also have access to this information 1460. As the system is caseload based, it can be possible to find someone with access to both Individuals' data which means it could be possible to ensure that someone with appropriate access can see the actual event without compromising security or privacy.

There could also be a scenario where Individual A is subjected to abuse whereas Individual B and Individual C are also in the video doing something of significantly less importance. The system could analyze this data from the perspective of each Individual and if revealing the data on Individual A to staff not having caseload access on that Individual subjects to privacy violation then the information can be restricted from being accessible to those staff. This information will not go to the files of each of these Individuals who are part of the information captured in the video but can go only to the file of Individual A and accessible to those with caseload on Individual A. System could provide a note for informing staff having caseload on Individual B and C that the information has been restricted from viewing in order to protect privacy policies 1470.

There may also be a case where data collected using video or audio has information on Individual A, B and C. In this video or audio information, Individual A and B might be subjected to general abuse whereas Individual C has no significantly important data recorded in that video or audio. In this case the system may analyze the information and on the basis of importance could include this data to the files of Individual A and B and may restrict staff with access only on Individual C to view this information. The audio or video footage can be redacted in order to abide by HIPAA and privacy policies and access can be given to staff on the video or audio clippings with redacted information on individuals on whom they do not have necessary access privileges.

In case where both Individual A and Individual B are subjected to possible abuse, data captured by video can be processed by the system and information can be added to the files of both these Individuals. The system can provide access to these files to those having caseloads on both Individual A and Individual B 1470 or by redacting information on Individual A for staff with access on Individual B and vice versa.

The system could take this action if it was determined that there is sufficient information to identify an additional person based on the information available in the system. For example, if parents or guardians of individual A saw a situation occurring in a video with a different individual who moved and/or acted and/or looked like a housemate in a situation where only two individuals lived in a house, depending on the relatively sensitivity and importance to individual A and individual B 1440 the system could disallow access to video or other information on individual A if it provided certain information on individual B 1470 which is subjected to privacy constraints. The data could remain in the system if there was an audit or investigation or any such purposes.

System may provide data access to auditors or surveyors as the original data is available in the system. An example could be that a video or audio is used for proof of service delivery or needed to show that reimbursement should be made or a service was delivered for individual A. If that video had information regarding an individual or individual other than A, then the system could note that additional information is available to an auditor or surveyor.

Figure 15:
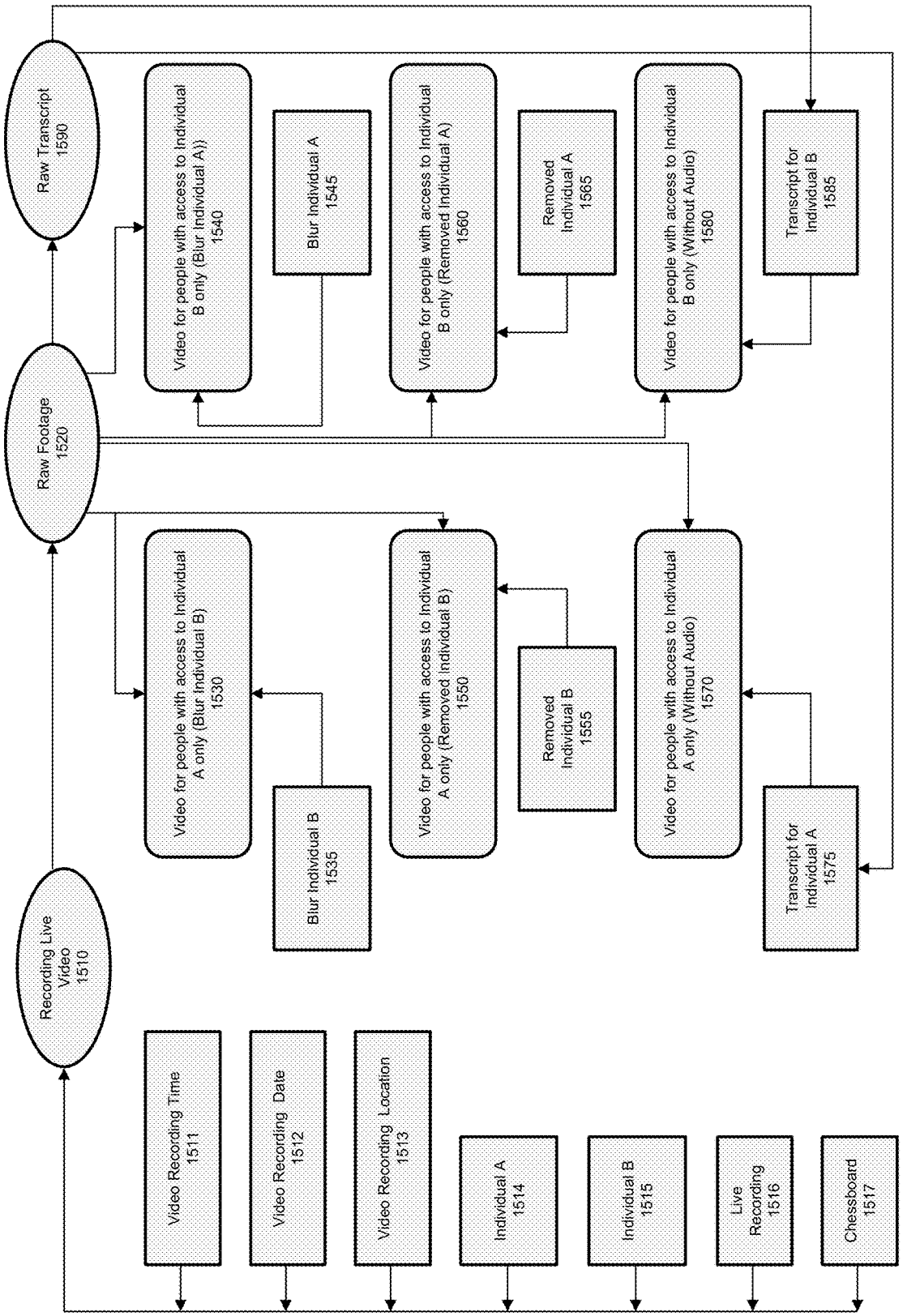
FIG. 15 illustrates how the system could capture and store the video footage for the individuals who are present in the current situation.
Figure 15A:
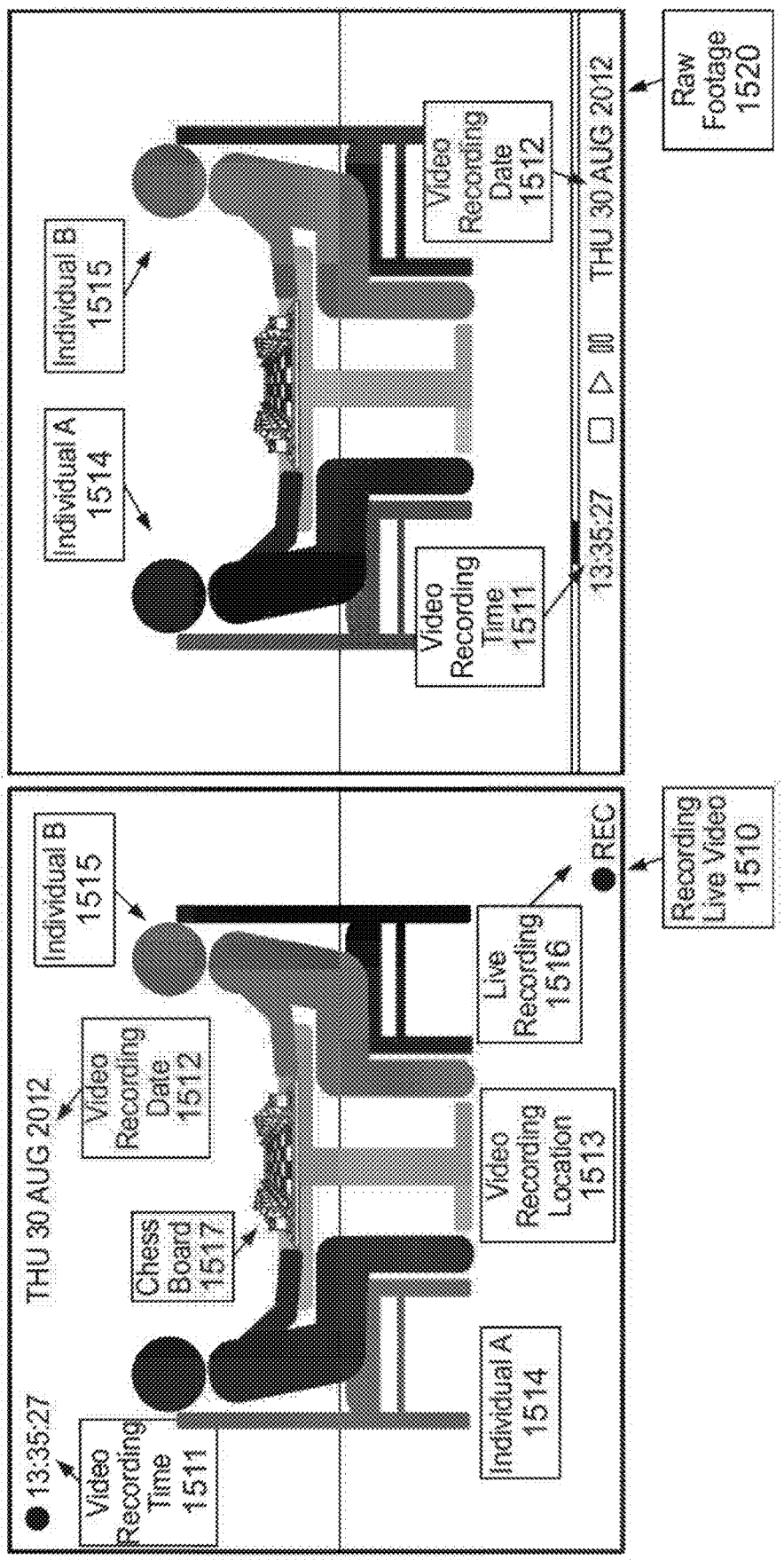
FIG. 15a represents the video recording of individuals' activities in real time and the raw footage available in the system.
Figure 15B:
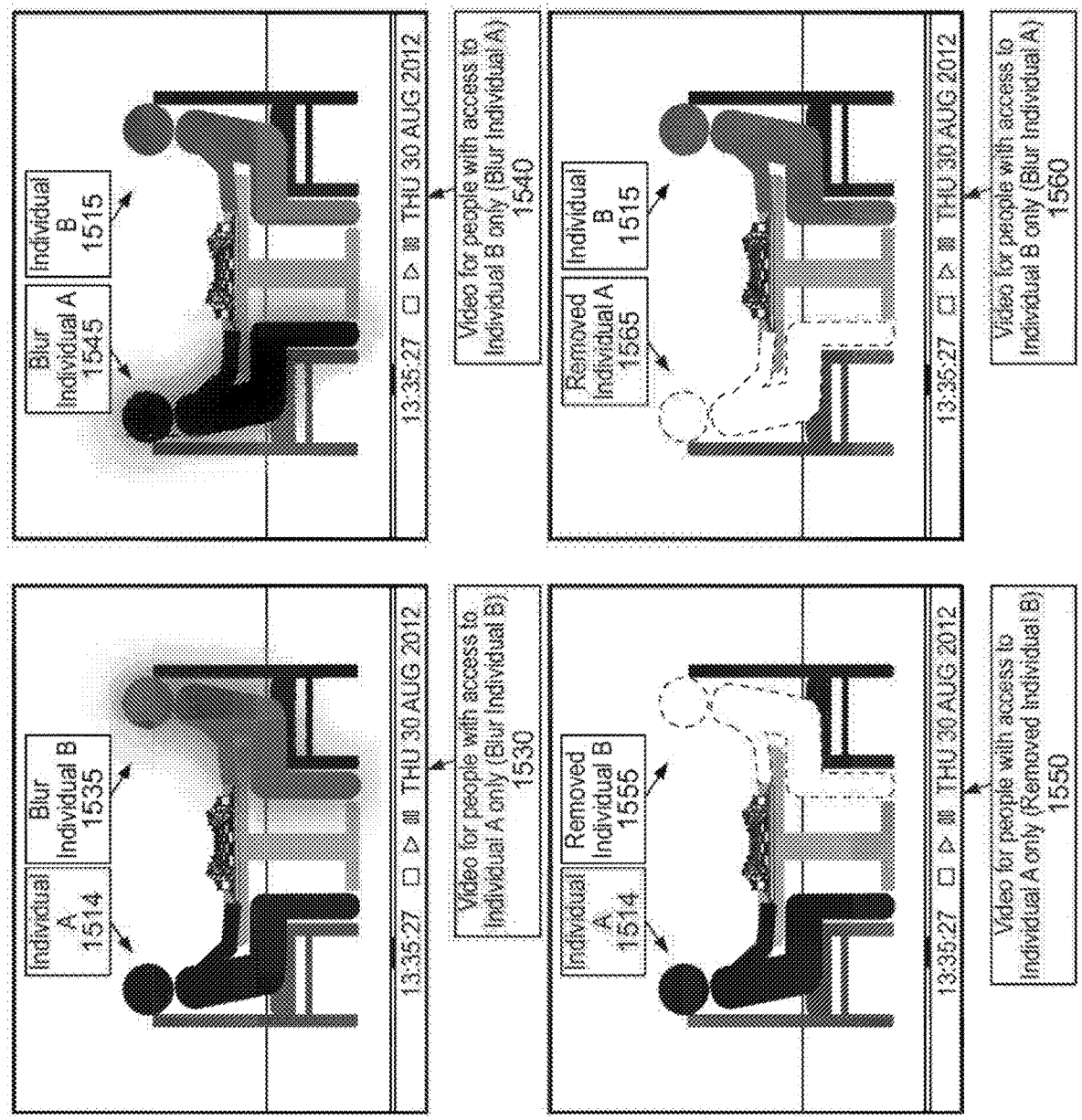
FIG. 15b represents the video footages of individuals' activities modified depending on the caseloads privileges of users.
Figure 15C:
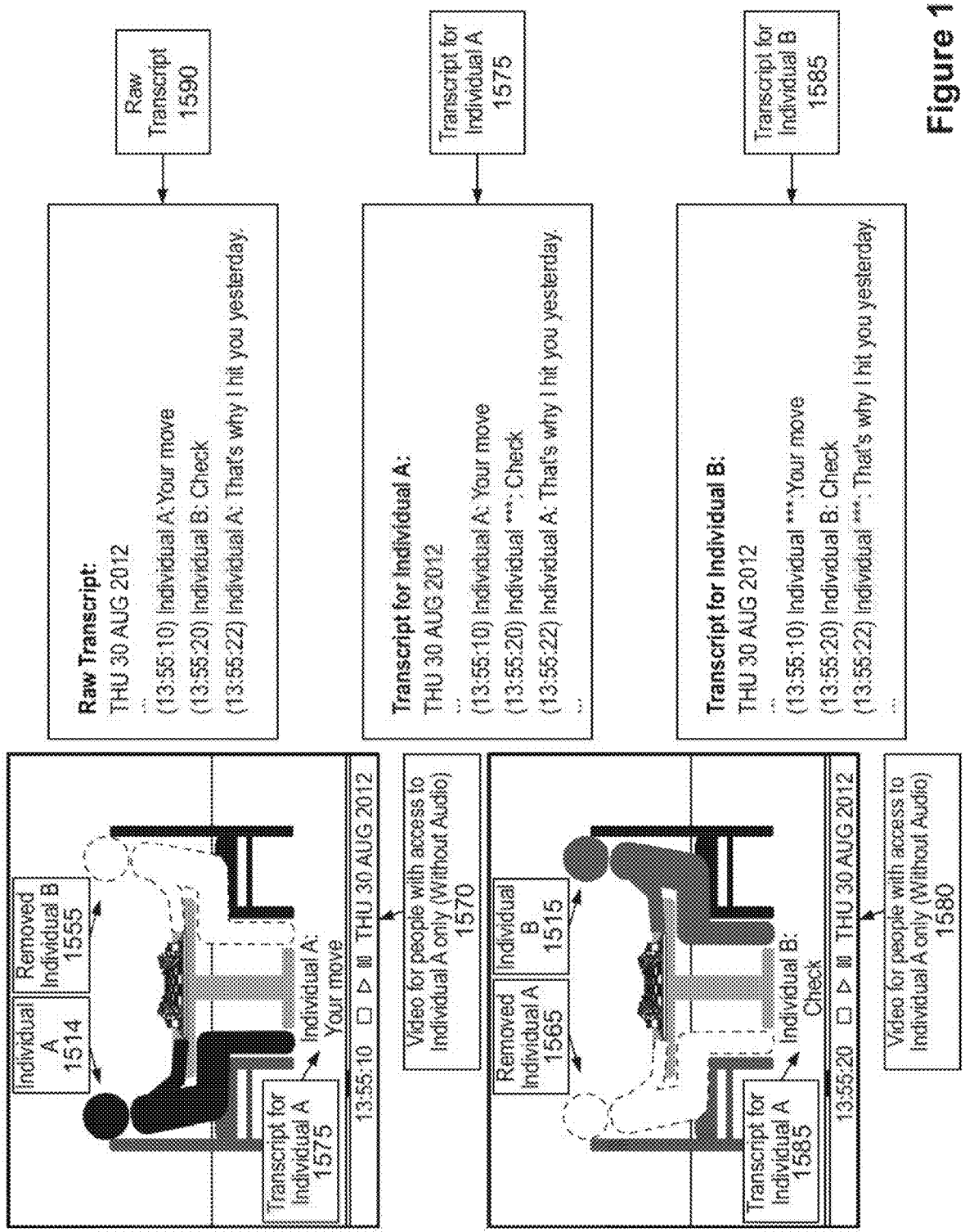
FIG. 15c represents the raw transcript obtained from the video recording of the individuals' activities as well as modified transcripts for users with limited caseload privileges.

FIG. 15 illustrates how the system could capture and store the video footage for the individuals who are present in the current situation. In FIG. 15, the Recording Live Video 1510 shows that the system may get information from video records on individuals' activities by the data fed into the system by video devices located at different places in an area. This video recording can be used to record individuals' daily logs or shift notes. The Raw Footage 1520 may be available in the database. People with appropriate access privileges on the individual, whose information has been captured by video recording, may access the video from the database. If no one has access privileges on those individuals, the raw footage may still be available in the database. The Video Recording Time 1511 and Video Recording Date 1512 represent the time and date of when the video has been captured. This information is fed into the system which keeps a record of the individual activities. The system also has Video Recording Location 1513 that provides information about the location where the individuals were present such as playing room, kitchen or activity room. The information about the date, time and location is available in both raw video or the video adjusted based on staff members' access privileges.

The system can have processes and rules to protect Constitutional Rights. There are issues both in terms of the right to video as well as access to the video. In fact, there may be situations where having this system will allow additional minimally invasive monitoring because individuals or others can set outcomes based rules for what someone should look at a video (or other data). For example, a video can be set only to be viewed when someone falls or is hit or certain events occur. An individual or society may then feel more comfortable knowing that only in the event of a predefined event can a person see a video. There could be an interpretation that having a machine viewing a video and only reporting in certain events (someone was hit, fell, sound above a certain decibel, or other preset conditions) could mean that the absence of an alert or absence of notification that something occurred could still provide information. Combinations of caseloads and super roles can allow the system to be configured to meet various legal, judicial and constitutional interpretations. There are various locations where data can be collected including both public and private locations. For example there are features in the system for blurring, redacting and removing information to help comply with some of these potential issues.

At the time of video recording the system recognizes the identity of the individual based on the previous information of the Individual in the system. As shown in FIG. 15, the system might capture the video recording of when the Individual A 1514 and Individual B 1515 are in the activity room or some other location and playing chess or involved in any other activity. The system could identify the individuals by matching their face and other physical traits with the previous records available in the system. Individuals' detailed activities while playing chess or any other game can be recorded live 1516. An individual might be present during the activity hour but might not participate in any activities. It might also be the case where the individual is participating in playing chess (1517) but the level of participation is not satisfactory. Due to some emotional stress the individual was unable to concentrate in the activity. The live recording can then help determine the individual's level of participation or reason that might be affecting the individual's performance. The system could also recognize the place where the video camera is located and this information can be used to locate an individual's presence during the activity hour which could be useful for daily logs or shift notes.

The raw footage of the video recording could be stored under each individual's files in the database. Access to the video footage depends on people's caseload privileges on the individual. If no one has caseloads on the individuals, the system could still store this in the database for the needs that may arise in the future and for people who might have access to them in the future and need to analyze previous history. The video format might be displayed differently for people who do not have access privileges on both Individual A 1514 and Individual B 1515. People with caseload access to only Individual A 1514 and not to Individual B 1515, might be given access to the video where there is information on Individual A only 1530 with Blur Individual B 1535. In the video footage the image of the Individual B may be blurred beyond recognition so that the person who is viewing the footage cannot identify who the individual is. This is to ensure that HIPAA is not violated. Similarly, for the people who do not have access to Individual A 1514 but need to access video footage for the Individual B 1515 they have access privileges on, the system could display the footage where there is information on Individual B 1540 with the Blur Individual A 1545. In the video footage the image of the Individual A may be blurred beyond recognition so that the person who is viewing the footage cannot identify who the individual is. The system can edit any recorded information. This editing can include blurring (1530), redacting (1560), animating or adjusting access to the information of individuals. This can be done prior to any human seeing the video. All data can still be saved in the raw form if further investigation or audit needs it to be required. The system can detect the individual to be blurred depending on the information about the Individual stored in the database. The information may contain the physical traits of an Individual as well as biometrics, retina recognition, voice recognition.

The system might also remove Individual B rather than just blurring from the video footage that needs to be viewed by people with access to Individual A and not to Individual B. Individual B can be removed from the video footage 1555 and there can be data on Individual A only as shown in Video for people with access to Individual A only (Removed Individual B) 1550 and people may therefore be unable to locate the presence of the Individual B. Similar, people with access to Individual B but not to Individual A cannot see Individual A as Individual A can be removed from the footage 1565 and could see the footage with information on Individual B only as shown in Video for people with access to Individual B only (Removed Individual A) 1560.

In the recorded videos, the system has different combinations of video and audio depending on what an individual says during the recording time. The system has the capability to know the entire transcript (Raw Transcript 1590) and to determine who should get access on which combination of the video and audio based on caseloads. The system might have the option of Video Only where information on either Individual A or Individual B is redacted 1570, 1580 with written transcript because something is said which might be a problem. These video only modes can have redacted information on Individual A 1570 or Individual B 1580 to provide access to people with appropriate caseloads. For example, the video record with Blur Individual A 1540 that needs to be viewed by staff with access to Individual B 1515 and not to Individual A 1514, might not have the audio for the Individual A so that people could not identify the individual with audio voice. The system has the entire transcript and if it identifies any statement that the staff needs to know about Individual B then the system might include the transcript for Individual B 1585 redacted from the Raw Transcript 1590. Similarly for staff having access on Individual A can have the video only option with the transcript for Individual A 1575 only and a redacted transcript for Individual B from the raw transcript. As shown in FIG. 15, there might have been conversation between Individual A and Individual B while playing chess or some other activity having the statement that Individual A had hit Individual B. Based on this statement the system could determine that there might have an injury incident which the staff should know about. The system can therefore decide to include the transcript to the video recording in the file of the particular Individual so that the staff could investigate this incident further and report to supervisors or others with necessary privileges.

Incident Reporting

Figure 16:
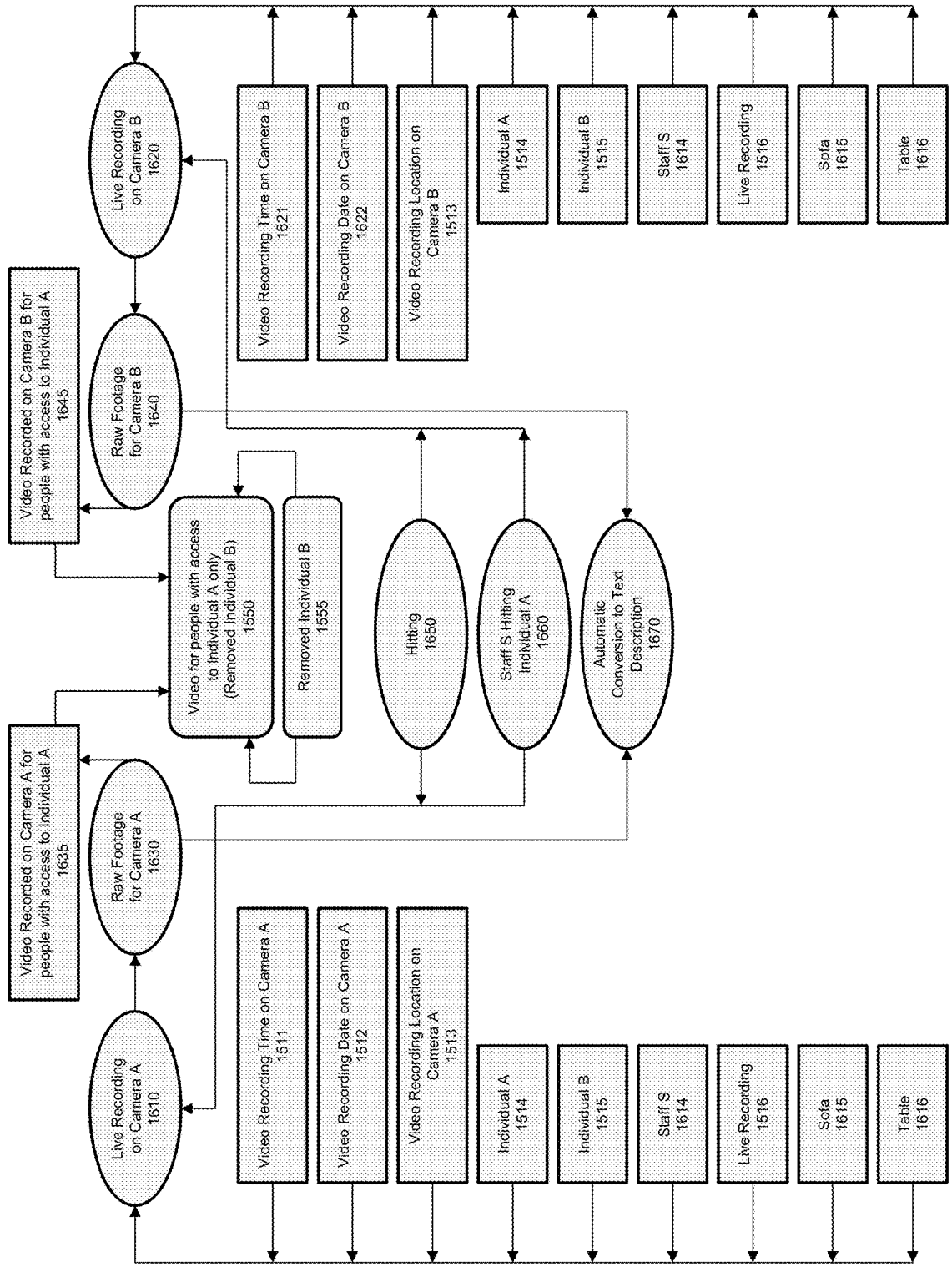
FIG. 16 illustrates the example of how the video recording of an incident can be analyzed for incident reporting.

FIG. 16 illustrates the example of how the video recording of an incident can be analyzed for incident reporting. As shown in 16a, the system gets information from the video footage of camera A 1610 and camera B 1620 which are located at different positions in a room and captures information regarding all the details 1516 of that location including furniture in the room such as sofa 1615 and table 1616. It captures data when the Staff S 1614 hits the Individual A 1514 in front of the Individual B 1515. Since cameras are located at different locations to monitor the Individuals, the system may analyze the data captured by different cameras and consider data from the camera which provides precise information. Using the video recording, the system can submit an incident report with the details of the time of when the incident occurred 1621, the person who hit the individual 1660, the type of abuse 1650, where the individual was abused 1513 and date 1622 of the incident which is required for submitting an incident report. The system can determine the notification level based on the type of incident that has occurred. Staff could also notify the persons who should be aware of this incident. The staff might have access to Individual A but not to Individual B. In this case, the staff may be able to view the video where there is information on Individual A only 1550 and the information on Individual B redacted or removed 1555. The system can take the information captured by the video for the Individual A from camera A and camera B 1635, 1645, analyze the information, submit an incident report and notify appropriate people with necessary caseloads. The staff could inform this to the Supervisor who has caseload privileges to access the raw video footage and ask the Supervisor to investigate this incident thoroughly. The Supervisor might then use the raw video footage 1630, 1640 obtained for both the cameras to identify the details of the incident, investigate further and review the incident report filled in by the system.

The system might be able to convert the incident captured in the video to text description 1670. For this incident, the system might convert this incident into text stating "Individual A, Individual *, Staff Member S are present in the video. Individual * is standing in front of the Individual A. Staff member S is hitting Individual A. The name of the other Individual has been withheld for privacy reasons." This text can be used to notify the staff about the incident briefly that has caseload access on Individual A.

Figure 16A:
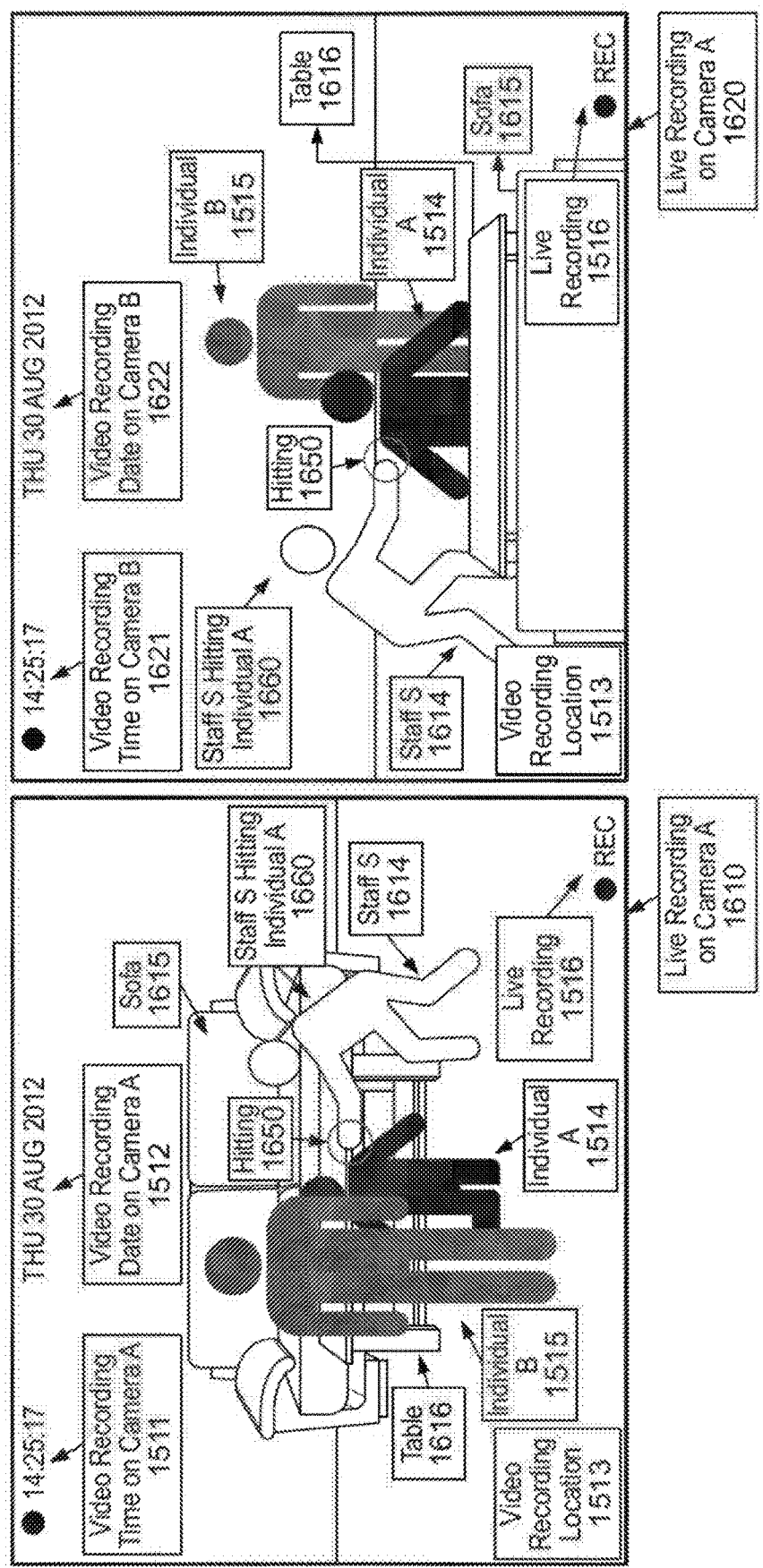
FIG. 16a represents the real time video recording of an incident where an individual is hit by a staff member, recorded by two different cameras located in different angles.
Figure 16B:
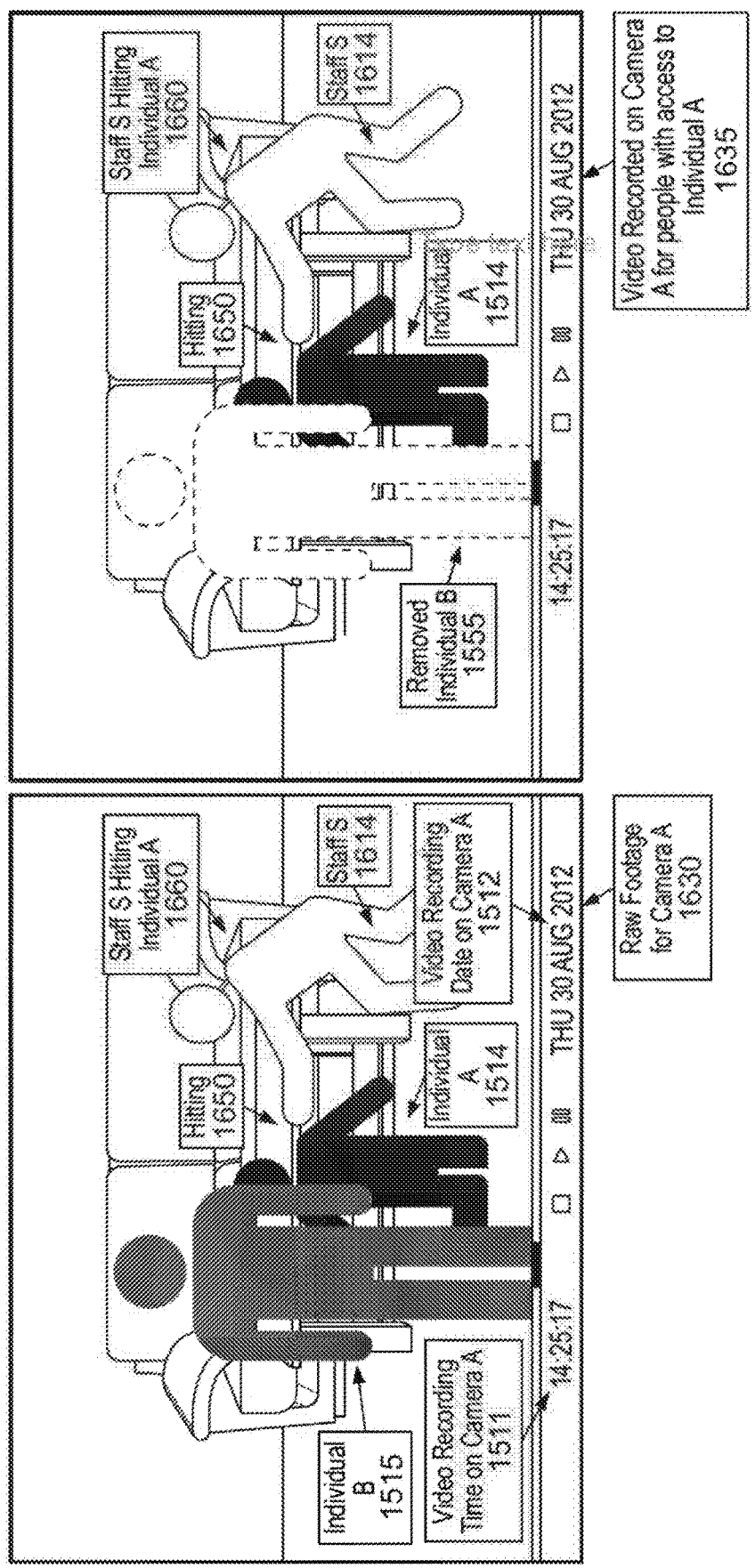
FIG. 16b represents the raw footage stored by the system for the first camera and the corresponding modified footage for users with limited caseload privileges.
Figure 16C:
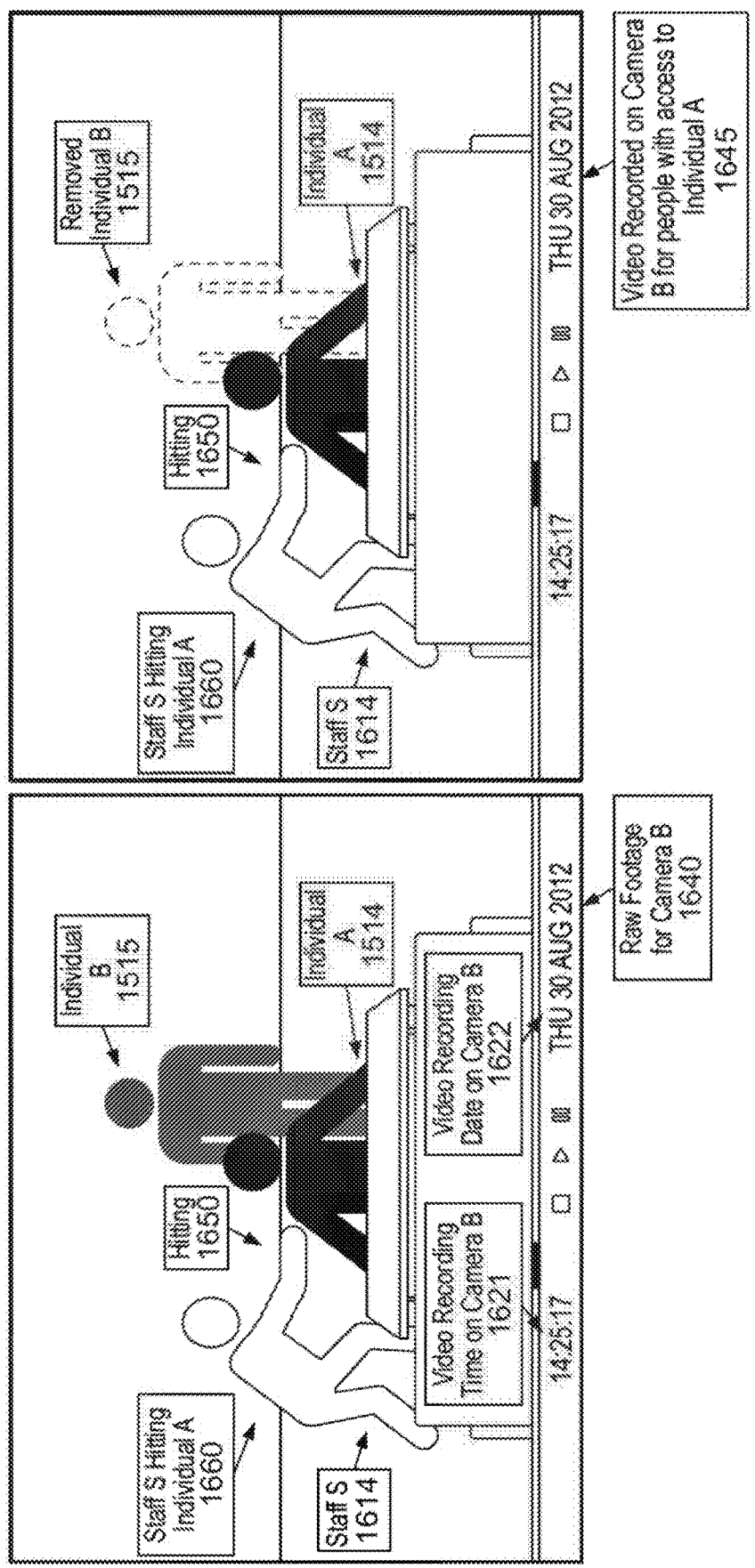
FIG. 16c represents the raw footage available for the second camera and the corresponding modified footage for users with limited caseload privileges.
Figure 17:
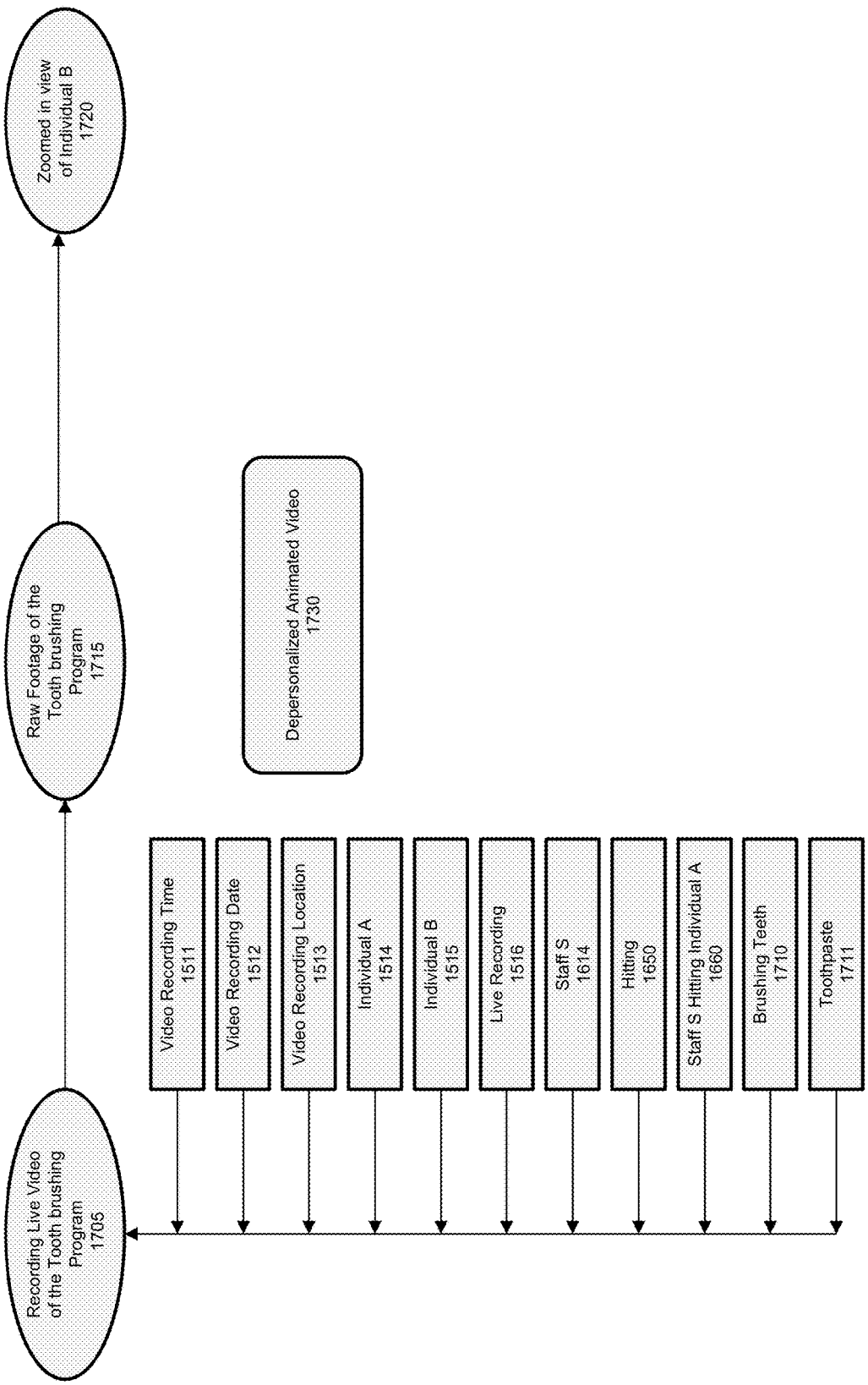
FIG. 17 illustrates the example of how the video recording of an activity program can be analyzed for ISP Data collection and incident reporting.

FIG. 17 illustrates an example of how the video recording of an activity program can be used for collecting data on Individual Service Planning (ISP) and incident reporting. The Recording Live Video of the Toothbrushing Program 1705 represents that the system is recording the live video of the Toothbrushing program. This recording of activity program is not limited to the Toothbrushing Program only. It could be other activity programs such as cooking program, bed making program, hygienic program, laundry program, grocery program etc. Agencies have these programs to document on and collect data to track the progress of the Individuals in achieving their goals. The Live Recording 1516 in FIG. 16a shows that the system is in the recording mode and capturing information from the surroundings. While recording the live video the system captures the Video Recording Time 1511, Video Recording Date 1512, and also the location where the camera is located as the Video Recording Location 1513, the system captures the presence of a person in the location by matching their biometrics and other physical traits. In FIG. 17, while recording the live video the system captures the raw view of Individual A 1514, Individual B 1514 and Staff S 1614. The system can analyze the raw view of the persons and map with the previous identification records such as biometrics, retina recognition, and voice recognition available within the system to identify who the person is.

At the time of Toothbrushing Program the system recognizes all the activities done by the individuals. In the Toothbrushing Program the individual may do different tasks as required by the programs. Other type of activity program may include different set of task and respective actions. In the Toothbrushing program the actions may include picking up toothpaste, unscrewing the cap, putting the cap down, picking up the toothbrush, squeezing toothpaste onto toothbrush, putting toothbrush into mouth, brushing teeth, rinsing mouth, putting the toothbrush down and so on. In FIG. 17 the system captures the action of Brushing Teeth 1710 while the Individual B was brushing. The system can collect data for filling in the ISP Data form from the actions captured in the live recording. For example, if the Individual was able to brush teeth independently then the system could put this information in the ISP Data form and score this task according to the scoring method defined in the ISP Program form. The system can store the Raw Footage of the Toothbrushing Program 1715 which can be accessed by people with appropriate access privileges on the individuals who were present at the Toothbrushing program.

During the program, the Staff S may hit Individual A due to misbehaving or expressing unwillingness to do a particular task. Since the system captures the live video of the event, it can recognize this staff action as Hitting 1650 and record the incident as the Staff S Hitting Individual A 1660. The system can also submit an incident report using the information about the incident captured in the video recording. In this example, in addition to documenting the incident report regarding individual A, documentation may be required regarding Individual B and the tooth brushing program. It may be possible to zoom in on Individual B (1720) to show them brushing teeth and their face without showing Staff S hitting Individual A. That could help achieve the goal of minimizing access to the knowledge and video of Staff S hitting individual A to only those people who have the roles and caseloads to see that. However, the fact that Individual B may associate actions and feelings from the incident of Staff S hitting Individual A with the toothbrushing program might or might not affect how they act in the future regarding their toothbrushing program.

The system can deal with the incident of staff S hitting individual A from a few perspectives. The system could determine which combinations seem most appropriate based on the analysis performed by the system which may include point scoring method (820), regression analysis (830), method for Individuals in Declarative position (840), Outcome based triggers (850), Iput based triggers (860) or other forms of analysis (870). The system can document in Individual B's program a Zoomed in View of the Individual B (1720) which shows Individuals B's reaction and face. The system can also include in the documentation either an animated, redacted (1560) or blurred piece of video (1540). The system has information on multiple individuals and based on caseloads and roles the system can determine what future actions may occur.

The system may be aware of which staff have access to both individual A and individual B and could be in a position to see the full clip from the perspective of either individual A or individual B. The system may continue to monitor in the future the impact on Individual B. For example if the system notices certain behavioral changes in Individual B regarding their ISP program or other programs or in acting around Staff S, the system can initiate a reinterpretation. The system might look at additional information to determine a possible cause or explanation for individual B's future actions.

The results of this could include training for Staff S, criminal action against Staff S, removal of Staff S from Individual B's home while determining that nothing wrong was done, additional therapy or work with Individual B on specific issues raised by the situation, changes in recommendations of how to permit Individual B to do their tooth brushing program, recommendations that no changes are needed or other possible recommendations.

If there is a certain behavioral change in Individual B after Staff S hit Individual A, the reason for that may be detected from the video clip by itself or in combination with other data and information. The system may allow staff having access to Individual B to view this clip and may provide them with some guidelines on what measures to take. The activity of staff C hitting individual A while Individual B was doing its Toothbrushing ISP program may cause changes in outcomes and actions of Individual B and the system can use this data to analyze and understand what happened and then make recommendations on future action.

To understand the individual's' reaction in such cases the system may use the Depersonalized Animated Video 1730. The system may create a depersonalized animated version of the incident reflecting that a staff is hitting an individual during Tooth brushing program. This animated video can be used to analyze the changes in facial expressions and determine the individual's reactions in such cases.

Figure 17A:
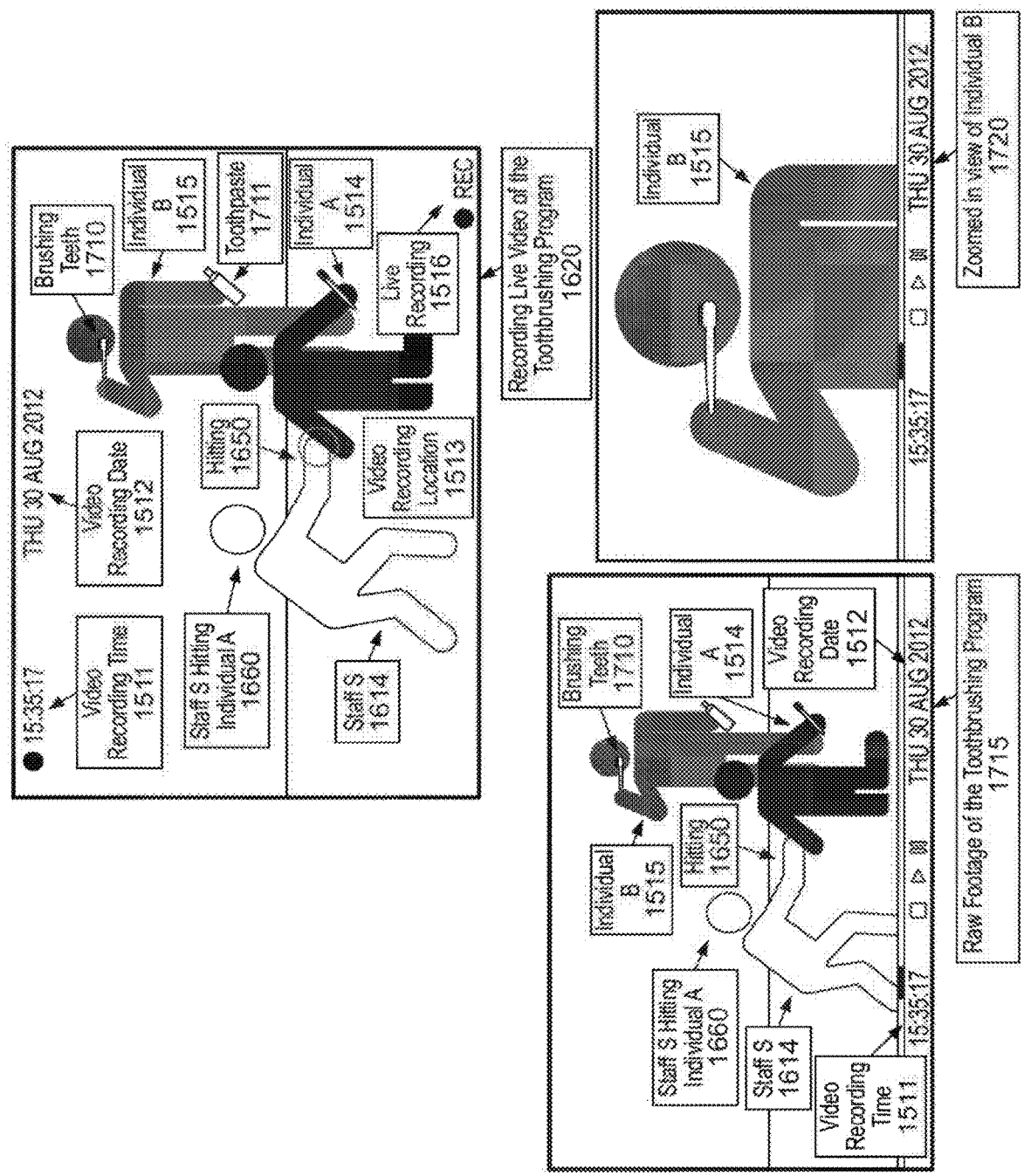
FIG. 17a represents the sample video recording of an activity program where one of the individuals is hit by a staff member.

FIG. 17a is the sample of the video footages of the Tooth brushing Program. The sample footage of the Zoomed in View of the Individual B 1720 represents that facial expressions in such zoomed in view can be used to understand the individual's reactions.

Figure 18:
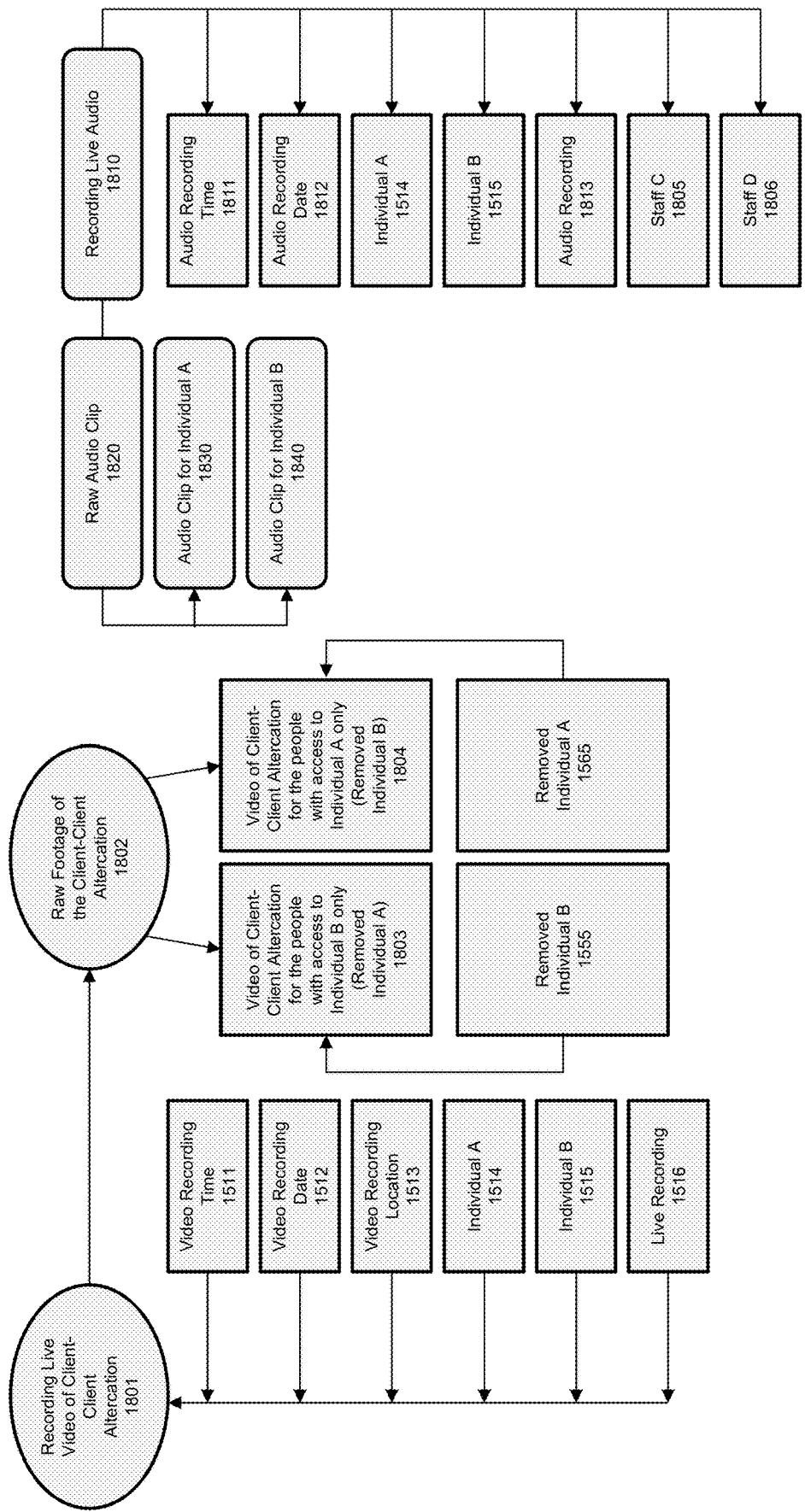
FIG. 18 illustrates an example of how the system can analyze client to client altercations by means of a video record.

FIG. 22 illustrates the process of an automated ISP Data Collection form using the live video recording of an activity program. In FIG. 22, different fields on the ISP Data Collection form has been filled in by the system using information captured in the video recording. As shown by FIG. 17, the system can capture the raw view of the persons who were present at the Toothbrushing Program as Individual B 1515, Staff S 1614 and also the location where the camera is located as the Video Recording Location 1513. For the Toothbrushing Program this location is the activity room. This information can be mapped with previous records to identify the individual within the system and to locate the Provider Program under which Individual B is attending the Toothbrushing Program. Using this information the system can open a new ISP Data form with the System Generated Time Data Entered on 2205, System Generated Date Data Entered on 2210, Program Name Determined By System 2215, Time Zone Determined By System 2220, ISP Program Name Determined By System 2225. The information about the Data Collection Date, Begin Time and End Time can be found from the Video Recording Date 1512, Video Recording Time 1511. The information about the location can be found from the Video Recording Location 1513. The system can put the score for each task defined in the ISP Program by analyzing the actions in the video recording. As shown in FIG. 17, the Brushing Teeth 1710 action can be mapped to the 'Brushing Teeth' task of the ISP Program. The system may analyze the video to determine the level of the individual's independence while brushing teeth and put score accordingly. For example, the system has put Full Partial Prompt for the 'Brushing Teeth' task using the information from the Raw Footage of the Toothbrushing Program 1715. FIG. 18 illustrates an example of client to client altercations by means of a video and audio recording.

As shown in FIG. 18, the system can record the live video of the client-client altercation 1801. The Live Recording 1516 represents that the system is capturing the information from the surroundings that include the raw view of the Individual A 1514 and Individual B 1515, the Video Recording Time 1511 and Video Recording Date 1512. The system can store the Raw Footage of the Client-Client Altercation 1802 in the database which can be accessed by the people with appropriate access privileges on the individuals. The system may redact the raw footage 1803 depending on people's caseload and access privileges on individuals. For example, if a staff who has access to the Individual B, not to Individual A may view the Video of Client-Client Altercation for the people with access to Individual B only (Removed Individual A) 1803 where the raw view of the Individual A could be removed or redacted 1565. Similarly, the system can adjust the raw footage for the staff member who has access to Individual A, not to Individual B. In the Video of Client-Client Altercation for the people with access to Individual A only (Removed Individual B) 1804 the system may remove or redact the information on Individual B 1555. However, staff having access on both Individual A and Individual B can access the raw video footage where there is no redacted information. The system can also determine who has viewed Individual files and the caseloads of those people. The system can provide an animated video to hide the real identity of the Individual but to convey the information at the same time.

Access to the video is determined by caseload and roles. The system can track who has seen the data and information. The system may determine that someone should look at the data and suggest that someone with an appropriate caseload look at the information. The system can look at the information and make recommendations and take action. The system may also suggest a change in caseload based on its information of people's roles.

The system may report this incident using the video recording and may also use the audio recording to collect more details from the surrounding which might be needed to report this incident. As shown in FIG. 18, the Recording Live Audio 1810 represents that the system can record the conversation between individuals. The Audio Recording 1813 shows that the system is recording the sounds present in the surroundings. The system can store the recorded audio in the database as the Raw Audio Clip 1820 which can be accessed by the people with appropriate access privileges on the individuals. While recording the audio, the system can capture the Audio Recording Time 1811, Audio Recording Date 1812 and store this information along with the raw audio clip. If a staff member with access to Individual A, but not to Individual B, wants to access the audio clip for Individual A, then the system can remove or redact the audio for Individual B.

Therefore, the Audio Clip for Individual A 1830 can be adjusted so that the staff could not identify who the Individual B is from audio clip. Similarly, the system can adjust the Audio Clip for Individual B 1840 for the people who have access to Individual B but not to Individual A. Depending on the goals and objectives of the analysis the system can use different tools to determine relevant information. In Audio Clip for Individual A 1830 even with only a portion of the dialog, for example the listener can determine that Individual A stated "Don't hit me" and "That hurts." The system could compare that to previous instances where Individual A made similar comments. Perhaps the individual was having previous issues with working on speaking up for themselves, and even though they were hit it might be significant they spoke up and said "Don't hit me." It also could be that the staff was trained to step in the middle after hearing that Individual A said "Don't hit me." In that case there could be issues with staff training. The system can have multiple methods of analyzing, collecting and reviewing data and it is not expected that every method will work in every situation.

Figure 18A:
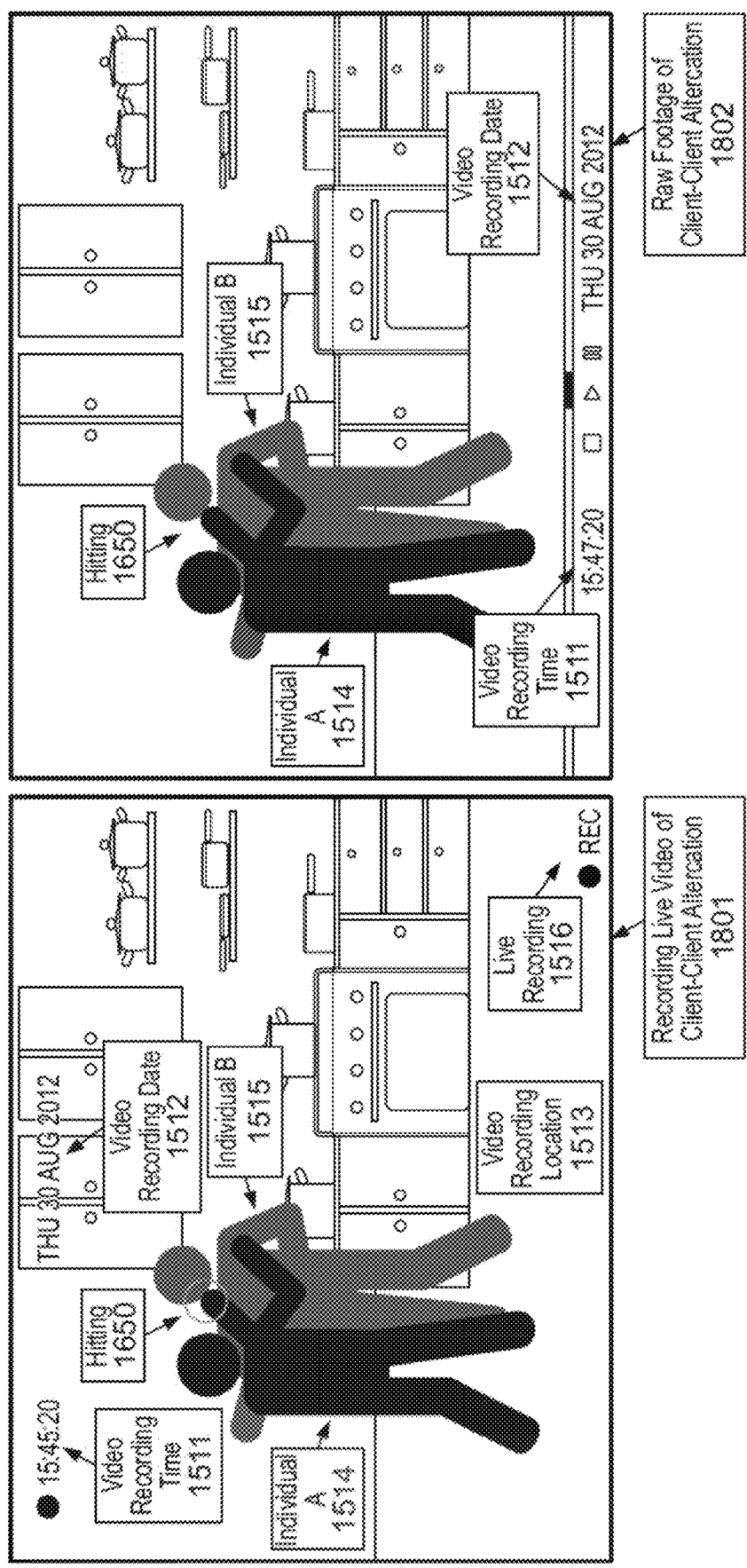
FIG. 18a represents the sample video recording of an incident of client to client altercation and the corresponding raw footage stored by the system.

In FIG. 18a, the Recording Live Video of Client-Client Altercation 1801 shows that the system is capturing the video when the Individual A 1514 was hitting Individual B 1515. The system captures the Video Recording Time 1511 and Video Recording Date 1512 and Video Recording Location 1513 as Kitchen. The system also can identify the action of hitting and store this information in the database as Hitting 1650. The Raw Footage of the Client-Client Altercation 1802 can be accessed by the person who has access privileges on both the Individual A and Individual B. For t people who has access to the Individual B but not to Individual A, the system may remove or redact the view of the Individual A from the video as shown in the Video of Client-Client Altercation for the people with access to Individual B only (Removed Individual A) 1803. Similarly, the system may adjust the video for the people who have access to Individual A but not to Individual B as shown in the Video of Client-Client Altercation for people with access to Individual A only (Removed Individual B) 1804.

Figure 18B:
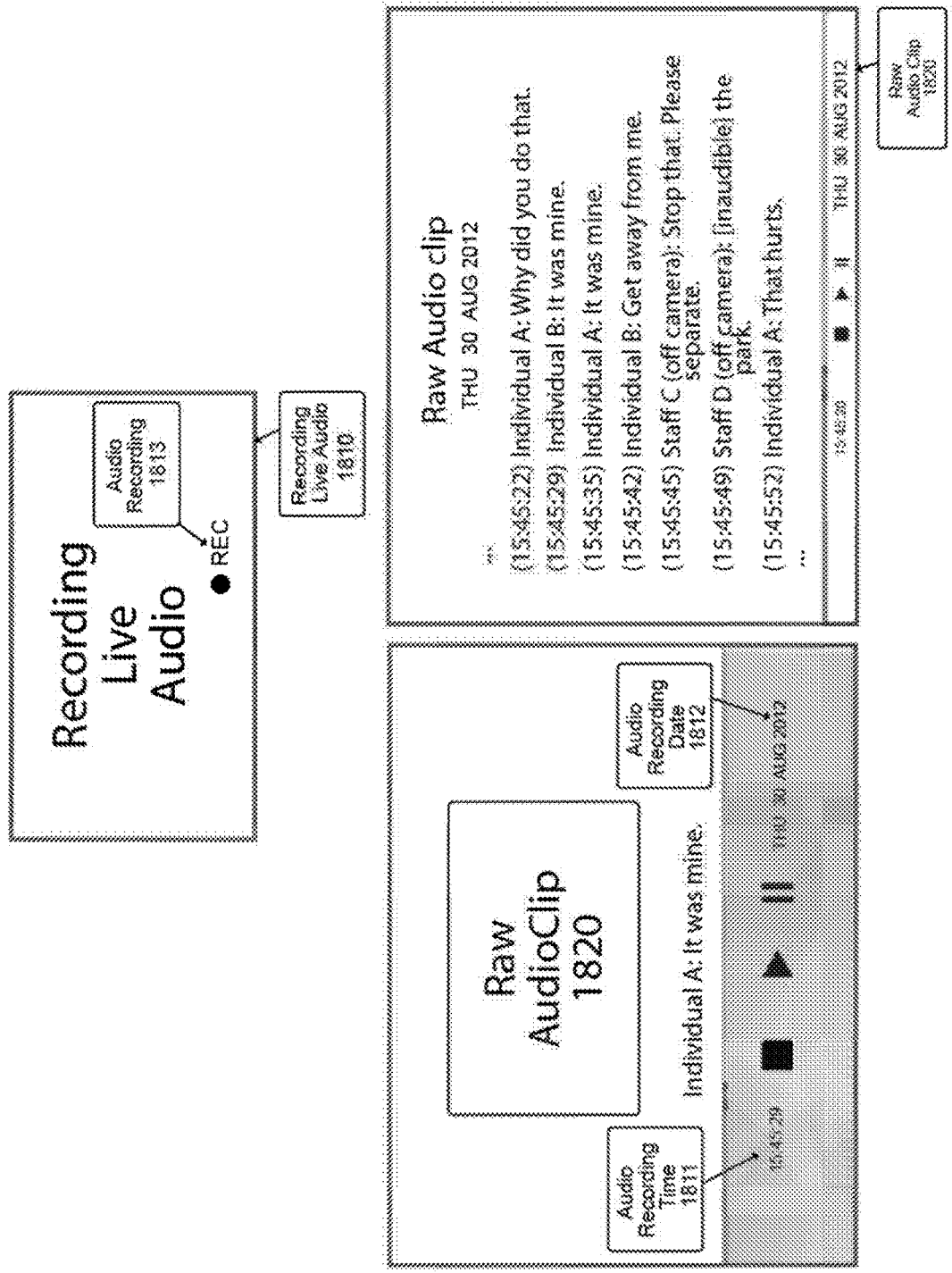
FIG. 18b represents audio recording of an incident of client altercation and the sample raw audio clip stored by the system.
Figure 18D:
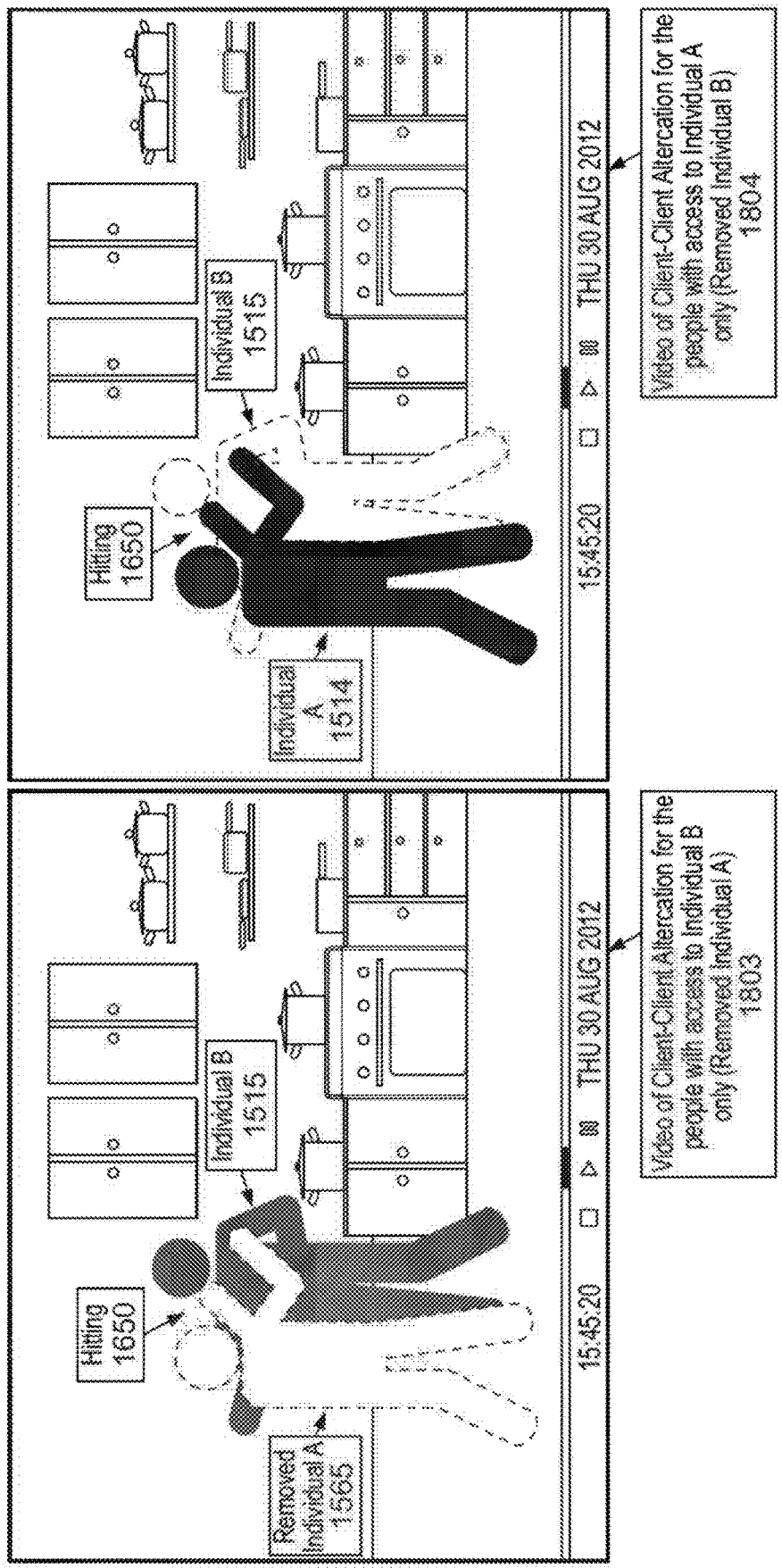
FIG. 18d represents the modified video footage of the incident of client altercation for the user with limited caseload privileges.

The system can use multiple methods to keep records of such incidents which can be used to investigate the incident. As shown in FIG. 18b, the system can record the audio of when the individuals were fighting 1810 and store this recording as the Raw Audio Clip 1820 in the database. The audio clip may contain the voice of the persons who were not captured by the system as they were present outside the range of the camera. This audio recording can be useful to identify the persons in off camera. For the people who has access to Individual A but not to Individual B, the system can remove or redact the audio of the Individual B from the raw audio clip and store in the files of the Individual A as the Audio Clip for Individual A 1830. Similarly, the system may adjust the Audio Clip for Individual B 1840 for the people with access to Individual B but not to Individual A.

Figure 19:
FIG. 19 represents the sample screenshot of creating an automated General Event Report form using the live video recording of an incident.
Figure 19B:
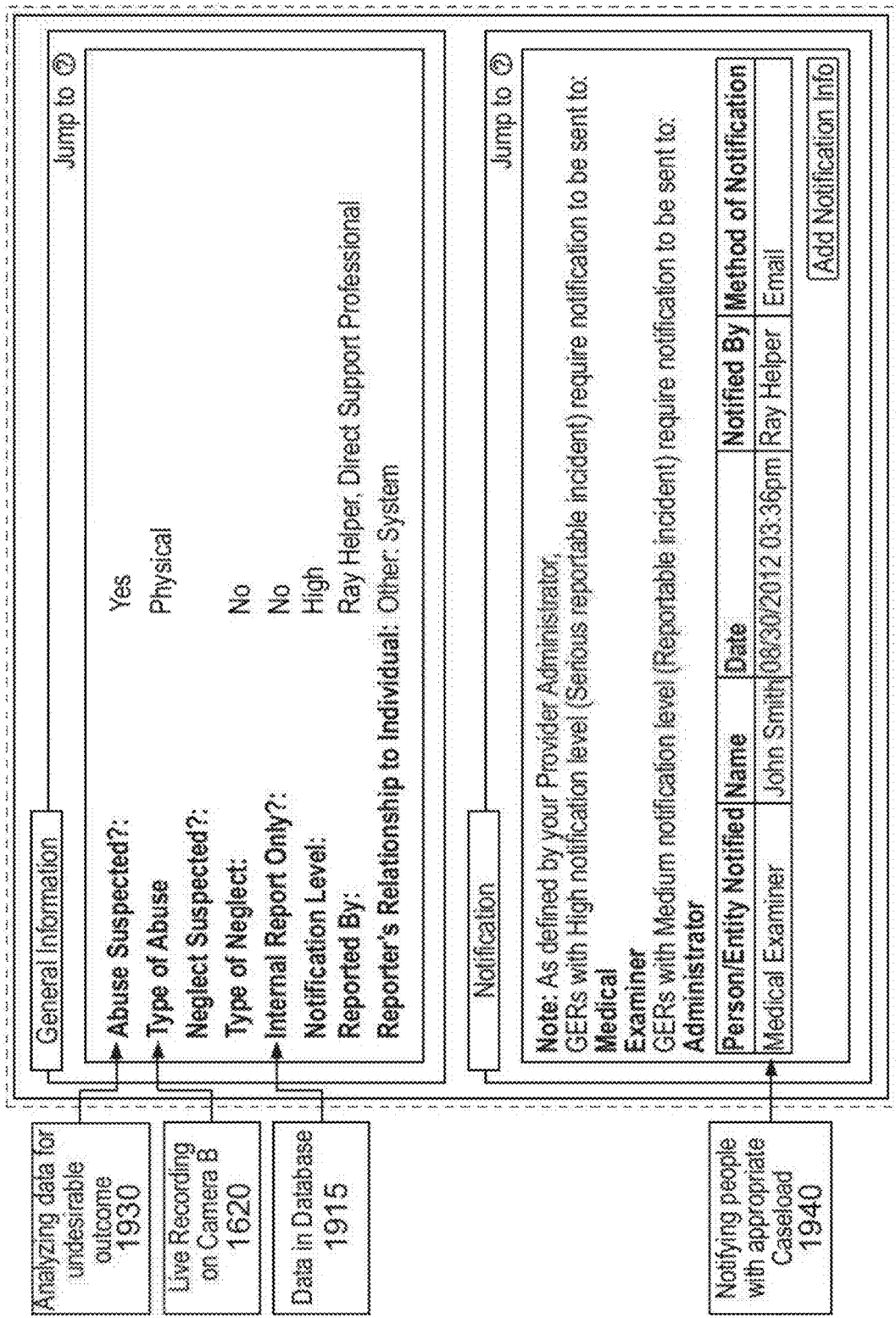
FIG. 19b represents the sample screenshot of the section of the General Event Report form where the system can automatically record notification and other information after analyzing the available real time data and generating notifications.

FIG. 19 illustrates the process of creating a form using video recording. The Incident Report also known as the General Event Reports (GER) can be used to track and record on multiple related events such as injury, medication error, death, and restraint among others. Other important information such as people notified, corrective action taken and plan of corrective actions can be entered in details. Discovered or observed incidents can be flagged, notification levels can be specified and events can be classified as it should or should not be reported to the state The system can generate an incident reporting form on an Individual on the basis of the data collected from video device which was located at the place of the incident 1513. There might be different video cameras located at different positions in the room where the Individuals are in. The system can analyze the position of the video camera which captures the best view of the incident that occurs. It performs the analysis and the mapping of information based on the data provided by that particular angle of the video camera. The video device can capture live data 1610, 1620 which is received by the system along with the recording date 1622, time 1621 and location 1513. The system can determine when there is a potential abuse on an Individual from the video footage 1930. The system then generates an incident report based on the information extracted from the video footage with no time delay and notifies people with appropriate caseloads to an immediate effect 1940. The System maintains files for Individuals. Data collected from devices both external and internal are stored in the system, analyzed and interpreted. The System identifies an individual from video or audio clips using biometrics, retina recognition, voice recognition and other demographic identifying techniques. Depending on the type of technology deployed, the system might be able to send information to the camera or device to focus or zoom in on specific individuals. For example the System could analyze the most likely cause of a negative outcome or ability to create a positive outcome and change the camera focus to best achieve or document that result. The System could record data and if there are multiple people in the video or picture provide access to the same raw data to each person's files.

For example, there might be a scenario where Individual A 1514 and Individual B 1515 are present in the living room along with Staff S 1614. There might be two video cameras in the living room at different angles, Camera A 1610 and Camera B 1620 which are recording live. Staff S then starts hitting Individual A which is recorded by both the video cameras. The system can determine which view is clearer 1620 from the video footage and records information in the system. The video feeds in the time 1621, date 1622 and location 1513 information into the system. The system has an incident reporting form where it maps necessary information regarding an incident. The system can generate a timestamp 1905 as a security feature to prevent any error or fraud. It can map the Profile information, Event Information, Injury Information as an incident, General and Notification information into the GER form for the Individual.

In the Profile Information section of the form, the system maps the Individual name, Program and Site information, Time Zone from the data in Database 1915. System also generates the 'Report Date' (System Generated Report Date 1910) in this section of the form.

In the Event Information section, system provides information previously stored in database 1920 to describe what happened before the event, location address and maps information into the 'Event Date' from the date information on Camera B 1622 and 'If not at responsible program' field from the Video Recording location 1513 information.

In the Injury Information section, the 'Injury Type' data is mapped into the form from the hitting action 1650 which is captured by the video and analyzed by the system. The system maps data into the 'Injury Cause' field by analyzing the data for the undesirable outcome 1930. The system also fills in other necessary information in the form from the data provided by the video footage.

The system analyzes the severity of the event and generates a notification level accordingly. The system can generate the notification level depending on the seriousness of the incident. That is when there is a possible abuse the report has to be considered of significantly high importance, necessary actions can be taken by the system and appropriate people can be notified. The system can generate the incident report and notify people with appropriate caseload access on the individual 1940 via mediums such as email, fax, voice message etc. The system may know which staff uses which device and informs the staff through that media.

The incident report form generated by the system can be submitted to the State by filling in additional information in a state specific information section. This data can be stored in the database which might be necessary for auditing purposes as well as for tracking goals and outcomes and progress of Individuals. Repeat occurrences of a similar event could show up as additional occurrences using the same template but being separate events. The system can have the ability to link multiple reports or events which could be tied together. But each event could be considered as a separate event as the system could analyze the similarities and differences as well as the repetitive nature of the repeat occurrence to determine recommendations.

Implementation

Figure 23:
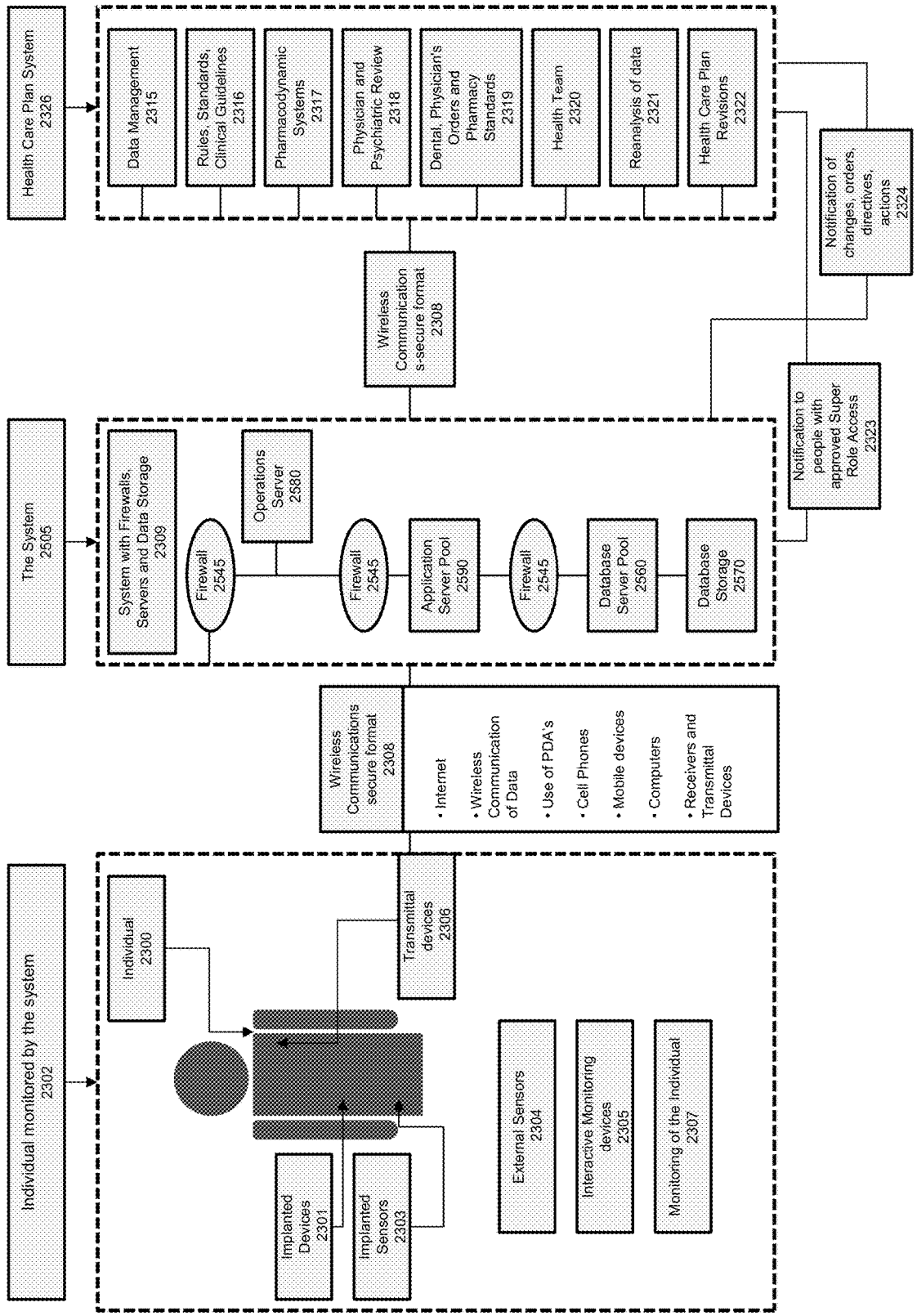
FIG. 23 illustrates the process for the implementation and monitoring of Health Care Plans for individuals.

FIG. 23 illustrates a method and system for the implementation and monitoring of Health Care Plans for individuals. The population of developmental disability has a higher rate of death from health events, and more serious conditions of disease because they are unable to communicate their symptoms. These individuals have ever changing assigned staff who is merely guessing at symptoms most of the time. The service employee or workers cannot ask if the individual is in pain, perhaps have a blocked bowel or chest pain or experiencing numbness in their legs or hands. The facts of constant change in staffing, communication issues, health issues going untreated and misdiagnosed for years, place these individuals at greater risk. The fact that these disabled individuals are frequently seen by doctors however do not appear to necessarily improve their general health care. It is evident that there is a need for an automated health monitoring and care system which can reduce need to physician visits, psychiatric visits, which can drive the health care cost to go down and which can administer medications based on pre-set orders and pharmacodynamic guidelines, both by saving staff, nursing and doctors time and reducing health events.

The Individual 2300 who is the focus of the health care plan is the person identified in the data, record and subject of analysis. This individual may be a part of a caseload of several people or a single person in a caseload. Individual Monitored by the system 2302 indicates that the Individual can have transmittal devices, such as: Transmittal devices 2306, Implanted Devices 2301, Implanted Sensors 2303, External Sensors 2304 and other devices to collect and transmit data 2305.

Interactive monitoring devices 2305 shows that the system may use a number of monitoring devices to both collect information and data for the individuals health plan: such as Living-Micro Robotic Sensors and Devices 2301, Electro Mechanical Devices, Body Implant Sensors 2303, internal, external and mobile Auto Pumps for fluids, medications, electromagnetic and chemical stimulators, External Sensors 2304, fixed and mobile sensors and monitors, which can both retrieve data and deliver treatments, medications and stimulate physical, sensory and biological systems. The health care plan may have services delivered, treatments applied by service providing entities and health care employees directly or by these interactive monitoring devices based on data analysis, provide prescriptive plans and standard health care recommendations. The individual may have data provided by these monitoring devices which indicates an alert of a health crisis: such as a heart event, diabetic event, depression, suicide, anxiety, panic attack, trauma, blood loss, infections, seizures or immediate need for treatment, intervention or evaluation.

As indicated in Monitoring of the Individual 2307, the system can provide both live ongoing monitoring, periodic, scheduled or per episode monitoring, based upon the established health care plan and physicians orders for medications, treatments and other care, however the monitoring schedule may change based on analysis of data and reanalysis of data by the system and the health monitoring may change based on changes in health status as determined by the system.

The monitoring devices and sensors can collect data on the health conditions of an Individual and feed this data into the system. These devices can feed data wirelessly to the system using internet, PDAs, cellphones, mobile devices, computers, receivers and transmittal devices and other forms of wireless devices with the help of a secured format 2308. Devices transmit data into the system. The system will analyze the data and make logical interpretations based on the data stored in the system.

The System with Firewalls, Servers and Data Storage 2309 can have Firewall 2545 to help keep the network secure, Operations servers 2580, Application Server Pool 2590, Database Server Pool 2560 to avoid the overhead of making a new database connection every time an application requires access to a database and Database Storage 2570. All these components together can compose the System 2505 which interfaces with the Health Care Plan system 2326.

The system can manage the individual's data in a secure, HIPAA compliant system and the Health Care Plan may use data for the individual that is both current, historic, based on live system data, for the individual, which may be analyzed against earlier data 2315. In addition the system can have access to and it could be possible for data collected from other individuals with similar: ethnic and racial background, age, sex, diagnosis, environmental living, DNA features, and health history data, any current medications, to assist in the health care plan analysis and for that data to be used to determine the appropriate method of treatment. Data received from Monitors, Sensors, Implanted Medical Devices, Videos, Audio Data, Mobile Sensors, Live-Micro Robotic Devices and Electromechanical Sensors, and service provider observations are entered in the Health Care Plan system. There are preset rules, standards and clinical guidelines 2316 defined in the system. Pharmacodynamic Systems 2317 within the Health Care plan system can determine the biochemical and physiological effects of drugs on the body. It might also detect the undesirable effects of a drug which might include increased probability of cell mutation, induced physiological damage, or abnormal chronic conditions. The Physician and Psychiatric Review 2318 and Dental, Physician's orders, Pharmacy standards 2319 could be preset based upon predetermined data sets, which may require changes in the individual's readings by perhaps several sensors or monitors. Opinions and reviews of the Individual's Health team 2320 which may include Case Managers, OT, PT, Speech, Wound Therapist, Immune, and Respiratory Therapist can be recorded in the system.

System can analyze data received from the individuals, external devices, internal sensors and service personnel 2321 and once the preset health conditions and standards are met, the device could be activated to make that change to their health care plan and treatment, medications or care 2322.

For example if an individual has chemical traits for a heart attack, the system may administer medications according to the pre-set orders or pharmacodynamic guidelines. If they have signs of suicide, the system could call 911 emergency systems. The system can give medications directly in preset orders or contact the physician, stimulate muscles and systems directly. The individual can have brain stimulator or stents implanted to provide for either medication or decrease blood flows etc. The system can get data from many sources, monitor large numbers of data sources for the individual and is not driven by the physician or therapist, but their preset orders, as data changes. The individual may have implanted medication devices or pumps on the belt worn on waist or arm to have the system administer directly the correct dosage to the individual and monitor the results. The system may stimulate the brain directly for depression or provide medication for anxiety or other mental health, but without asking a physician for a new order. The system can replace the need for physician visits and physician order changes by analyzing the information received from monitors and sensors and then taking appropriate measures.

The system might notify people with approved Super Role (defined below) access via a Secure HIPAA compliant wireless internet or communication system 2323 about the data changes, urgent notifications, new clinical and medical analysis, health events, crisis, positive outcomes and progress for the individual's health care plan and status. Notifications may be received on mobile devices, PDA's, Laptops, tablets, computers, cell phones, data messaging or other forms of communication devices to authorized person's for the individual.

The system might notify regarding the data changes, results of reanalysis of data including new orders, interventions, stimulations, directives, administration of required treatments or medications and other actions over a HIPAA Compliant and Secure Wireless Internet system to Service Personnel, Health Care Plan team, physicians, pharmacy, guardians, family and the clinical team 2324. The System can be capable of making decisions to notify people with appropriate caseloads and provide them with a set of guidelines. The System can make recommendations to the staff after comparing the data which has been received from external and internal devices to the data which was previously stored in the database. The System may notify staff regarding a previous medical condition of the individual and may provide them with recommendations on what future actions can be taken. The system can identify the changes in the treatment that was being received by the individual after analyzing the data received from the external and internal devices and comparing with the current data and can provide staff with a new set of orders and guidelines depending on the health condition of the individual.

Observations made by the system after analyzing data received from individuals, external devices, internal sensors and service personnel regarding the health condition of an Individual are stored in the system which can be used for future reference. The system makes changes to an individual's health care plan and treatment, medications or care depending on the pre-set orders, predetermined data sets or pharmacodynamic guidelines eliminating the necessity for physician visits and physician order changes. The system can conduct an analysis after comparing data received from implanted devices (2301) and sensors (2303) as well as from external devices (2304) continuously monitoring the individual with the data received from the Health Care Plan System (2326). This comparison can help in making necessary recommendations by the system regarding the health care plan of the individual. Treatment, medications and care plan can be modified depending on the analysis of the system. Since the system can have individual's medical history stored in the database along with other health related information such as dietary restrictions, allergy and feeding guidelines, the system can perform a detailed analysis of the individual's current health condition and make necessary alterations to the existing health plan. Besides the system can immediately respond to the emergency health condition of an individual when there is no staff around or the individual is unable to take any precautions himself. This can prevent any health hazard that might be occurring to an individual. The system can also notify appropriate staff and provide them with necessary guidelines regarding the present health condition of the individual. The staff may be unaware of the steps to be undertaken for being not physically present when the individual was experiencing critical health deteriorating symptom. The information provided by the system can assist staff to understand the scenario and take necessary measures.

FIG. 24 shows the data available in the system that can be used for analysis by the funding agencies. The system has a wide range of applications for which the data fields for the template forms have been determined according to the requirements of the funding agencies. Funding agencies may access this data and use the information for analysis 2410. The Intake Records 2420 contain the information on the oversight agency that referred an individual, the oversight ID that can uniquely identify an individual within the system, the admission date, program enrollment information and other information. The Referral process 2425 shows that data is available of when the referral was sent, when the referral was accepted and which services were mentioned during referral process of an individual. The Demographics 2421 represents that the system has detailed demographic information about each individual including the individual's medical information, contact information, insurance information. The Case Management 2422, Progress Assessment Review 2423, Lifestyle Assessment 2424, Functional Eligibility 2426, Case Planning 2427, Individual Family Service Plan (IFSP) 2430, Quality Enhancement Review (QER) 2431, Review Schedule 2432, Child PAR 2433, Case Action History 2434 represent the applications designed for the states to determine case plans, eligibility, case action, family service plan and also to assess lifestyle, progress, etc. The Outcomes, Objectives & Activities 2428, Individual Service Plan 2429 represents that the system has detailed information about an individual's goals, objective, outcomes and activities that can used for analysis and to determine the appropriate service plans. This data can also be used for determining individual budget amounts and service authorizations. For the states to investigate the incidents occurring at the entities providing supports, the system can provide the states with detailed information about the incidents that has been represented as Incident Reporting 2435. For overseeing functionalities of the states or funding agencies, data is available on Client Documentation 2436, Services Authorizations 2437, Electronic Medication Administration Record (cMAR) 2438, Billing Support 2439, System Administrative Functions 2440. The Alerts 2441 represents the information available about both the system generated and staff generated alerts. Funding agencies may use this data for analysis that may help manage individual supports and oversee the individual's' electronic documentation.

Figure 25:
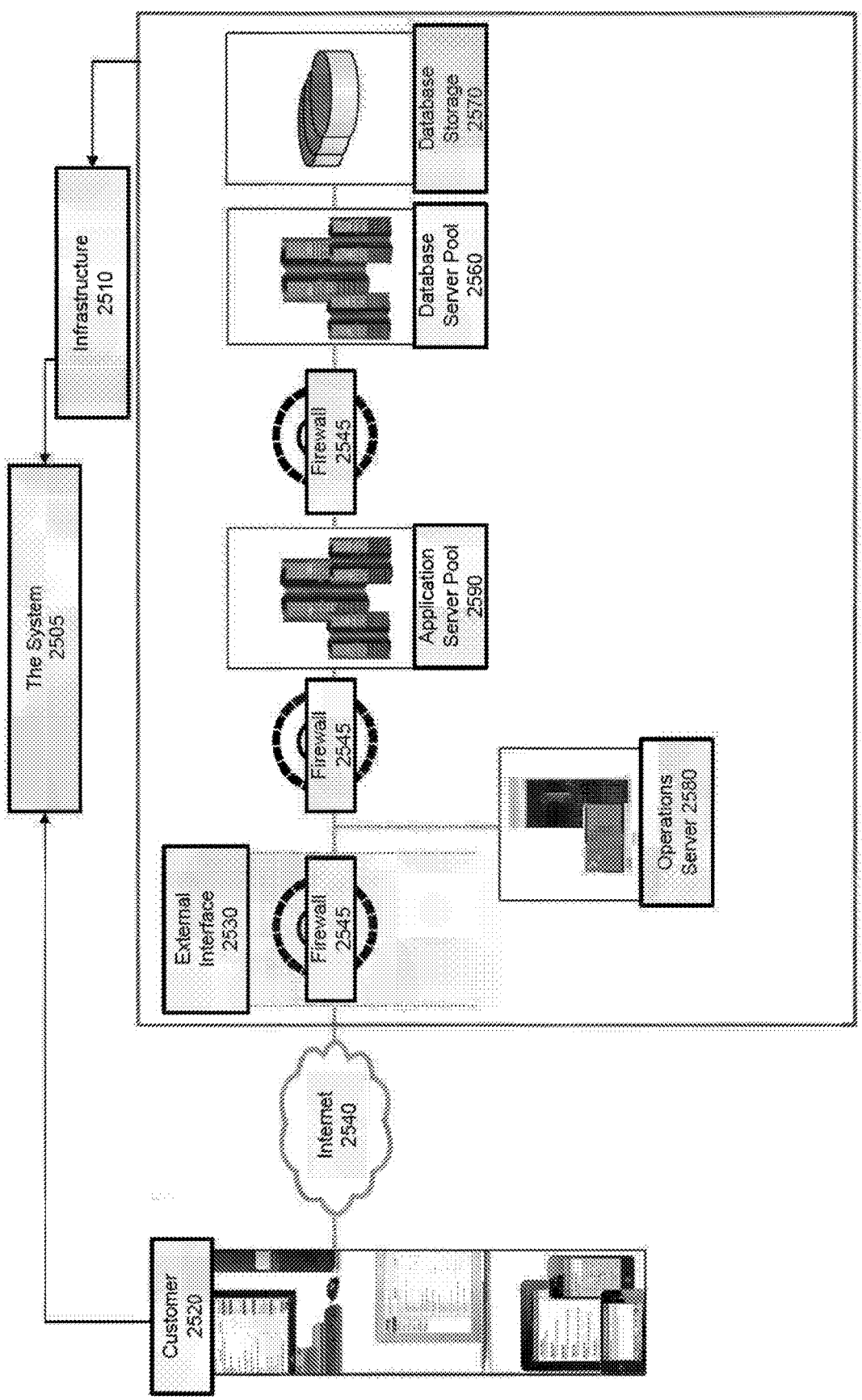
FIG. 25 illustrates the overview of the infrastructure of the system.

FIG. 25 illustrates the overall system and its infrastructure. The Infrastructure 2510 of the system 2505 is composed of Firewall 2545 to keep the network secure, Operations Server 2580, Application Server Pool 2590, Database Server Pool 2560 to avoid the overhead of making a new database connection every time an application requires access to a database and Database Storage 2570. The system might have also interface externally with other devices 2530. In the preferred embodiment, the system uses a local traffic manager for load balancing. Each site is equipped with multiple servers or nodes to handle an increasing processing load. The local traffic manager automatically detects when a server is loaded or a failure takes place at one site or equipment within a site, and can reroute traffic to the appropriate fail over server node, making sure users have access to the system and all its functionality. It preferably uses storage arrays. Within the storage array, individual or even multiple component failures of the disk drives, disk controllers, power supplies, and other elements may not cause the storage array to stop providing service or to lose any data. Further, failed components are all hot swappable so that they can be replaced while the system remains operational. It uses a database management system that runs on computers. The database technology includes many features to utilize a redundant, distributed architecture, to provide high availability and high reliability data services. Sophisticated software may be used to automatically backup all information and to maintain synchronization between sites. Data mirroring technology is used between no less than two locations. Hardware and software are used for firewalls, routing, and other security measures to prevent fraud and other invasive techniques (a.k.a. "hacking"). The system is powered by uninterrupted power supplies backed up by generators. The system preferably replicates all data in two servers in real time. In each site, data is synchronized to database backup servers and saved in offline mode to secondary storage. The customer base 2520 can communicate with the system using internet 2540 or other forms of wireless media.

Figure 26:
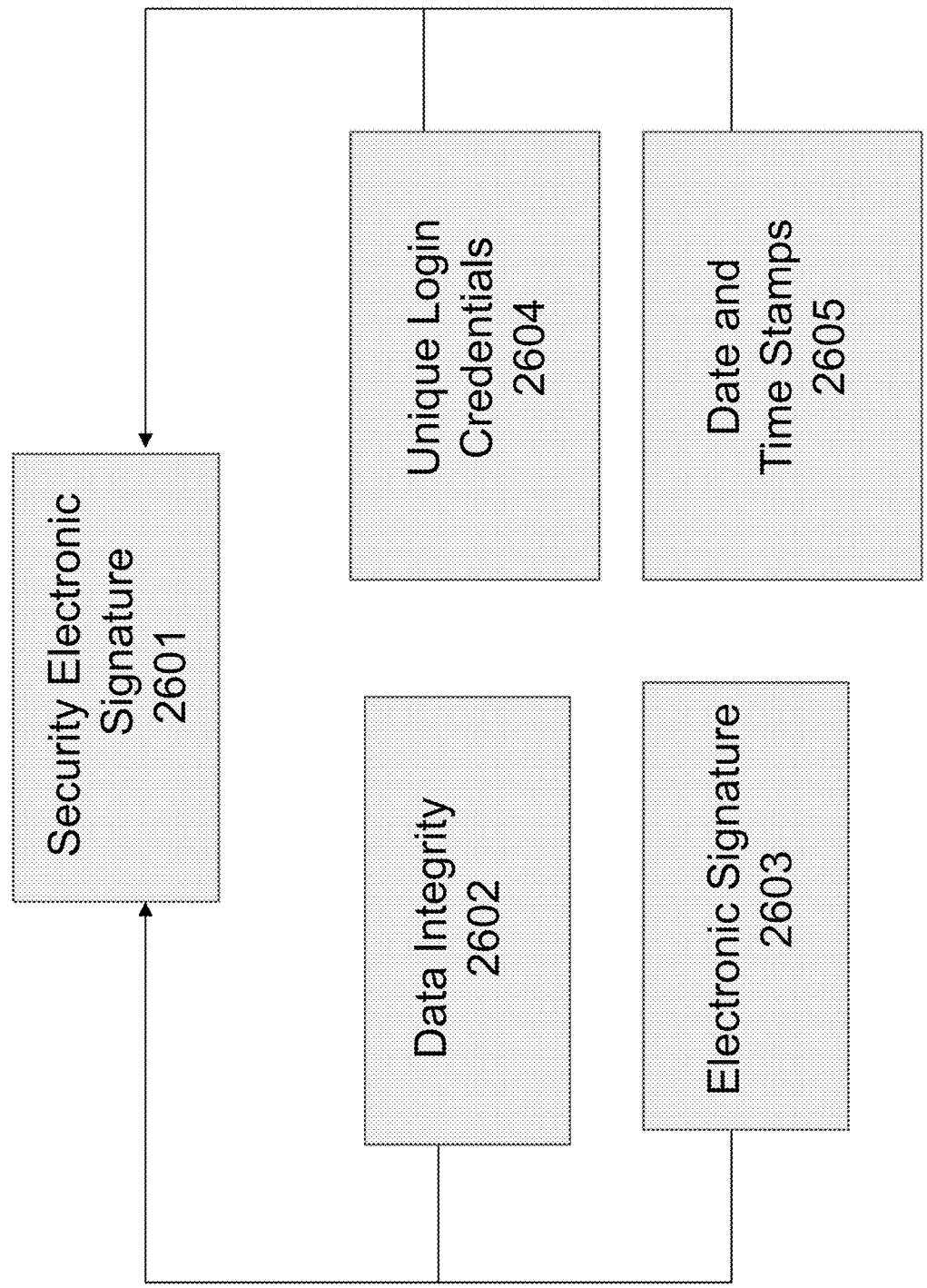
FIG. 26 illustrates the system's security feature of using electronic signature.
Figure 26A:
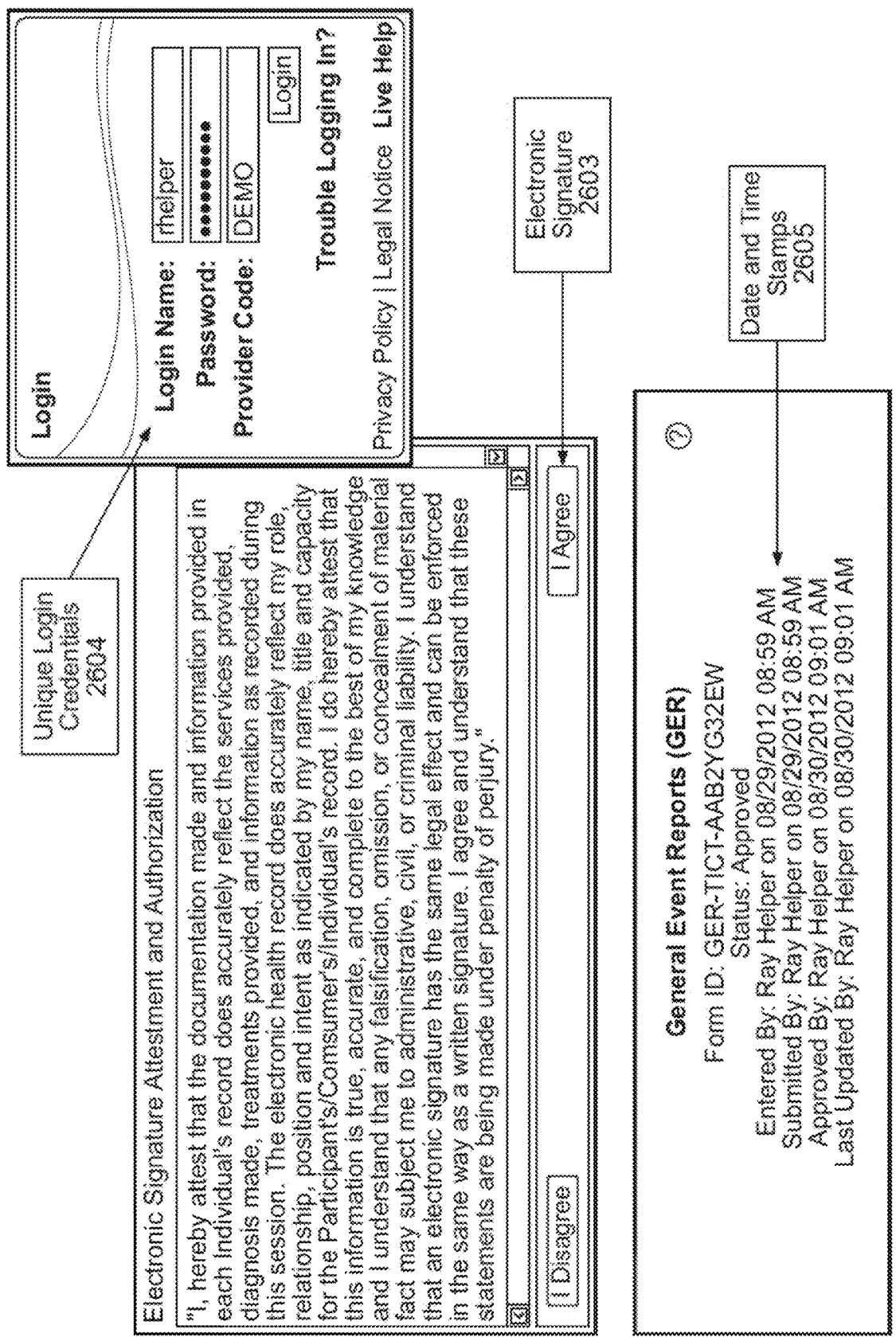
FIG. 26a represents the sample screenshot of the security feature of using electronic signature.

FIG. 26 illustrates the security mechanism of the system. The multi-level access control and unique login mechanisms of the system ensure security 2601 and authenticity of information 2602 entered into the system. Users may be assigned with Caseloads and Roles according to the agency's policy. These access privileges define the permissions that users are granted for documentation and reporting on individuals. Roles are grouped to form Super Roles that are then assigned to the users with Caseloads designed for different levels of staff.

The system also ensures data security and user accountability as all forms in the system carry the users' electronic signature 2603 along with electronic time and date stamps 2605, and other identifying information. Thus any sort of error or fraud can be traced back to the originator. The other security features of the system, like three different levels of login information 2604, password expiry feature, sign-up agreement for the users feature, etc. also ensure that data is entered into the system in a secure, HIPAA compliant manner.

Figure 27:
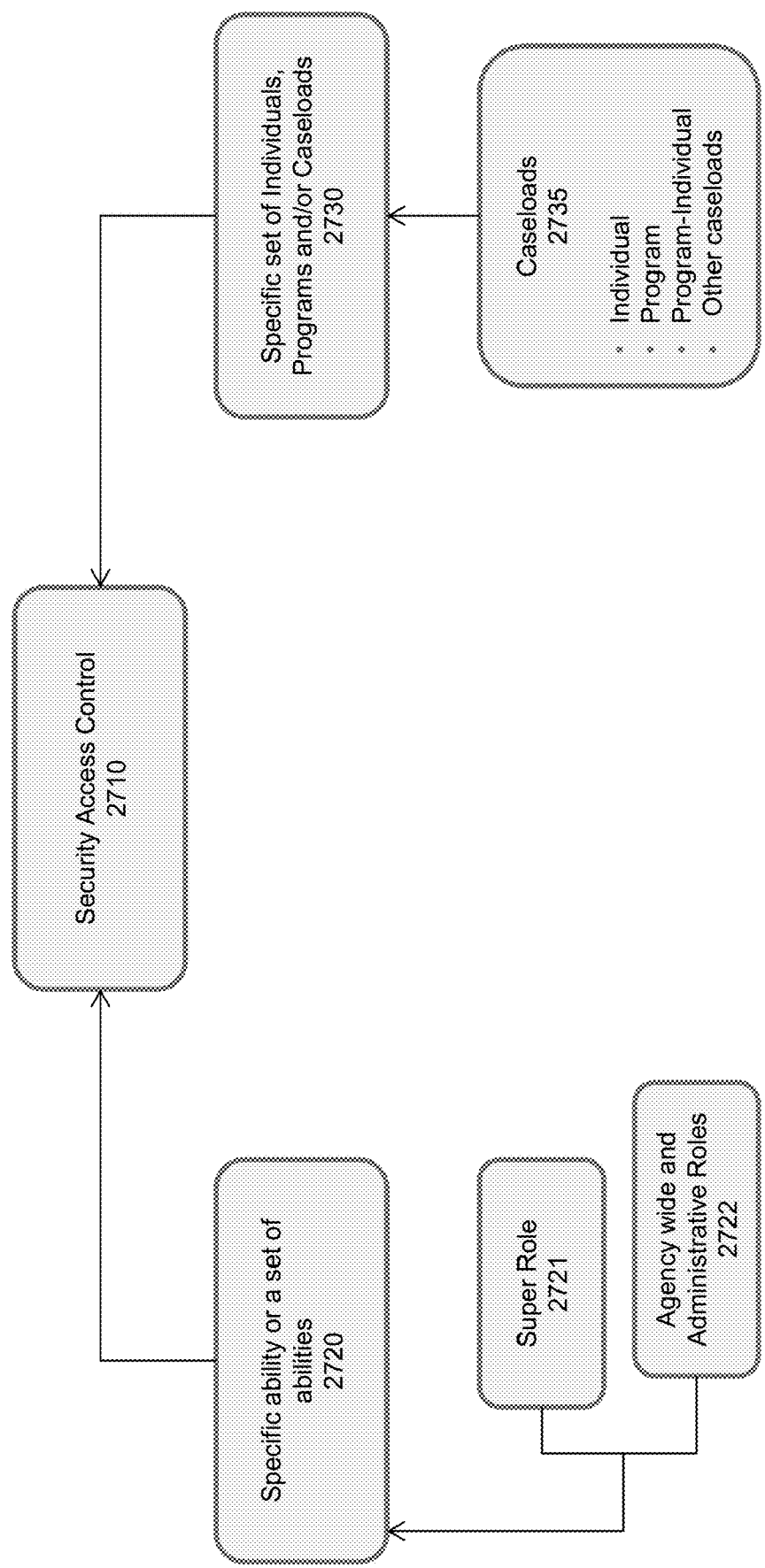
FIG. 27 illustrates the system's access control mechanism.
Figure 27A:
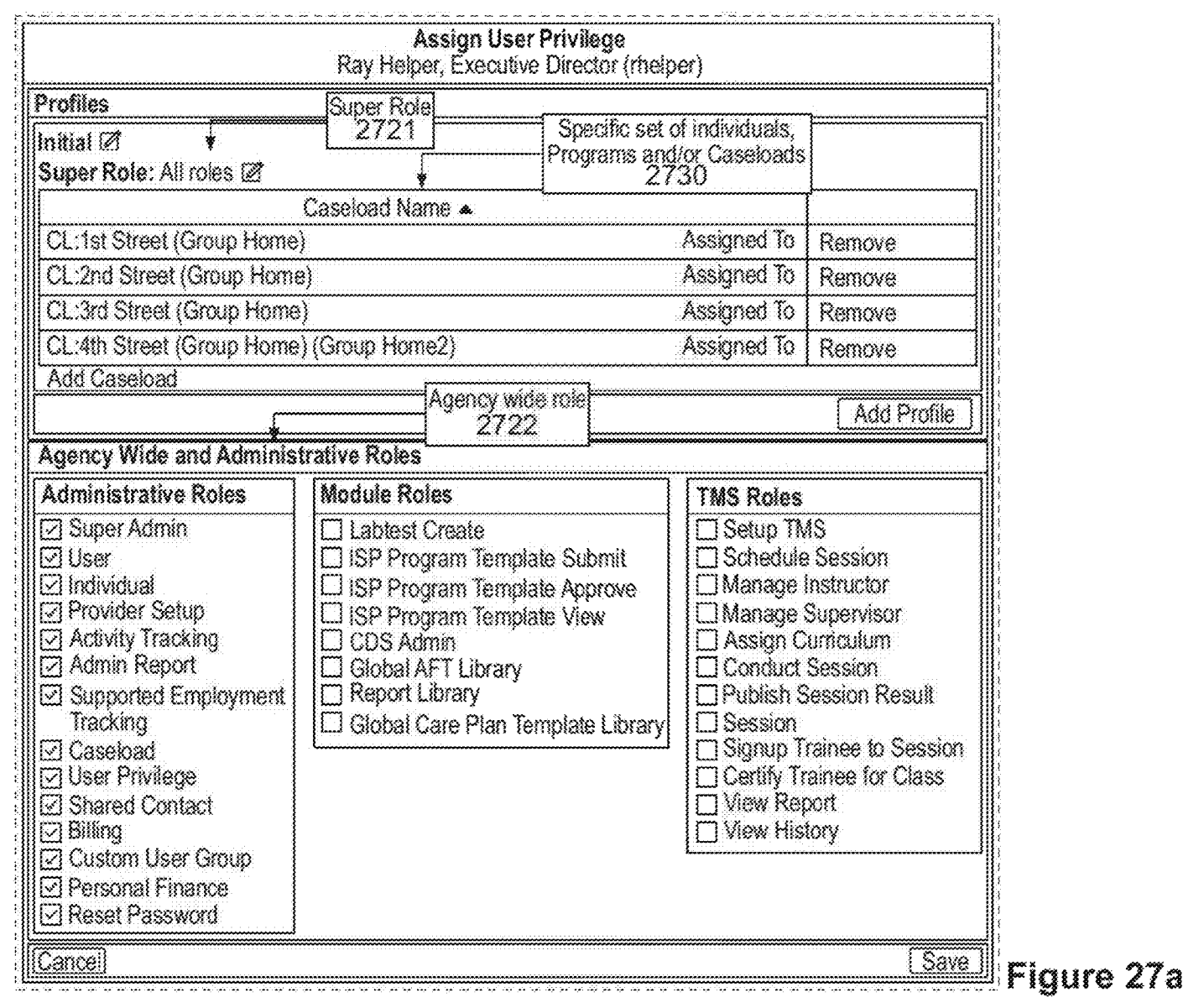

FIG. 27 illustrates the access control mechanism of the system. The Security Access Control 2710 mechanism of the system is defined with a specific set of abilities 2720 and a specific set of caseloads 2730. The access control feature of the system allows administrators to configure the access privileges of different user accounts according to the State's preferences and user job responsibilities. These features can also be used to define users' Caseloads. A Caseload defines which Individual records a given user can access (and within which settings). For example, direct support staff logging into the system can only see the Individuals that they support and a State Director might have access to all Individuals receiving support within the state. This flexibility along with the real-time availability allows a wide variety of users to access the system with appropriate rights. The system might have users who are self-advocates, families, provider staff members ranging from direct support professionals to executive directors, and a full range of state staff including service coordinators, clinicians, administrators, and surveyors. The Caseload is combined of Individual, Program, Individual-Program and Other Caseloads 2735.

The second element within defining user access is a Super Role 2721. A Super Role is a collection of capabilities or roles composed of Agency wide and Administrative roles 2722 that define what a given user or group of users can do with the data associated with their Caseloads. For example, some users may only view data and not record information, others may be allowed to enter and update data as needed. Users can access the tasks and different modules depending on the access privileges assigned to their user accounts. The access control features can be used to allow/restrict access to different applications for different user accounts.

Figure 28:
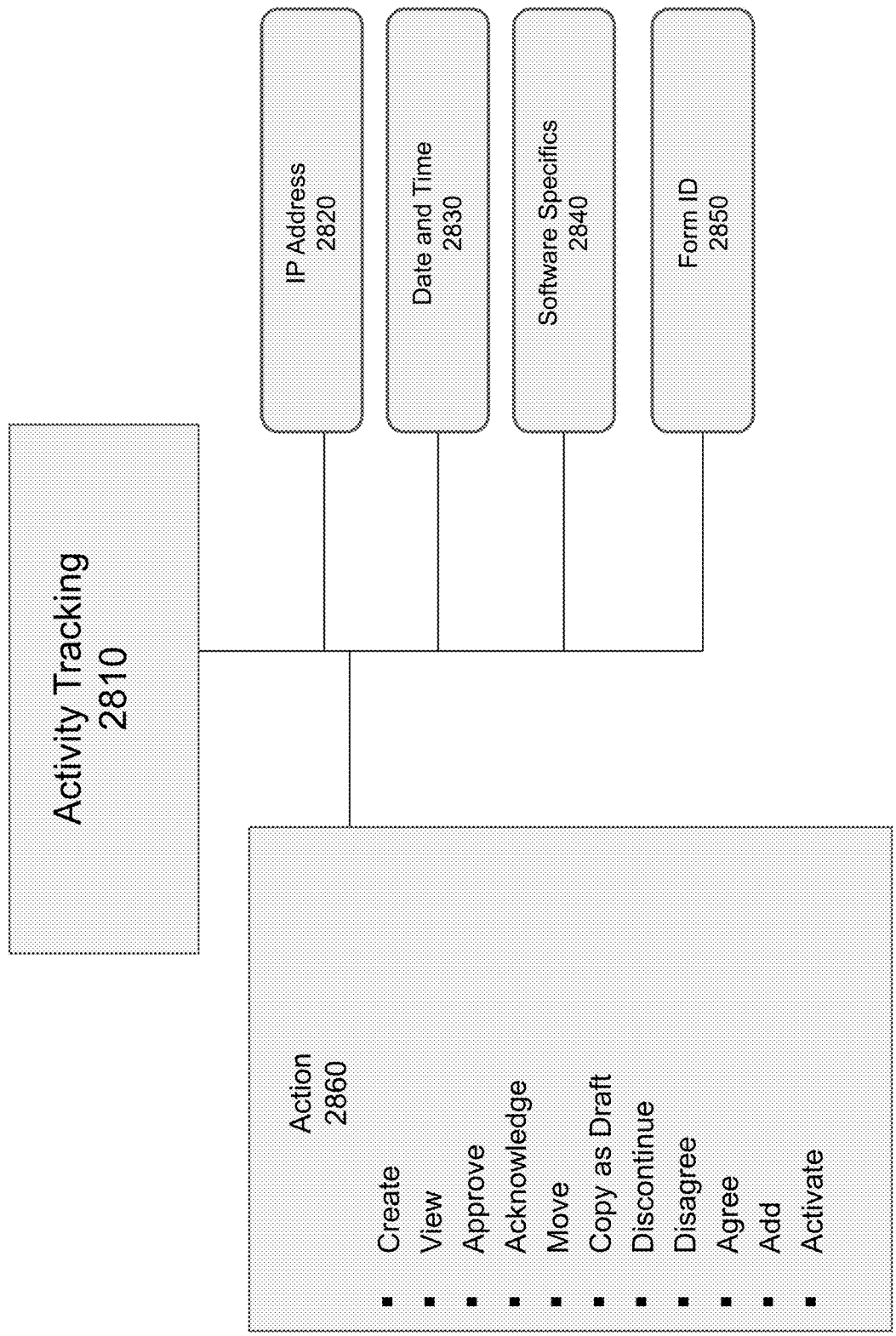
FIG. 28 illustrates the overview of how the system can track all the activities within the system.

FIG. 28 illustrates the Activity Tracking feature of the system. The Activity Tracking 2810 application keeps record of all operations performed by people using the system. This security option lets you find out who have been using the system as the IP Address 2820 is recorded, when they were using it by the Date and Time 2830 provided and for what purposes from the actions listed. It helps in auditing and monitoring of the services provided to individuals and all data entered into the system. All updates are also time and date stamped. It specifies the particular module of the system that the staff is using, activities performed 2860, name of the program and Form ID 2850. The Software specifics 2840 can also be viewed from the comments section of the Activity Tracking record. This ensures efficient auditing, enhances the security of the system and provides data necessary for verifying the activities of the staff.

Figure 29:
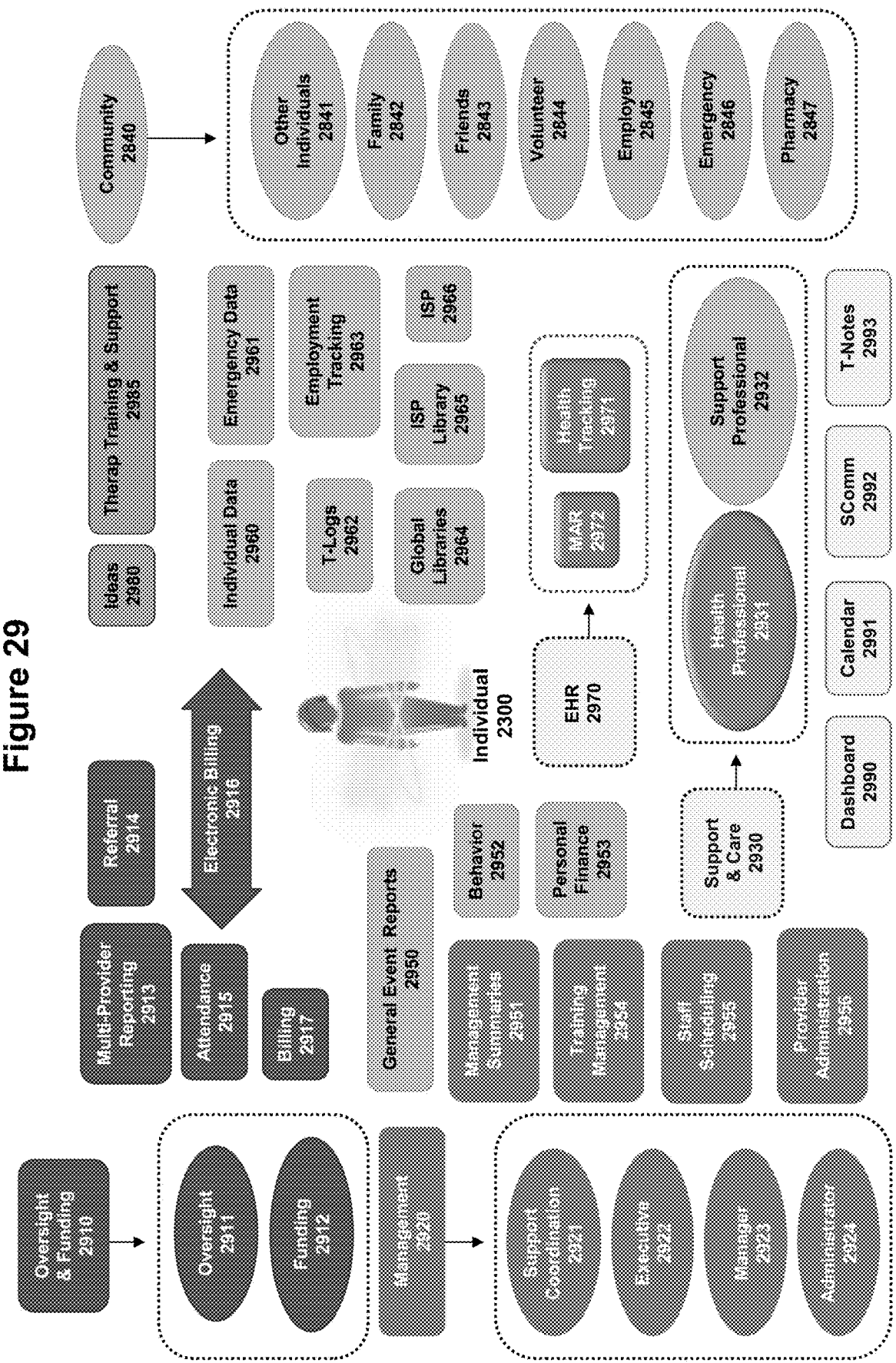
FIG. 29 illustrates the overview of person-centered data available in the system.

FIG. 29 illustrates the entire person-centered data process of the Individual in the system. The system has different set of applications for providing support to Individuals. The Individual Support Applications can consist of General Event Reports 2950 to document incidents, Behavior 2952 to track behavioral changes, Personal Finance 2953 to track financial transaction of individuals, Individual Data 2960 to record individual information, Emergency Data 2961, T-Logs 2962 to document day to day information, Employment Tracking 2963, ISP 2966, ISP Library 2965 and Global Libraries 2964. The system recognizes that the Community group 2940 of the Individual can consist of Family 2942, Friends 2943, Other Individuals 2941, Volunteer 2944, Employer 2945, Emergency contacts 2946 and Pharmacy 2947. Among the General applications which are available irrespective of any roles or privileges are Dashboard 2990 from which users can access the modules, Calendar 2991, SComm 2992 to communicate with other staff inside the agency and T-Notes 2993 or electronic sticky notes. The Individual is provided with funding reimbursements 2910 from Funding agencies 2912 and Oversight 2911 supporting Individuals to achieve their goals and objectives.

Billing Support application has been designed to help providers track services given to individuals and the amount that is to be billed for each service. It supports Electronic Billing 2916 which allows for direct submission of claims to Medicaid. Using the Billing 2917 modules users can create Service Authorizations, record Attendance 2915, track billable and non-billable service units, send single or multiple professional claims with Electronic Billing and view claim status. The Referral module 2914 is used by Oversight Agencies in order to refer an Individual for services to other linked Provider Agencies. At the end of a successful Referral process, the Individual referred is admitted by the linked Provider Agency. Besides, there is a Multi-Provider Reporting 2913 feature which provides the Oversight Agency users option to generate multiple reports on Individuals they are overseeing. These reports have been designed to meet the requirements of states and funding agencies. The Management 2920 of the agencies supporting people with disabilities is carried out by Support Coordination 2921, Executive 2922, Manager 2923, Administrator 2924 and Support Professionals 2932. The Staff Support application provides tools that facilitate the monitoring and management of information regarding staff training and certification 2954. It allows agencies to manage total work hours of employees by setting up weekly and monthly schedules 2955. Management summaries 2951 are available to generate summaries on events reported on incident forms and behavioral forms as well as Provider Administration 2956. Support and Care 2930 of the Individuals are ensured by Health and Support Professionals and the health conditions of an Individual are monitored and medications are recorded and administered by Health Professionals 2931 using the Health Tracking 2971 and Medication Administration Records 2972 applications under Electronic Health Records 2970.

Training and Support 2985 is provided to staff to help improve their efficiency in using the system as well as ideas 2980 are taken and implemented while designing further enhancements to the system.

The Person-Centered Data is securely stored in the system database and the system maintains the entire documentation process of an Individual with disabilities ensuring security and data integrity. Initially data is collected on individuals who are entered into the system based on the Individual 2300 in FIG. 4. There could be additional people with information in the system that provide support or are staff or family to the Individual 2300.

FIG. 30 shows the suite of applications of the system for Entities providing support to individuals. The Suite of applications of the system for Entities providing support to individuals 3005 can be divided into 6 major groups. Among these 6 major groups is Individual Supports 3010 consisting of basic set of applications such as T-Log, Individual Data, Emergency Data form, General Event Report, Individual Data, Individual Home Page, Witness Reports, Behavior Plan, Behavior Event Record, Individual Service Plan (ISP), Global ISP Template Library, Individual Plan of Protective Oversight and Safeguards (IPOP), Time Tracking, Advance Directives, Secure Communications (SComm), Management/Event Summaries, Demographic Report, T-Note, Calendar, Activity Tracking and Notification etc.

Then comes Staff Scheduling 3020 which helps in managing total work hours of employees by setting up weekly and monthly schedules. The Training Management System 3030 facilitates the monitoring and management of information regarding staff training and certification. The Electronic Health Records 3040 comprises of applications to track and document on Appointments, Lab Tests, Vital Signs, Blood Glucose, Height/Weight, Intake/Elimination, Medication History, Immunization Records, Infection Tracking, Menses Respiratory Treatment, Seizures, Skin/Wound, Consultation Forms and Seizures. It allows users to generate different kinds of reports including monthly, detailed and health care reports to meet the health care needs of the individual. Besides, the administration of medications can be recorded and tracked on a regular basis using the Medication Administration Records module. There are also applications documenting the allergies of an individual using the allergy Profile and recording the diagnoses, treatment preferences and care plan of an Individual. A comprehensive report on the health condition of an Individual can be generated using the Health passport of that Individual. The Personal Finance module 3050 can be used to track financial transactions such as Expenses, Deposits and Account Balances for an individual. The Billing module 3060 keeps information about funding sources, billable services provided by programs at the agency and service authorizations and attendance for different individuals. The application includes the option to prepare bills for services provided to individuals. It also gives users the option to view the billing information in a summarized form of choice. The Billing Support application also supports Electronic Billing which allows for direct submission of claims to Medicaid.

Figure 31:
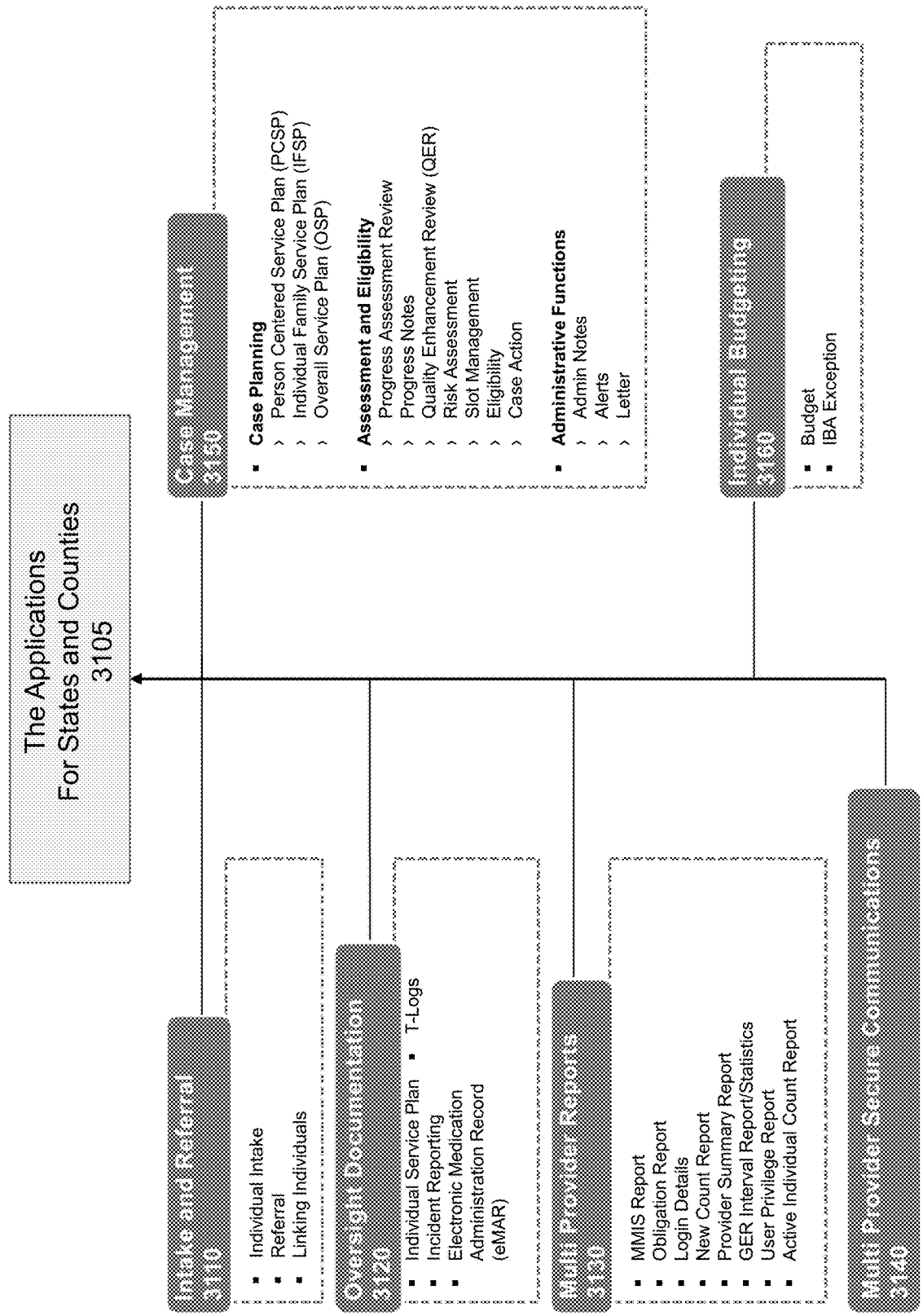
FIG. 31 illustrates the overview of the suite of applications that have been designed for the states and counties.

FIG. 31 shows the applications available for the States and Counties or Funding Agencies. In FIG. 31, The Intake and Referral 3110 represents the Individual Intake, Referral and Linking Individuals applications that have been designed according to the requirements of the States and Counties or Funding Agencies. These applications allows to intake individuals into the system and refer them to other Entities Providing Support 250. Once the referral is sent to the other entries the system creates an instance under each entity file in the database. The system assigns unique Oversight ID to link each instance. The Oversight Documentation 3120 represents that the system allows the State, Counties or other Funding Agencies to oversee the T-Logs or shift logs created for the individuals, Individual Service Plans, Incident Reports, Electronic Medication Administration Records and other health care reports. The system may provide a number of Multi Provider Reports 3130 that include MMIS Report, Obligation Report, Login Details, New Count Report, Provider Summary Report, GER Interval Report/Statistics, User Privilege Report, and Active Individual Count Report. The system also allows Multi Provider Secure Communications 3140 that can be useful for communication between the Entity Providing Support 250 and the States, Counties or other Funding agencies in a secure and HIPAA compliant way. The Case Management 3150 represents the management tools that include Person Centered Service Plan, Individual Family Service Plan (IFSP), Overall Service Plan (OSP), Progress Assessment Review, Progress Notes, Quality Enhancement Review (QER), Risk Assessment, Slot Management, Eligibility, Case Action, Admin Notes, Alerts, Letter. The Individual Budgeting 3160 represents the application that may help the States and Counties or Funding Agencies create the budget amount and respective service authorizations for the individuals.

Figure 32:
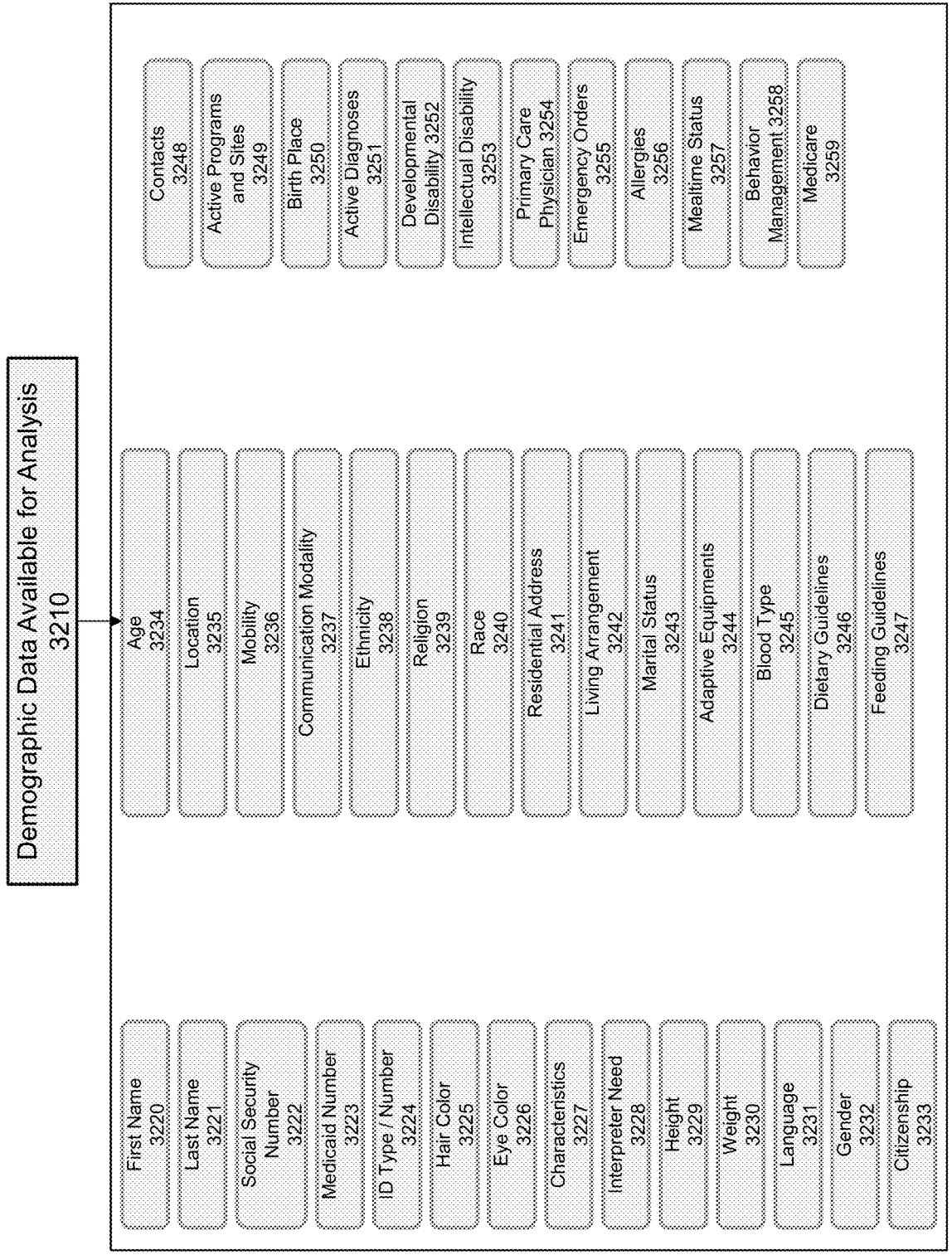
FIG. 32 illustrates the overview of the demographic data available in the system which can be used for analysis.

FIG. 32 shows the demographic data available in the system that can be used for analysis. While entering data for an individual into the system, it captures the detailed demographic information about the individual either directly from the individual or from family or staff member or other available sources. The Demographic Data Available for Analysis 3210 contains First Name 3220, Last Name 3221, Social Security Number 3222, Medicaid Number 3223, ID Type/Number 3224, Hair Color 3225, Eye Color 3226, Characteristics 3227, Interpreter Need 3228, Height 3229, Weight 3230, Language 3231, Gender 3232, Citizenship 3233, Age 3234, Location 3235, Mobility 3236, Communication Modality 3237, Ethnicity 3238, Religion 3239, Race 3240, Residential Address 3241, Living Arrangement 3242, Marital Status 3243, Adaptive Equipment 3244, Blood Type 3245, Dietary Guidelines 3246, Feeding Guidelines 3247, Contacts 3248, Active Programs and Sites 3249, Birth Place 3250, Active Diagnoses 3251, Developmental Disability 3252, Intellectual Disability 3253, Primary Care Physician 3254, Emergency Orders 3255, Allergies 3256, Mealtime Status 3257, Behavior 3258, Management, Medicare 3259.

Figure 33:
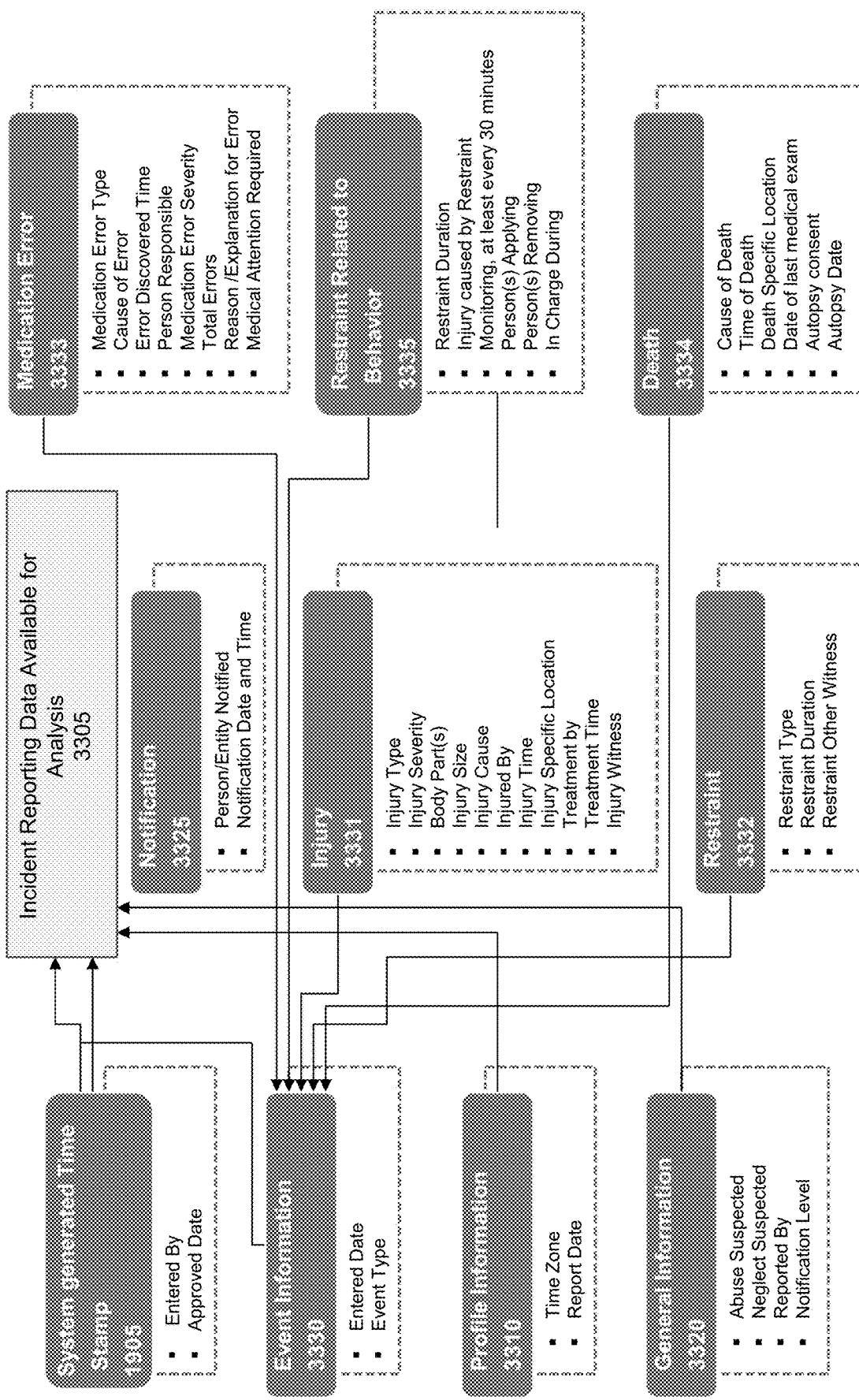
FIG. 33 shows the incident reporting data available in the system for analysis.

FIG. 33 shows the Incident Reporting Data available in the system for analysis. The incident reporting form can precisely document information regarding an incident occurred to an Individual. It has been designed to track multiple related incidents for an individual. The incident reporting tool referred to as the General Event Reporting tool also known as GER, can be used by users to report and follow-up on a wide range of incidents that include injuries, behavioral concerns and accidents among others.

GER also lets users track the comments of witnesses for each event. By simply entering the names of witnesses in a GER, users may get links to witness reports which can let them review detailed comments on what was witnessed during an incident. Other important information such as people notified, corrective action taken, and plan of corrective actions can be entered in details. Users can review the information prior to approval and follow up later once a GER has been approved. The GER has also been integrated with the Behavior module to facilitate the reporting of incidents that involve restraint as a result of behavior. Many of these incidents often need to be reported to the state in state-specified formats. The GER module has been made flexible to allow users to complete state specific incident reports.

Among the various sections of the GER form, the Profile Information section 3310 lists the Individual name, Program Information, Time Zone and Report Date. Then in the Event Information 3330, section users can record information regarding details of the incident that has occurred. There are options for recording different types of events such as Injury 3331, Medication Error 3333, Restraint related to behavior 3335, Restraint Other 3332 and Death 3334. In the Injury event information page 3331, information can be filled out regarding the injury type, injury cause, time of injury, specific location where the event occurred and whether the event was discovered or observed. Details regarding the size of the injury, severity, body parts and summary can also be entered into the form. Injury photo can also be attached with this form.

While entering the medication error information 3333, users can specify the type, severity, error discovered date, total errors, time of initial error, total errors and reason for errors. The system can notify appropriate users regarding the incident and can keep a record of the name of the person who was notified, date and time of notification.

Users can mention the restraint related to behavior event status, restraint duration, and person in charge during the event and if there was any injury caused due to restraint in the Restraint related to Behavior section 3335.

In the Restraint Other Information section 3332, user can specify restraint type, duration, specific location and summarize the entire incident.

Users can also specify a death event 3334 by mentioning specifics such as cause, time, location, date of last medical exam, autopsy date, consent and other comments. Users can also enter the details of incidents that do not come under the above mentioned categories in the Other event information section.

In the General Information section 3320 users can identify whether an incident is of abuse/neglect type, whether the data should be made internal/external to the agency, the notification level of the report.

Users are able to notify appropriate people using the Notification section 3325 and can fill out state specific information required by particular states from the State specific information section. Users can also specify the actions taken/planned, add review and follow-up comments and add any external attachments using the GER form. If abuse and neglect is suspected, certain notifications are required to be made by law or policy. According to the agency or oversight or government rules, there might be preset limits to who can access and see the data on individuals. The system can also have the ability to preset limits on who can access these data. Certain reinterpretations can be triggered by the system relating to data regarding the staff or the individual involved. For example staff can be reassigned, policies can be adjusted, additional training can be mandated, staff can be placed on leave, and the individual might be taken to a specialist, all depending on the data and analysis performed by the system. As the system has data about the individual and staff member and can also analyze across multiple caseloads, the system can provide interpretations and analysis for recommendations or can take certain actions.

Figure 34:
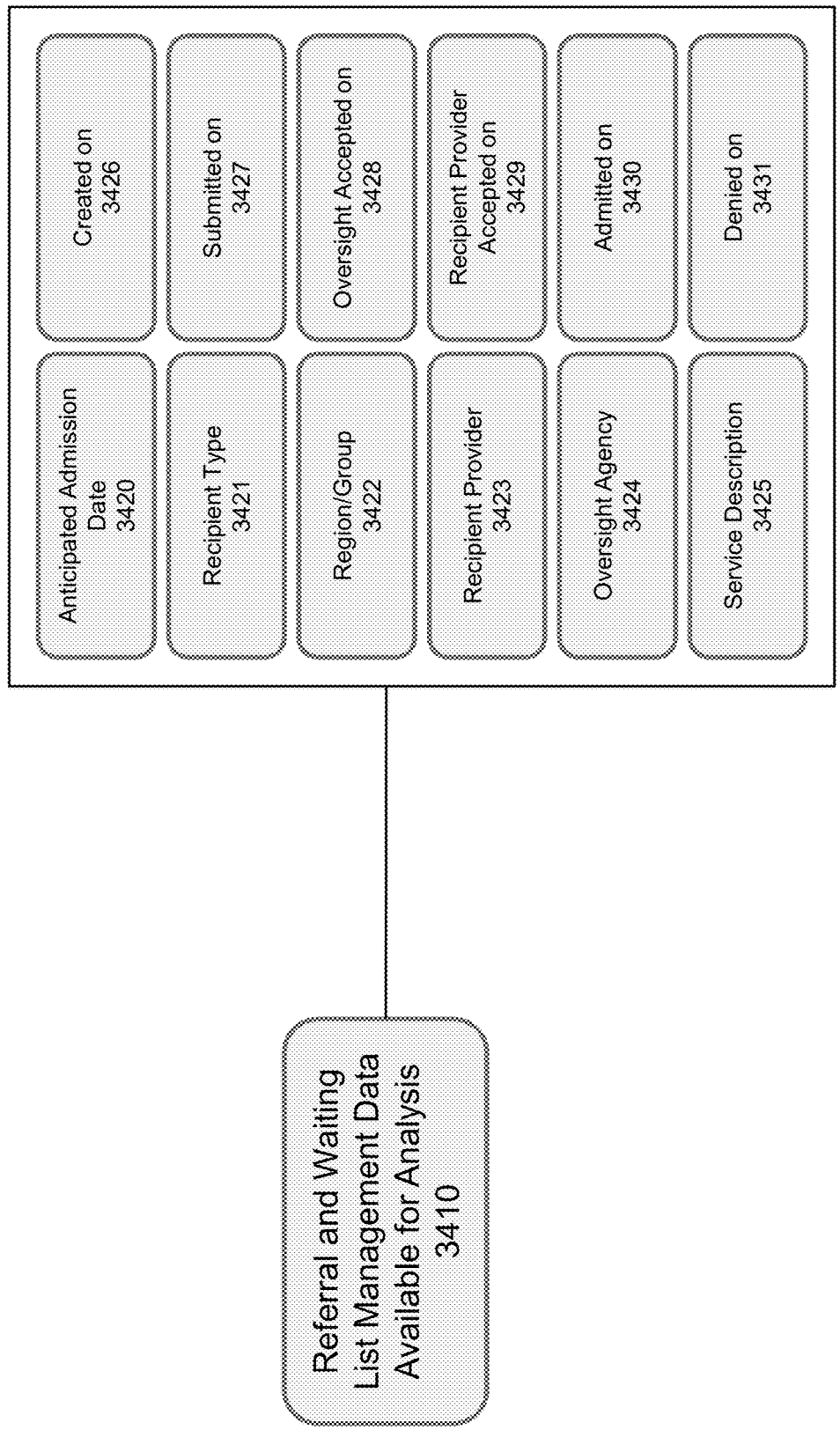
FIG. 34 illustrates the overview of the referral and waiting list management data available in the system which can be used for analysis.

FIG. 34 shows the referral and waiting list management data available in the system that can be used for analysis. Using the system the states, counties or funding agencies may send electronic referrals for the individuals to other entities. The system has detailed information on the referral process which can be used for analysis. The Referral and Waiting List Management Data Available for Analysis 3410 shows the data obtained from the Applications for States and Counties 3105. This data can be used to analyze the referral and admission status of individuals under Entity Providing Support 250. The data available for the analysis of the referral process includes Anticipated Admission Date 3420, Recipient Type 3421, Region/Group 3422, Recipient Provider 3423, Oversight Agency 3424, Service Description 3425, Created on 3426, Submitted on 3427, Oversight Accepted on 3428, Recipient Provider Accepted on 3429, Admitted on 3430, and Denied on 3431. The system also has the details of the services that were mentioned at the time of sending referral and also the documents on the individual's previous history that were sent along with the referral. If any entity denies a referral, the system collects the information about the reason for denial. Using all this information the system can determine if individual has been referred to, which entity can be providing support to the individuals and what the status of the referral is. If an individual's referral is denied by an entity then the state, counties or funding agencies may analyze the denial reasons to determine the entity to be chosen for the next referral. This analysis may help the states, counties or funding Agencies manage their referral process.

Figure 35:
FIG. 35 illustrates the process of entering an automated Attendance Data form using the video recording of an activity program.

FIG. 35 illustrates the process of creating an automated Attendance form using the live video recording of an activity program. In FIG. 35, different fields on the Attendance Data form has been filled in by the system using information captured in the video recording of the activity program. As shown by FIG. 17, the system can capture the raw view of the individual as Individual B 1515, Staff S 1614 and the location where the camera is located as Video Recording Location 1513. For the Toothbrushing Program this location is the activity room. This information can be mapped with previous records to identify the individual within the system and to locate the Provider Program and Service Description Code for which Individual B 1515 is attending the Toothbrushing Program. Using this information the system can enter the Attendance Data for the Individual B. In FIG. 35 the Automated Attendance Data 3520 shows that the system can determine the attendance input data using the presence of the Individual B in the video recording. The system can enter the information that the individual was present during the Toothbrushing Program. The Attendance Time determined by System 3115 represents the time of when the Individual B's presence was detected by the system, till the time of when Individual B left the activity room.

Figure 36:
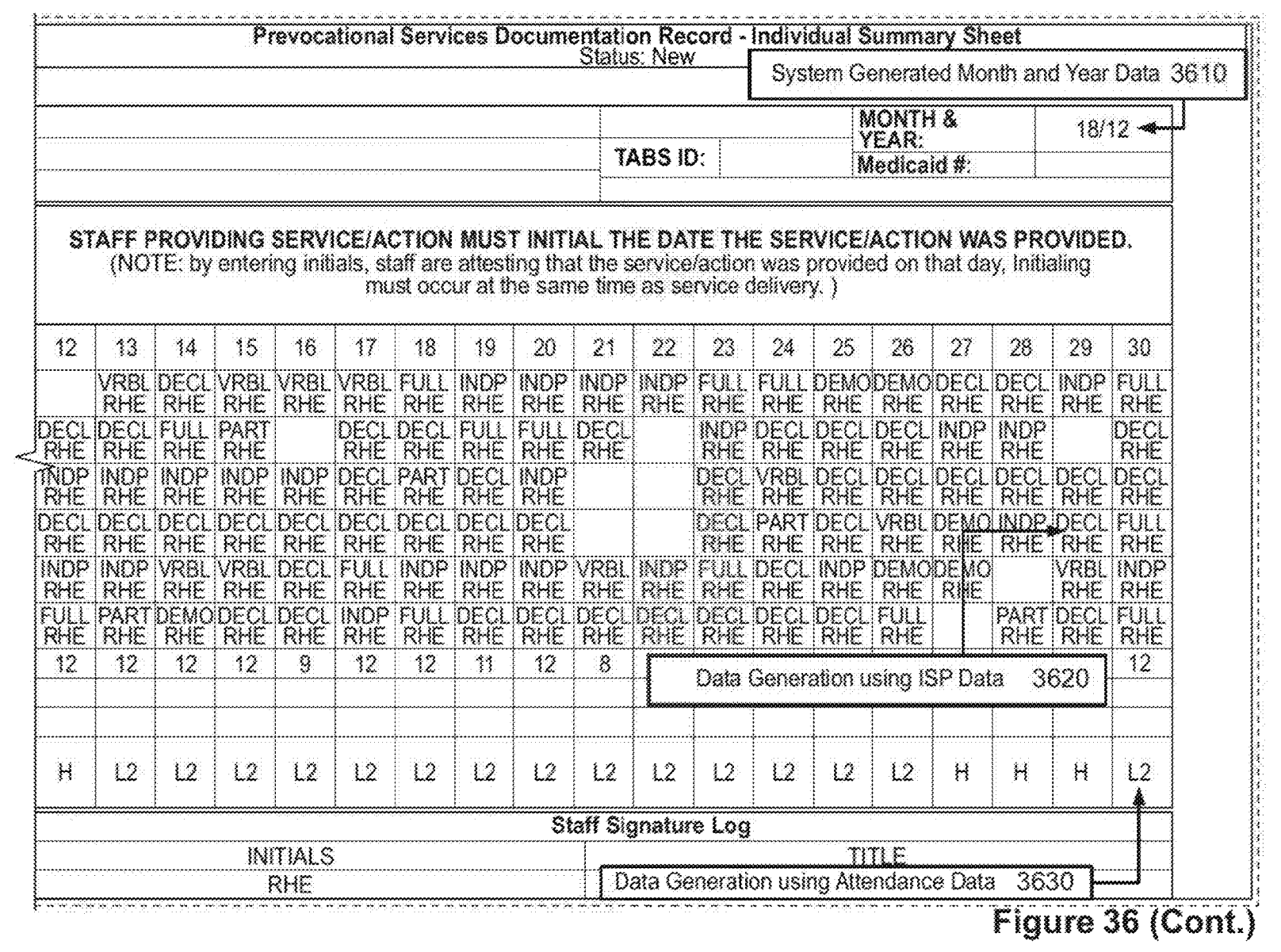

FIG. 36 illustrates the process of creating an automated Hab Checklist form using the video recordings of the activity program. In FIG. 36, the Hab Checklist data can be generated by the system using both the automated ISP Data and Attendance Data. Using the data captured in the live video recording the system can automatically generate the ISP Data and Attendance as shown by FIG. 22 and FIG. 35. The sample screenshots of the automated Hab Checklist shown in FIG. 36 represents that after generating the automated ISP Data and Attendance Data the system may generate the Hab Checklist data for the System Generated Month and Year Data 3610. For example, if it is the end of the month of August then after generating the ISP and Attendance Data for August 30 the system can generate the Hab Checklist for the month of August using all the previous ISP and Attendance data and also the newly generated ISP and Attendance Data. The Data Generation using ISP Data 3620 represents that the system maps all the ISP Data saved for the Toothbrush Program for the month of August and analyze the data to determine if services have been provided to the individuals following staff actions defined in the habilitation plan form. Then the system generates the Hab Checklist data for the person who had entered the ISP Data for each of the staff actions. The Data Generation using Attendance Data 3630 represents that the system can map Attendance Data with the ISP Data and do further analysis to determine Hab Checklist data for the duration of service delivery.

It will be understood by those of ordinary skill in the art that various changes may be made and equivalents may be substituted for elements without departing from the scope of the invention. In addition, many modifications may be made to adapt a particular feature or material to the teachings of the invention without departing from the scope thereof. Therefore, it is intended that the invention not be limited to the particular embodiments disclosed, but that the invention will include all embodiments falling within the scope of the claims.

What is claimed:

1. An improvement to the way that computer systems operate to provide HIPAA-compliant access of a user to electronic personal health information of an individual under care, the improvement comprising a HIPAA-compliant computer security method of recording visual personal health information in an electronic format relating to at least two individuals, at least one of whom is the individual under care, from a video camera, preventing unauthorized access of the user to the information, and initiating preventative action, comprising:

storing records of physical attributes of the individual under care and the one or more individuals other than the individual under care;

recording electronic video signal personal health information, via a video camera, including physical attributes of the individuals;

transmitting at least a portion of said video information to a computer system with a memory and a processor;

storing, by said computer system, at least a portion of said transmitted video information;

storing, by said computer system, at least one authorization profile associated with the user, wherein the user is associated with one or more roles and one or more caseloads and the caseloads include access privilege information for the individual under care, wherein said user access privilege information included in said user's caseload includes the identities of individuals under care to which the user has access;

determining, by said computer system, whether said user is permitted to view said information pertaining to a caseload of the individual under care, wherein the determination is based on said authorization profile and the one or more caseloads and the one or more roles associated with the user, wherein said determining includes:

comparing the stored records, of physical attributes of the individual under care and the one or more individuals other than the individual under care, to the stored video information, identifying a portion of said stored video information pertaining to the one or more individuals other than the individual under care by matching at least one of a face, eye color, and/or hair color in the stored records of physical attributes of an individual other than the individual under care with the face, eye color, and/or hair color of an individual other than the individual under care in the stored video information, identifying a portion of said stored video information pertaining to the individual under care by matching at least one of a face, eye color, and/or hair color in the stored records of physical attributes of the individual under care with the face, eye color, and/or hair color of the individual under care in the stored video information; and comparing the identity of the individual under care to the user's authorization profile information, including comparing the identity of the individual under care to the user's caseload, and granting access to the user to said portion of said stored video information pertaining to the individual under care if the identity of the individual under care is stored in the user's caseload; and blurring, by said computer system, said portion of said stored video information pertaining to the one or more individuals other than the individual under care, wherein the entire image of the one or more individuals other than the individual under care is blurred, and wherein said blurring is done prior to any human viewing said stored video information;

transmitting, by said computer system, said portion of said stored video information pertaining to the individual under care, and said blurred portion of said stored video information pertaining to the one or more individuals other than the individual under care, to said caseload of said individual under care for HIPAA-compliant viewing by said user authorized to view said portion of said stored video information pertaining to the individual under care;

wherein at least a portion of said stored video information pertains to an initial inquiry relating to one or more goals of the individual under care;

storing, by said computer system, historical information, wherein said historical information pertains to said initial inquiry relating to said individual's care;

comparing, by said computer system, said historical information and at least a portion of said stored video information;

determining, by said computer system, a first interpretation of at least a portion of said stored video information based on said comparison;

determining, by said computer system, whether said first interpretation indicates a likelihood of negative outcome for said one or more individuals;

determining, by said computer system, based on said indicated negative outcome, a first preventative action relating to said first indicated negative outcome; and transmitting, from said computer system, a signal for initiating said first preventative action.

2. A computer security method according to claim 1, wherein:

said storing records step further includes storing information regarding the identity of at least one program in which the individual under care is enrolled; said stored user access privilege information included in said user's caseload includes the identities of at least one program to which the user has access;

said determining step further includes the steps further includes the step of comparing the identity of the programs in which the individual under care is enrolled to the user's authorization profile information, including comparing the identity of the individual under care to the user's caseload, and granting access to the user to the portion of said stored video information pertaining to the individual under care if the identity of the program in which the individual under care is enrolled is stored in the user's caseload.

3. A computer security method according to claim 1, wherein said negative outcome includes one or more instances of abuse and neglect.

4. A computer security method according to claim 1, wherein said recorded information includes one or more of said one or more of the thoughts, feelings, or responses to questions of the individual under care.

5. A computer security method according to claim 1, wherein said at least a portion of said information is recorded via an electronic sensor.

6. A computer security method according to claim 5, wherein said electronic sensor is capable of recording one or more of voice, facial expressions, hand movements, words, biometrics, typing/keystrokes, individual tics, sounds, touch, typing speed, typing pattern, change in stress level, change in blood pressure, smell, change in smell, sweat, change in pulse, pulse, temperature, electrochemical modification, facial movements, body movements, body chemistry, photo, staff answers, and blood pressure.

7. A computer security method according to claim 1, wherein the individual under care has a cognitive disability.

8. A computer security method according to claim 7, wherein the individual under care has a temporary cognitive disability.

9. A computer security method according to claim 1, wherein the recording takes place in a school.

10. A computer security method according to claim 1, wherein the recording takes place in a prison.

11. A computer security method according to claim 1, wherein the individual under care is a child age birth-to-three years old.

12. A computer security method according to claim 1, wherein said recorded information is stored as contemporaneous data.

13. A computer security method according to claim 1, further comprising:
   recording second information pertaining to said individual, wherein at least a portion of said second information pertains to an initial inquiry relating to one or more goals of said individual;
   transmitting at least a portion of said second recorded information to a computer system with a memory and a processor;
   storing, by said computer system, at least a portion of said second recorded information;
   comparing, by said computer system, said historical information and at least a portion of said second transmitted information;
   determining, by said computer system, a second interpretation of at least a portion of said second transmitted information based on said comparison;
   determining, by said computer system, whether said second interpretation indicates a likelihood of negative outcome for said one or more individuals;
   determining, by said computer system, based on said indicated negative outcome, a second preventative action relating to said second indicated negative outcome; and
   transmitting, from said computer system, a signal for initiating said second preventative action.

14. A computer security method according to claim 13, wherein said portion of said stored video information is first recorded information, and further comprising storing said first recorded information as part of said historical information before comparing said second transmitted information and said historical information.

15. A computer security method according to claim 1, wherein said preventative action comprises an alert message.

16. A computer security method according to claim 1, wherein said preventative action effects change to the environmental surroundings of the individual under care.

17. A computer security method according to claim 16, wherein said wherein said environmental change includes one or more of changes to sound, light, and physical surroundings.

18. A computer security method according to claim 16, wherein said environmental change includes one or more of noise, sounds, smoke, alarms, fire alarm, smells, and vibrations.

19. A computer security method according to claim 16, wherein said environmental change includes playing music.

20. A computer security method according to claim 16, wherein:
   said negative outcome includes one or more instances of abuse and neglect; and
   said environmental change includes one more lights whose intensity is determined by a type of said one or more instances of abuse and neglect.

21. A computer security method according to claim 16, wherein said environmental change includes a change in controls.

22. A computer security method according to claim 21, wherein said change in controls includes automatically locking one or more doors.

23. A computer security method according to claim 21, wherein said change in controls includes changing access of one or more of the at least two individuals to one or more rooms.

24. A computer security method according to claim 21, wherein said change in controls includes creating a water barrier.

25. A computer security method according to claim 21, wherein said change in controls includes automatically controlling appliances.

26. A computer security method according to claim 25, wherein said automatically controlling appliances includes communicating with a sound system of a home and causing said sound system to play music.

27. A computer security method according to claim 1 wherein said storing of records of physical attributes includes storing information including data representing physical traits of the individuals.

28. A computer security method according to claim 1 wherein said signal for initiating said first protective action is configured for communication with an intelligent communication network.

29. An improved computer system providing HIPAA-compliant access of a user to electronic personal health information of an individual under care, the improvement comprising a HIPAA-compliant computer security system for recording visual personal health information in an electronic format relating to at least two individuals, at least one of whom is an individual under care, from a video camera, preventing unauthorized access of a user to said information, and initiating preventative action, comprising:
   a computer system having a memory and a processor;
   a video camera for recording personal health information including physical attributes of the individuals;
   a transmission link for sending at least a portion of said recorded video information to said computer system;
   a computer program stored in said memory and adapted to run on said processor, configured to:
   store records of physical attributes of the individual under care and the one or more individuals other than the individual under care;
   store at least a portion of said transmitted information;
   store at least one authorization profile associated with the user, wherein the user is associated with one or more roles and one or more caseloads and the caseloads include access privilege information for the individual under care, wherein said user access privilege information included in said user's caseload includes the identities of individuals under care to which the user has access;
   determine whether the user is permitted to view said information pertaining to a caseload of the individual under care wherein the determination is based on said authorization profile and the one or more caseloads and the one or more roles associated with the user, and said computer program is further configured to, as part of said determination:
   compare the stored records, of physical attributes of the individual under care and the one or more individuals other than the individual under care, to the stored video information,
   identify a portion of said stored video information pertaining to the one or more individuals other than the individual under care by matching at least one of a face, eye color, and/or hair color in the stored records of physical attributes of an individual other than the individual under care with the face, eye color, and/or hair color of an individual other than the individual under care in the stored video information, identify a portion of said stored video information pertaining to the individual under care by matching at least one of a face, eye color, and/or hair color in the stored records of physical attributes of the individual under care with the face, eye color, and/or hair color of the individual under care in the stored video information; and compare the identity of the individual under care to the user's authorization profile information, including comparing the identity of the individual under care to the user's caseload, and granting access to the user to said portion of said stored video information pertaining to the individual under care if the identity of the individual under care is stored in the user's caseload; and blur said portion of said stored video information pertaining to the one or more individuals other than the individual under care, wherein the entire image of the one or more individuals other than the individual under care is blurred, and wherein said blurring is done prior to any human viewing said stored video information;

transmit said portion of said stored video information pertaining to the individual under care, and said blurred portion of said stored video information pertaining to the one or more individuals other than the individual under care, to said caseload of said individual under care for HIPAA-compliant viewing by said user authorized to view said portion of said stored video information pertaining said the individual under care;

wherein at least a portion of said stored video information pertains to an initial inquiry relating to one or more goals of the individual under care;

store historical information, wherein said historical information pertains to said initial inquiry relating to said individual's care;

compare said historical information and at least a portion of said stored video information;

determine a first interpretation of at least a portion of said stored video information based on said comparison;

determine whether said first interpretation indicates a likelihood of negative outcome for said one or more individuals;

determine based on said indicated negative outcome, a first preventative action relating to said first indicated negative outcome; and transmit a signal for initiating said first preventative action.

30. A computer security system according to claim 29, wherein:
said stored user access privilege information included in said user's caseload includes the identities at least one program to which the user has access;
said computer program is further configured to store records of the identity of at least one program in which the individual under care is enrolled;
said computer program is further configured to, as part of said determination, compare the identity of the programs in which the individual under care is enrolled to the user's authorization profile information, including a comparison of the identity of the individual under care to the user's caseload, and grant access to the user to the portion of said stored video information pertaining to the individual under care if the identity of the program in which the individual under care is enrolled is stored in the user's caseload.

31. A computer security system according to claim 29, further comprising a device for recording information pertaining to one or more individuals, wherein at least a portion of said information pertains to an initial inquiry relating to one or more goals of said individual.

32. A computer security system according to claim 31, wherein said device is an electronic sensor.

33. A computer security system according to claim 32, wherein said electronic sensor is capable of recording one or more of voice, facial expressions, hand movements, words, biometrics, typing/keystrokes, individual tics, sounds, touch, typing speed, typing pattern, change in stress level, change in blood pressure, smell, change in smell, sweat, change in pulse, pulse, temperature, electrochemical modification, facial movements, body movements, body chemistry, photo, staff answers, and blood pressure.

34. A computer security system according to claim 29 wherein said records of physical attributes includes information including data representing physical traits of the individuals.

35. A computer security system according to claim 29 wherein said signal for initiating said first preventative action is configured for communication with an intelligent communication network.

* * * * *